United States Patent
Ji et al.

(10) Patent No.: US 11,254,943 B2
(45) Date of Patent: Feb. 22, 2022

(54) INTRON-CONTAINING PROMOTERS AND USES THEREOF

(71) Applicant: TEMASEK LIFE SCIENCES LABORATORY LIMITED, Singapore (SG)

(72) Inventors: Lianghui Ji, Singapore (SG); Yanbin Liu, Singapore (SG); Chong Mei John Koh, Singapore (SG); Sihui Amy Yap, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 621 days.

(21) Appl. No.: 16/070,648

(22) PCT Filed: Feb. 2, 2017

(86) PCT No.: PCT/SG2017/050046
§ 371 (c)(1),
(2) Date: Jul. 17, 2018

(87) PCT Pub. No.: WO2017/135895
PCT Pub. Date: Aug. 10, 2017

(65) Prior Publication Data
US 2020/0377898 A1   Dec. 3, 2020

Related U.S. Application Data

(60) Provisional application No. 62/292,030, filed on Feb. 5, 2016.

(51) Int. Cl.
*C12N 15/81* (2006.01)
*C12P 1/02* (2006.01)

(52) U.S. Cl.
CPC .............. *C12N 15/815* (2013.01); *C12P 1/02* (2013.01)

(58) Field of Classification Search
None
See application file for complete search history.

(56) References Cited

U.S. PATENT DOCUMENTS

2006/0019297 A1   1/2006  Picataggio et al.

FOREIGN PATENT DOCUMENTS

| WO | 2005049805 A2 | 6/2005 |
| WO | 2012169969 A1 | 12/2012 |
| WO | 2014142747 A1 | 9/2014 |
| WO | 2016039685 A2 | 3/2016 |

OTHER PUBLICATIONS

International Search Report and Written Opinion issued in Application No. PCT/SG2017/050046 dated Apr. 20, 2017, 16 pages.
Nicolas Morin et al. "Draft Genome Sequence of Rhodosporidium toruloides CECT1137, an Oleaginous Yeast of Biotechnological Interest", Genome Announcements, Journals.ASM.org, Jul./Aug. 2014, vol. 2:4, 2 pages.
Yanbin Liu et al. "Engineering an efficient and tight D-amino acid-inducible gene expression system in Rhodosporidium/Rhodotorula species", Microbial Cell Factories, vol. 14:170, 2015, BioMed Central, 16 pages.
Yanan Wang et al. "Cloning and evaluation of different constitutive promoters in the oleaginous yeast *Rhodosporidium toruloides*", Yeast 2016, vol. 33:99-106, Published online Jan. 14, 2016 in Wiley Online Library, 8 pages.
Alexander M.B. Johns et al. "Four Inducible Promoters for Controlled Gene Expression in the Oleaginous Yeast *Rhodotorula toruloides*", Frontiers in Microbiology, Published Oct. 21, 2016, 12 pages.
Yanbin Liu et al. "Developing a set of strong intronic promoters for robust metabolic engineering in oleaginous Rhodotorula (*Rhodosporidium*) yeast species", Microbial Cell Factories, vol. 15:200, 2016, BioMed Central, 9 pages.
European Search Report and Written Opinion issued in European Application No. 17747883.1, dated May 28, 2019, 14 pages.
Extended European Search Report issued for European Patent Application No. 17747383.1 dated Aug. 29, 2019, 13 pgs.
Yanbin Liu et al. "Developing a set of strong intronic promoters for robust metabolic engineering in oleaginous Rhodotorula (*Rhodosporidium*) yeast species", Microbial Cell Factories, (2016) 15:200, 9 pgs.
Yanbin Liu et al. "Engineering an efficient and tight d-amino acid-inducible gene expression system in *Rhodosporidium/Rhodatorula* species", Microbial Cell Factories, (2015) 14:170, pp. 16 pgs.
Nicolas Morin et al. "Draft Genome Sequence of Rhodosporidium toruloides CECT1137, an Oleaginous Yeast of Biotechnological Interest", GenomeA Journals.Asm.org, Jul./Aug. 2014, vol. 2, Issue 4, 2 pgs.
First Official Action issued in corresponding Chinese Application No. 201780022143.4, with an English Language Translation, dated Jun. 17, 2021, 19 pages.

*Primary Examiner* — Kagnew H Gebreyesus
(74) *Attorney, Agent, or Firm* — Rothwell, Figg, Ernst & Manbeck, P.C.

(57) ABSTRACT

The present invention relates to the field of molecular biology and more particularly to promoters useful for metabolic engineering in yeast or fungi for the production of biobased chemicals with broad applications. Intron-containing promoters with strong activity during oil-accumulation stages are particularly useful for genetic engineering in yeast and fungi, particularly *Rhodosporidium* or *Rhodotorula* genera. Such promoter are capable of driving strong expression of RNA or proteins in species of the *Rhodosporidium* or *Rhodotorula* genera.

19 Claims, 11 Drawing Sheets
Specification includes a Sequence Listing.

Fig. 1
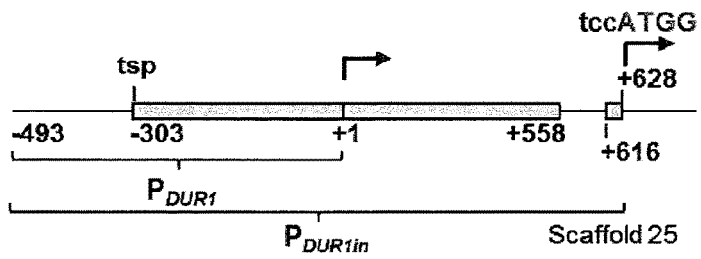
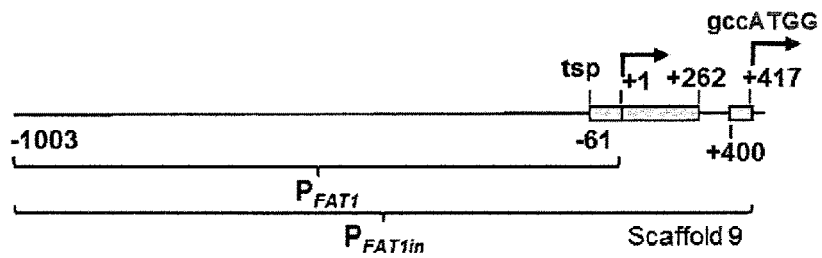
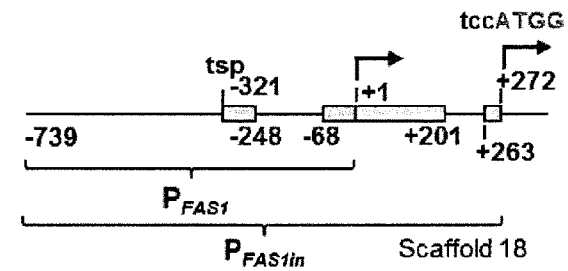
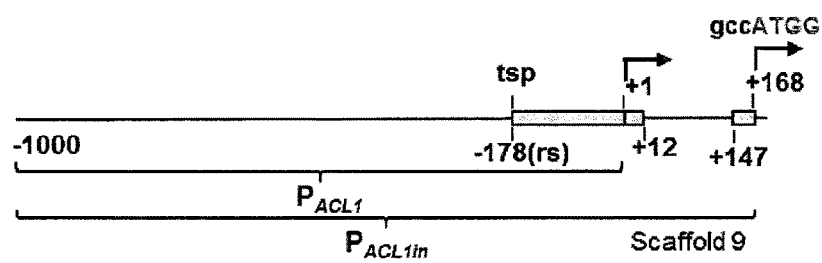
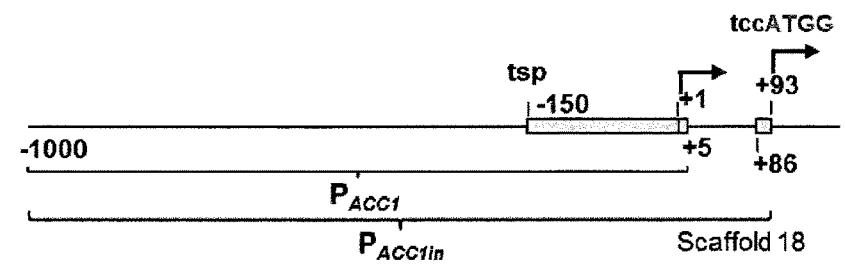
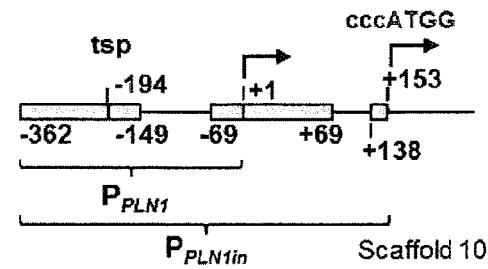

Fig. 4

A
```
-199  cgcgccttg tccgcttccc catcctcgtc ctgtcttgc tctcttcct
                                              ct box
-150  ACCACACTCT CCCGCTTGCG GGCTCTCTTT CTCGCTTGGC GCTCCTGCTA
      ↑tsp
-100  CCGCTACTCT AGACTCTCCT AGTCTCCCTG CACAACCATC CCTATCCCCT
                                       EXON#1
-050  CCGCCTCTCT CGCACACCCC CCACAGCTTC GTTCCCCAAC TTCACTTCCG +001  ATGCCgtgcg tcgcctccct ttcgcctggc gggcccgcgc ctgcttccga
      M  P                 intron#1             CCATGG RtLUC2
+051  ggacaactac tgattgtggg atcatgcgac gacagGTTCT CTGGCGAGGC
                                            F   S  EXON#2
```

B
```
-362                                           CA CGCCTCTGTG
-350  ACTCGGTACG GAGAGAGAGA GCGTTGGGTT GGGTTGGGGA TTGTGGCGAG
-300  CGAAGGGCGA CCCAGCAGCC AGGGAGAGGG AGTTGGTCTG GATGCAAACC
-250  ATGCGCATCT CCTCTCGCAG TTGAATCGTT TTTCCCGCTC TGCCCCTCdct
-200  ctctcttcct tctgctcttt ACTCGCTCAC GAACAACAAC GAGCCACACA
         ct box       ↑tsp            EXON#1
-150  GCgtgagcac acaccgctgc actcactcgc tgtcacggac cgcagctcac
                          intron#1
-100  ccttatcgtc actcctctc ccacgcaca g
-050         ACA AGCACAACAC ACGGCACACT CGCACGCACA CTCGCACGCA
                                  EXON#2
+001  ATGGCCACCG TCAACGAGAA GCAGCCCGCC ACCGACGCGC CCCTCGCGCA
      M  A  T  V  N  E  K  Q  P  A  T  D  A  P  L  A  H
+051  CGAGACCGCC ATCCACCGCg tgcgtccca tcctcccac tgtcttccta
      E  T  A  I  H  R
+101  gtgaaacccg ctcacccgtt cgcaagcaca cacgcagGTG TCGGACTACG
                      intron#2                   V  S  D  Y
      CCATGG  RtLUC2                                  EXON#3
+151  CCGTGATCAA AGACACCCTC TCCTCGCTCG ACTCGTACGC CCACTCGCAC
      P  V  I  K  D  T  L  S  S  L  D  S  Y  A  H  S  H
```

C gtgcgtcgcctccctttcgcctGGCGGGCCCGCGCCtgcttccg
aggacaactactgattgtgggatcatgcgacgacag

D

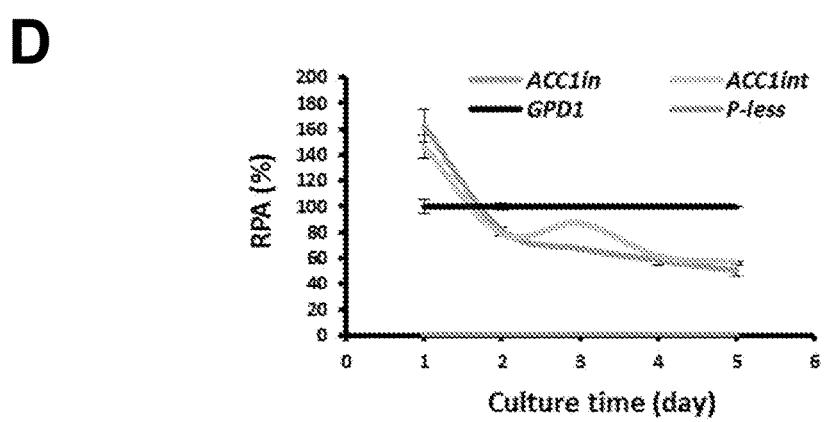

Fig. 5
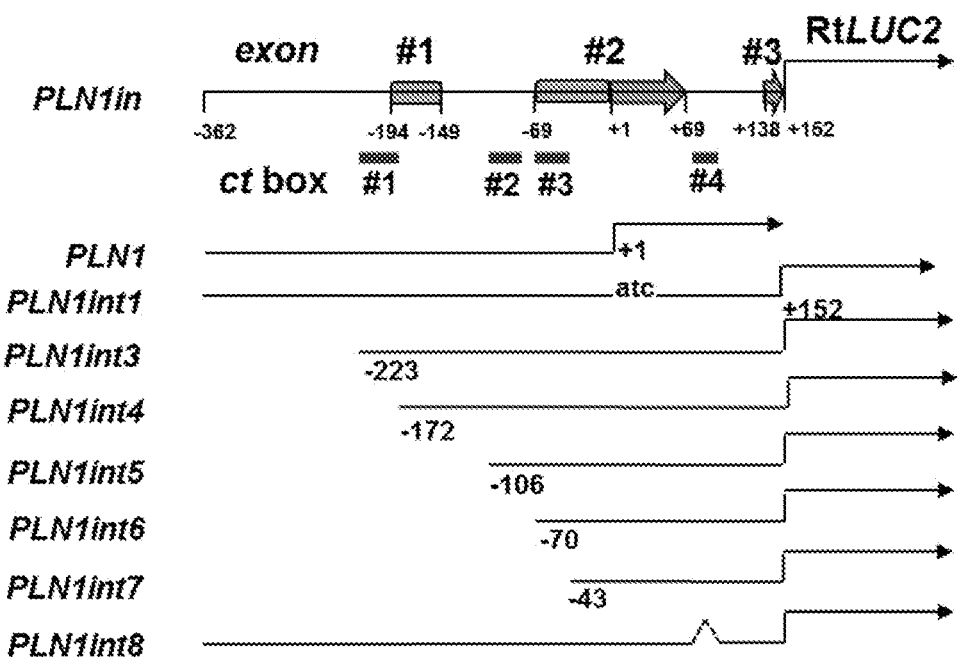
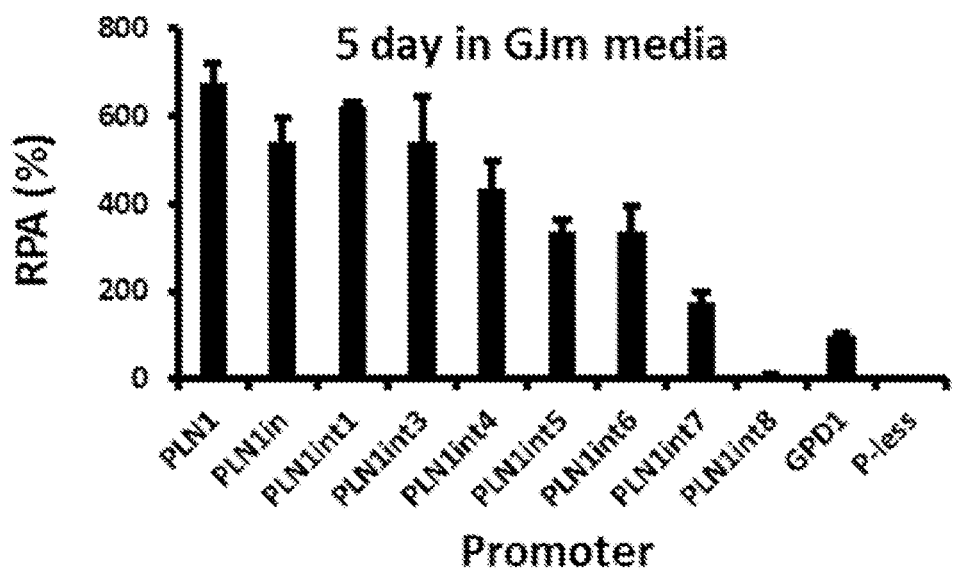

Fig. 7
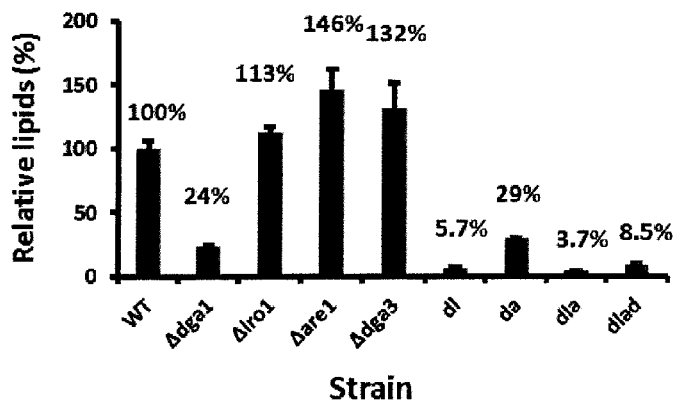
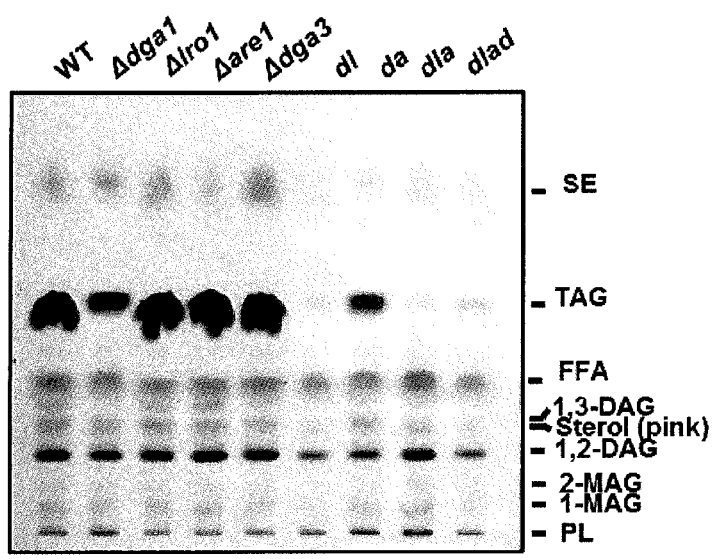
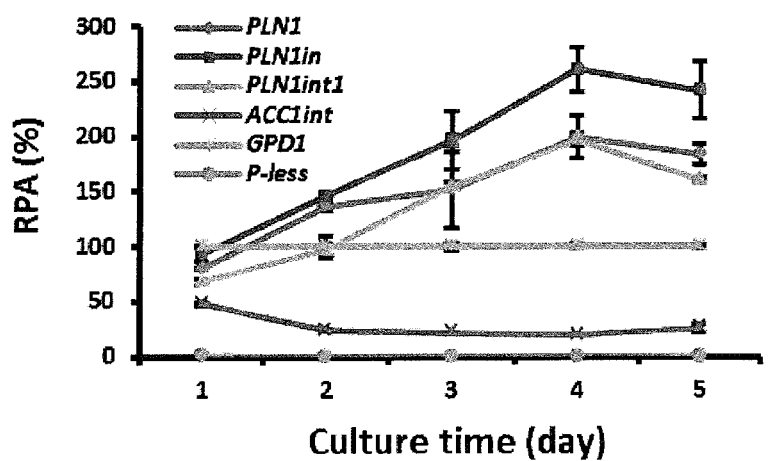

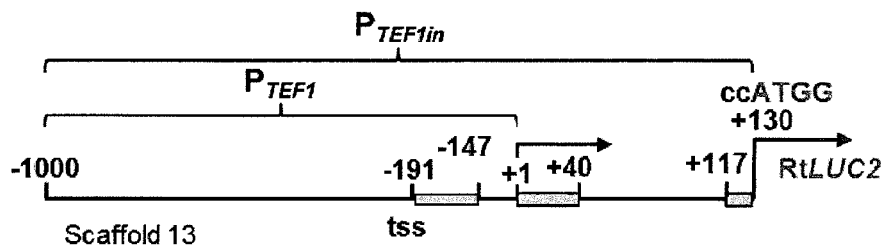

B

```
-1000  GCACGCGAAG  CGGTAGAAGC  AATGAAGCGA  GGCGAGAGCG  AGAGAGGCAG
-0950  GGCTTCAGCC  ATGTCCAGCT  GATCGGCTGT  AACGTCGCGC  CGGGCCAGTC
-0900  TGTTGAATTT  GTTGCGTCGC  CTGAGCGTAA  TAGAAGTGCA  GTAGTCTACT
-0850  CCGCATGCCG  AGAACGTCGA  AGAGCGCGAA  GTAGGGAGTC  GAGGGAAGCG
-0800  AGGGTGGCAA  ACACAGCAAC  GACAAGCGGT  TCCGCTTCGC  TCAAAAGCTC
-0750  GTTGACGTTG  TTTTGACGTT  TTGAAGACAG  TACAACAGCA  GCAAGAGGCG
-0700  TGCGAAGCGT  TGGTGGCGAG  AGCAGCGACA  AGGAGGGAGG  AATGAGGGAG
-0650  TGGTGGCGAG  GGCTCGCAAA  CGGGCGTACG  CCTCGAATGG  AGACGTGCGA
-0600  GTCGTTCTTC  GACGTCCGAG  GGATGCCGAG  CGCCGAGACG  GAGCACGCAA
-0550  CGAGCGAGAG  GAGAGCAGCC  GCGCAAGGTG  ATTCGAGTGG  CGCAAGCGGA
-0500  GGACGACGAG  GAGACGGACG  AGGGAGGAGG  AGGGATGGCG  AGCGAGCATC
-0450  GGACGGCGGG  GCGCGAGAGA  CGGCGTGAGG  AGCCGGGTGT  GGAGAGTTTG
-0400  AGGAGGCGCG  GGATGCGAAG  TGGCTGGGTG  TGCGGAGTGA  GCGGTGGCAA
-0350  AGAGCGCACT  TAGAGTCTAG  AGCGAGGCAG  TAGTAGTAGA  GCTGTATGAA
-0300  TGAATACAAA  GTGTGAATAC  AACAGTTTGT  AATGCGATTC  TGAGCTTGGA
-0250  CGTGTGCGCG  CGAGAGGGCG  ACTTGCAAGC  CAGCGCCCGC  TCGCTCTTCT
-0200  TCCTTCTGCA  CCTCGCGTCA  ACCCTCGCAT  CTCACACCTA  CACTCGCATT
         ct box      tss                  EXON#1
-0150  CAAAgtgcgt  acactctccc  acgacacacg  gggacggcgc  acaccaccgc
-0100  gcgtcgcttg  aacggcgtcg  ccacttcgag  ccgtcactga  cttcgtcctc
                                  intron#1
-0050  gtcctccctc  ctctactctc  ttgtactgta  ctgtgtactg  gggggatag
+0001  ATGGGCAAGG  AAAAGGGACA  CGTCAACGTC  GTCGTTATCG  gtacgttcag
  P01   M  G  K   E  K  G  H   V  N  V    V  V  I
+0051  cgtcgtcgag  gcgagtctgg  cgaggaggag  gacgtcgagc  tgacctcgcc
                              intron#2                       RtLUC2
+0101  ccgtcctccc  gcgcagGCCA  CGTCGACTCC  GGCAAGTCGA  CCACCACCGG
  P14                  G  H   V  D  S     G  K  S    T  T  T  G
```

INTRON-CONTAINING PROMOTERS AND USES THEREOF

CROSS REFERENCE TO RELATED APPLICATIONS

The present application is a national stage filing under 35 U.S.C. § 371 of PCT/SG2017/050046, filed on 2 Feb. 2017, which is related to and claims the benefit of priority to U.S. Provisional Patent Application Ser. No. 62/292,030 filed 5 Feb. 2016. Each application is incorporated herein by reference in its entirety.

SEQUENCE SUBMISSION

The present application is being filed along with a Sequence Listing in electronic format. The Sequence Listing is entitled 2577251PCTSequenceListing.txt, created on 27 Jan. 2017 and is 83 kb in size. The information in the electronic format of the Sequence Listing is incorporated herein by reference in their entirety.

BACKGROUND OF THE INVENTION

The present invention relates to the field of molecular biology and more particularly to promoters useful for metabolic engineering in yeast or fungi for the production of biobased chemicals with broad applications. Intron-containing promoters with strong activity during oil-accumulation stages are particularly useful for genetic engineering in yeast and fungi, particularly *Rhodosporidium* or *Rhodotorula* genera. Such promoter are capable of driving strong expression of RNA or proteins in species of the *Rhodosporidium* or *Rhodotorula* genera.

The publications and other materials used herein to illuminate the background of the invention, and in particular, cases to provide additional details respecting the practice, are incorporated by reference, and for convenience are referenced in the following text by number and are listed by number in the appended bibliography.

*Rhodosporidium* (teleomorph) or *Rhodotorula* (anamorph) are phylogenetically highly related yeast and excellent producers of oil (triacyglyceride) and carotenoids [1, 2]. Dry biomass yield of more than 100 g/L could be readily produced within a week with more than 60% oil content [3-5]. To take advantage of its high metabolic flux and cell mass production, we are developing it as a new synthetic biology platform. To date, several genetic manipulation tools such as *Agrobacterium tumefaceins*-mediated transformation, high efficiency gene deletion and constitutive and inducible promoter sets for *Rhodosporidium* have been reported [6-9]. As repetitive DNA sequences, such as promoters repeatedly used will result in instability of the transgenes in the engineered cells due to homologous DNA recombination, a diverse pool of promoters are critical for metabolic engineering. As *Rhodosporidium* species are outstanding oil producers, strong and robust promoters that function during oil accumulation stage are particularly useful.

Acetyl-CoA carboxylase (ACC) catalyzes the biotin-dependent carboxylation of acetyl-CoA to form malony-CoA, a step generally believed to first committed and rate-limiting for fatty acid biosynthesis [10]. While this protein was found highly abundant in proteomic study [4], the 1638 bp DNA fragment (from −1638 nt to the predicted translation initiation codon ATG) was found to have little promoter activity previously [11]. Another two proteins, fatty acid synthase subunit 2 and fatty acid transporter, also showed high protein levels after lipid production. [12]. However, the promoter sequences have not been defined.

ATP:citrate lyase (ACL) is another enzyme with an important role in lipogenesis [13]. The *R. toruloides* ACL1 was found highly expressed during lipid accumulation [12]. Similarly, the urea carboxylase/allophanate hydrolase (Dur1) showed higher protein levels in lipid accumulation condition than in non-lipid accumulation condition [12].

Except the separate enzyme activity of acetyl-CoA carboxylase, in *Saccharomyces cerivisiae*, the activities of fatty acid synthesis are distributed between two yeast proteins, Fas1p and Fas2p, the β and α subunits of a large, barrel-shaped complex containing 6 copies of each protein (α6β36) [14]. The six Fas1p and six Fas2p subunits form six independent reaction centers, each containing all enzyme activities required for synthesizing long chain fatty acids from acetyl- and malony-CoA [15, 16]. FAS1 encodes four independent enzymatic functions: acetyltransferase (EC: 2.3.1.38), enoyl reductase (EC:1.3.1.10), dehydratase (EC: 4.2.1.61), and malonyl/palmitoyl-transferase (EC:2.3.1.39) [17]. FAS2 encodes the acyl-carrier protein domain and three independent enzymatic functions: 3-ketoreductase (EC:1.1.1.100), 3-ketosynthase (EC:2.3.1.41) and phosphopantetheinyl transferase (EC:2.7.8.7) [18]. In *S. cerivisiae*, FAS1 and FAS2 are both constitutively activated by general transcription factors Rap1p, Abf1p, and Reb1p [19] and further activated by the inositol/choline-responsive transcription factor heteroduplex, Ino2p-Ino4p [20, 21]. Furthermore, Fas1p and Fas2p stoichiometry appears to be insured by a regulatory mechanism in which Fas1p protein controls FAS2 mRNA levels [22].

PAT family proteins (perilipin, adipophilin, TIP47) are abundant proteins in lipid droplets [23] in several fungi, such as *Yarrowia lipolytica* [24], *Metarhizium anisopliae* [25] and *R. toruloides* [26]. The *R. toruloides* perilipin (Pln1) was also known as the lipid droplet protein (Ldp1) and its accumulation level was increased during nitrogen starvation [26]. Perilipins were proposed to serve as a dynamic scaffold, regulating formation, growth and lipolysis of lipid bodies [27]. Another gene involved in oil production is fatty acid transporter gene (FAT1) [26].

SUMMARY

The present invention relates to the field of molecular biology and more particularly to promoters useful for metabolic engineering in yeast or fungi for the production of biobased chemicals with broad applications. Intron-containing promoters with strong activity during oil-accumulation stages are particularly useful for genetic engineering in yeast and fungi, particularly *Rhodosporidium* or *Rhodotorula* genera. Such promoter are capable of driving strong expression of RNA or proteins in species of the *Rhodosporidium* or *Rhodotorula* genera.

In one aspect, the present invention provides a promoter operable in yeast or fungi that is useful for controlling expression of a nucleic acid operably linked to the promoter. In some embodiments, the promoter contains one or more introns. In other embodiments, the promoter is modified to delete the original start codon. In further embodiments, the promoter is also modified to introduce a new start codon into the promoter for expression of a nucleic acid of interest that is operably linked to the modified promoter. In other embodiments, the modification to introduce a new start codon also includes a restriction enzyme site for cloning the nucleic acid of interest. In one embodiment, the promoter is derived from the acetyl-CoA-carboxylase gene (ACC1). In another embodiment, the promoter is derived from the perilipin gene (PLN1). In a further embodiment, the promoter is derived from the fatty acid synthetase 1 gene (FAS1). In an additional embodiment, the promoter is derived from the ATP:citrate lyase gene (ACL1). In another embodiment, the promoter is derived from the translational elongation factor EF-1 alpha (TEF1). In some embodiments, the promoter includes all of the 5' upstream promoter sequence. In other embodiments, the promoter includes a part of the 5' upstream promoter sequence. In each instance the derived promoter retains functional promoter activity. In some embodiments, promoter described herein are capable of driving strong expression in species of the *Rhodosporidium* or *Rhodotorula* genera.

In some embodiments, the promoter comprises a nucleic acid sequence of at least 75% sequence identity, based on the Clustal V or Clustal W method of alignment, when compared to an ACC1in promoter of any one of SEQ ID NOs:74, 77, 80, 81, 82, 83, 87, 88, 89, 90, 91 or 92. In other embodiments, the promoter comprises a nucleic acid sequence of at least 75% sequence identity, based on the Clustal V or Clustal W method of alignment, when compared to a PLN1in promoter of any one of SEQ ID NOs:75, 85, 93 or 94. In additional embodiments, the promoter comprises a nucleic acid sequence of at least 75% sequence identity, based on the Clustal V or Clustal W method of alignment, when compared to a FAS1in promoter of any one of SEQ ID NOs:76, 86, 95 or 96. In further embodiments, the promoter comprises a nucleic acid sequence of at least 50% sequence identity, based on the Clustal V or Clustal W method of alignment, when compared to an ACL1in promoter of any one of SEQ ID NOs:79 or 97. In further embodiments, the promoter comprises a nucleic acid sequence of at least 50% sequence identity, based on the Clustal V or Clustal W method of alignment, when compared to an TEF1in promoter of any one of SEQ ID NOs:115-122. In some embodiments, the promoter comprises any one of the preceding sequences in which the 3' ATGG or ATG sequence is deleted. In other embodiments, the promoter comprises a nucleotide sequence, wherein the nucleotide sequence is hybridizable under stringent conditions with a DNA molecule comprising the full complement of any one of SEQ ID NOs:74-77, 79-83, 85-85-96 or 97 or 115-122.

In another aspect, the present invention provides a recombinant DNA construct (also referred to as a nucleic acid construct) useful for expressing a nucleic acid of interest in a yeast or fungi, or in a yeast or fungal cell. In some embodiments, the recombinant DNA construct comprises a promoter described herein operably linked to a nucleic acid of interest. In some embodiments, the nucleic acid of interest encodes a protein useful for the production of biobased chemicals with broad applications. In some embodiments, the biobased chemicals may be fatty acids, fatty alcohols, terpenes and carotenoids. In other embodiments, the nucleic acid of interest encodes terpene synthases, P450 cytochrome oxidases, fatty acid reductases, fatty acid-CoA reductases. In some embodiments, the coding sequence of the nucleic acid of interest is modified to contain at least 55% G and C content, preferably 60%-70% G and C content. In other embodiments, at least 70% of the codons have a C or G at the third position.

In a further aspect, the present invention provides a transgenic yeast or fungi or a transgenic yeast or fungal cell comprising the recombinant DNA construct described herein. In some embodiments, the recombinant DNA construct is stably integrated into the transgenic yeast or fungi or transgenic yeast or fungal cell. In other embodiments, the recombinant DNA construct is transiently introduced into the transgenic yeast or fungi or transgenic yeast or fungal cell. The present invention also provides methods for preparing the transgenic yeast or fungi or transgenic yeast or fungal cell. In other embodiments, the transgenic yeast or fungi or transgenic yeast or fungal cell is part of a composition also comprising a culture medium. In some embodiments, the yeast is a species of the *Rhodosporidium* genus. In other embodiments, the yeast is a species of the *Rhodotorula* genus.

BRIEF DESCRIPTION OF THE FIGURES

FIGS. 1A-1F show schematic diagrams of promoters. FIG. 1A: Promoters of intron-less and intron-containing promoter DUR1 and DUR1in. FIG. 1B: FAT1 promoter. FIG. 1D Promoters of intron-less and intron-containing promoter ACL1 and ACL1in. FIG. 1E: Promoters of intron-less and intron-containing promoter ACC1 and ACC1in. FIG. 1F: Promoters of intron 2-less and intron 2-containing promoter PLN1 and PLN1in.

FIG. 2A: Schematic diagram of promoter fragments. FIG. 2B: Relative promoter activity (RPA) based luciferase gene assays. Cells were cultured in MinRL2 for 4 days. RPA (%) was compared to the 1.6 kb intron-containing $P_{ACC1in}$ promoter.

FIG. 3A: ACC1 and ACC1 in promoter. FIG. 3B: PLN1 and PLN1in promoter. FIG. 3C: FAS1 and FAS1in promoter. FIG. 3D: ACL1 and ACL1in. FIG. 3E: DUR1 and DUR1in promoter. FIG. 3F: FAT1 promoter.

FIGS. 4A-4D show structures of ACC1in and PLN1in promoters. FIG. 4A: ACC1in promoter (SEQ ID NO:1). FIG. 4B: PLN1in promoter (SEQ ID NO:2). Major features such as ct box (CT rich cis-acting element), introns and sequence changes are indicated. tsp: transcriptional start point as determined by 5' RACE. The ct boxes are as follows: #1: nucleotides −222 to −181; #2: nucleotides −105 to −079; #3: nucleotides −069 to −044; and #4: nucleotides +075 to +100. FIG. 4C: Sequence of the intron and the GC-rich motif #4 (SEQ ID NO:3) of the ACC1in promoter. FIG. 4D: Comparison of Wt 0.3 kb ACC1in with the modified ACC1int promoter fragment. ACC1int contains ATG>ATC and CTGGCG to CCATGG mutations (See FIG. 4A). Cells were cultured in MinRL2 for 5 days and the relative promoter activity (RPA) was normalized against GPD1 promoter activity. The amino acid sequences in FIG. 4A and FIG. 4B are set forth in SEQ ID NOs:73 and 78, respectively.

FIGS. 5A and 5B show the characterization of PLN1in promoter. FIG. 5A: Schematic diagram of serial deletions and potential sites of cis-acting elements CT-boxes. PLN1int 1-8 illustrate various mutations and sequence truncations. FIG. 5B: Relative promoter strength (RPA %). Cells were cultured in GJm medium for 5 days. Activity of $P_{GPD1}$ was set as 100%.

FIGS. 7A-7C show lipid production and lipid profiles. FIG. 7A: relative lipid yields in *R. toruloides* WT and diacylglycerol acyltransferase mutant strains. Lipid yield in WT strain was normalized to 100%. FIG. 7B: Fatty acid profiles in *R. toruloides* WT and DGAT mutant strains. Abbreviation of DGAT mutants: dl—Δdga1Δlro1; da—Δdga1Δare1; dla—Δdga1Δlro1Δare1; dlad—Δdga1Δlro1Δare1Δdga3. Abbreviation of lipid components: SE—sterol ester; TAG—triacylglycerol; FFA—free fatty acids; DAG—diacylglycerol; MAG: monoacylglycerol; PL—polar lipids. FIG. 7C: Reporter constructs of PLN1, PLN1in, PLN1int, ACC1int, GPD1 and P-less were made in dlad mutant and cultured in MinRL3 for 5 days.

FIGS. 9A and 9B show a schematic diagram and nucleotide sequence of promoter TEF1 and TEF1in. FIG. 9A: Scheme of TEF1 and TEF1in. FIG. 9B: Sequence of TEF1 and TEF1in. tss—transcriptional start site, ct box—CT rich cis-acting element. The nucleotide sequence is set forth in SEQ ID NO:107. The protein sequences are set forth in SEQ ID NOs:108 and 109.

FIG. 11A: Schematic diagram of TEF1in promoter and its truncation fragments. TEF1inm1 behaves the site-directed mutation in its translational start codon (ATG to ATC) to eliminate the translation of N-terminus 18 aa of Tef1 before the target protein. TEF1inm2~5 indicate the serial truncation of promoter sequence. FIG. 11B: Promoter assay in two different medium, a lipid accumulation medium GJ2013 and a rich medium YPD. Cells were cultured at 28° C., 280 rpm for 2 days.

DETAILED DESCRIPTION OF THE INVENTION

Figure 2:
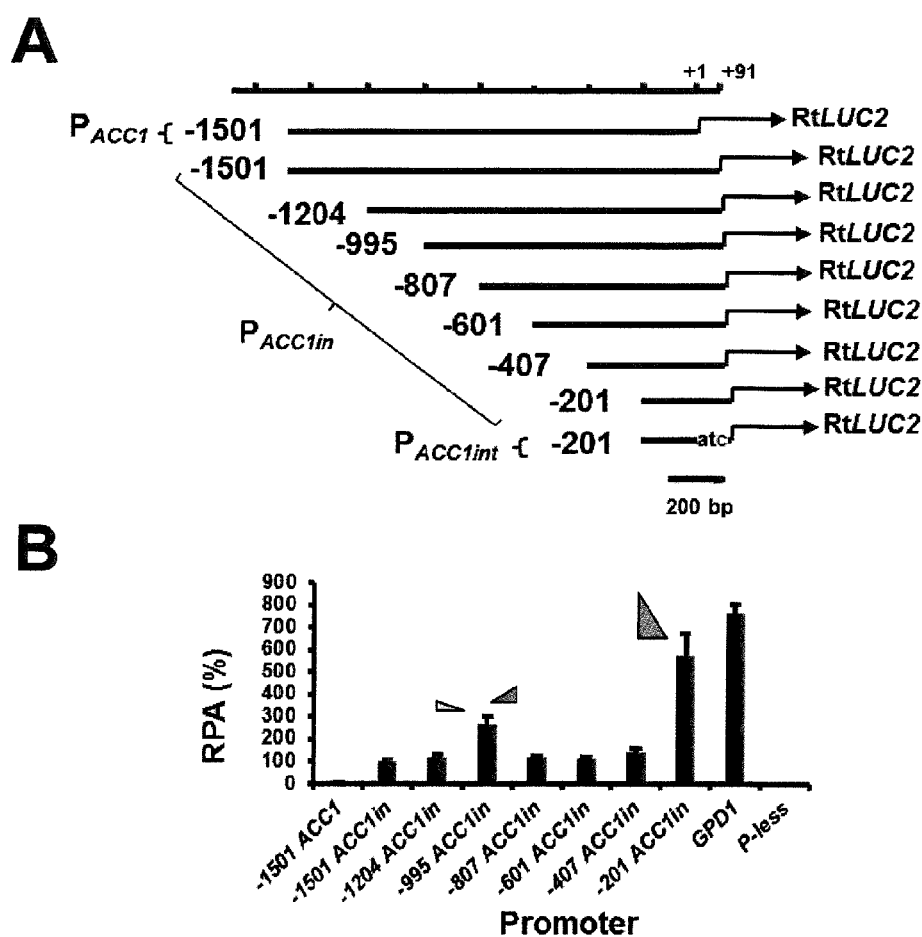
FIG. 2C: Promoters of intron 2-less and intron 2-containing promoter FAS1 and FAS1in.
FIGS. 2A and 2B show the characterization of the intron-containing ACC1in promoter.

The present invention relates to the field of molecular biology and more particularly to promoters useful for metabolic engineering in yeast or fungi for the production of biobased chemicals with broad applications. Intron-containing promoters with strong activity during oil-accumulation stages are particularly useful for genetic engineering in yeast and fungi, particularly *Rhodosporidium* or *Rhodotorula* genera. Such promoter are capable of driving strong expression of RNA or proteins in species of the *Rhodosporidium* or *Rhodotorula* genera.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

"Constitutive promoter" refers to a promoter which is capable of causing a gene to be expressed in most cell types at most. A "strong constitutive promoter" refers to a constitutive promoter that drives the expression of a mRNA to the top 10% of any mRNA species in any given cell.

A "control" or "control yeast or fungi" or "control yeast or fungal cell" provides a reference point for measuring changes in phenotype of a subject yeast or fungi or yeast or fungal cell in which genetic alteration, such as transformation, has been effected as to a polynucleotide of interest. A subject yeast or fungi or yeast or fungal cell may be descended from a yeast or fungi or cell so altered and will comprise the alteration.

A control yeast or fungi or yeast or fungal cell may comprise, for example: (a) a wild-type yeast or fungi or yeast or fungal cell, i.e., of the same genotype as the starting material for the genetic alteration which resulted in the subject yeast or fungi or yeast or fungal cell; (b) a yeast or fungi or yeast or fungal cell of the same genotype as the starting material but which has been transformed with a null construct (i.e., with a construct which has no known effect on the trait of interest, such as a construct comprising a marker gene); (c) a yeast or fungi or yeast or fungal cell which is a non-transformed segregant among progeny of a subject yeast or fungi or yeast or fungal cell; (d) a yeast or fungi or yeast or fungal cell genetically identical to the subject yeast or fungi or yeast or fungi cell but which is not exposed to conditions or stimuli that would induce expression of the polynucleotide of interest or (e) the subject yeast or fungi or yeast or fungal cell itself, under conditions in which the polynucleotide of interest is not expressed.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence. "Strong expression" refers to the expression of a mRNA or protein to the top 10% of any mRNA or protein species in any given cell.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

The term "heterologous" or "exogenous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous or exogenous protein indicates that the protein comprises two or more subsequences that are not found in the same relationship to each other in nature (e.g., a fusion protein).

"Introduced" in the context of inserting a nucleic acid fragment (e.g., a recombinant DNA construct) into a cell, means "transfection" or "transformation" or "transduction" and includes reference to the incorporation of a nucleic acid fragment into a yeast or fungi cell where the nucleic acid fragment may be incorporated into the genome of the cell (e.g., chromosome, plasmid or mitochondrial DNA), converted into an autonomous replicon, or transiently expressed (e.g., transfected mRNA).

"Operable linkage" or "operably linked" or "operatively linked" as used herein is understood as meaning, for example, the sequential arrangement of a promoter and the nucleic acid to be expressed and, if appropriate, further regulatory elements such as, for example, a terminator, in such a way that each of the regulatory elements can fulfill its function in the recombinant expression of the nucleic acid to make the desired product. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another. Regulatory or control sequences may be positioned on the 5' side of the nucleotide sequence or on the 3' side of the nucleotide sequence as is well known in the art.

"Over-expression" or "overexpression" refers to the production of a gene product in transgenic organisms that exceeds levels of production in normal, control or non-transformed organisms.

As used herein, "phenotype" refers to the detectable characteristics of a cell or organism, which characteristics are the manifestation of gene expression.

The terms "polynucleotide," "nucleic acid" and "nucleic acid molecule" are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation. Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

"Progeny" comprises any subsequent generation of a transgenic yeast or fungi or a transgenic yeast or fungal cell.

"Promoter" refers to a nucleic acid fragment capable of controlling transcription of another nucleic acid fragment.

"Promoter functional in a yeast or fungi" is a promoter capable of controlling transcription in yeast or fungal cells whether or not its origin is from a yeast or fungal cell.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein. In several embodiments described herein, a recombinant DNA construct may also be considered an "over expression DNA construct." The term "nucleic acid construct" may also be used interchangeably with "recombinant DNA construct."

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

A "trait" refers to a physiological, morphological, biochemical, or physical characteristic of a yeast or fungi or a particular yeast or fungal material or cell. In some instances, this characteristic can be measured by biochemical techniques, such as detecting the material produced in the yeast or fungi.

"Transformation" as used herein refers to both stable transformation and transient transformation.

A "transformed cell" is any cell into which a nucleic acid fragment (e.g., a recombinant DNA construct) has been introduced.

"Transgenic yeast or fungi" includes reference to a yeast or fungi which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct. "Transgenic yeast or fungi" also includes reference to yeast or fungi which comprise more than one heterologous polynucleotide within their genome. Each heterologous polynucleotide may confer a different trait to the transgenic yeast or fungi. A "transgenic yeast or fungi" encompasses all descendants, hybrids, and crosses thereof and which continue to harbor the foreign DNA.

"Transient transformation" refers to the introduction of a nucleic acid fragment into the nucleus, or DNA-containing organelle, of a host organism resulting in gene expression without genetically stable inheritance.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., *Molecular Cloning: A Laboratory Manual*, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

As used herein, the term "substantially homologous" or "substantial homology", with reference to a nucleic acid sequence, includes a nucleotide sequence that hybridizes under stringent conditions to a referenced SEQ ID NO:, or a portion or complement thereof, are those that allow an antiparallel alignment to take place between the two sequences, and the two sequences are then able, under stringent conditions, to form hydrogen bonds with corresponding bases on the opposite strand to form a duplex molecule that is sufficiently stable under conditions of appropriate stringency, including high stringency, to be detectable using methods well known in the art. Substantially homologous sequences may have from about 70% to about 80% sequence identity, or more preferably from about 80% to about 85% sequence identity, or most preferable from about 90% to about 95% sequence identity, to about 99% sequence identity, to the referent nucleotide sequences as set forth the sequence listing, or the complements thereof. Alternatively, substantially homologous sequences include those which hybridize under stringent conditions to the target regions of introns of plant genes. For stringency conditions, see the description herein and see also U.S. Pat. Nos. 8,455,716 and 8,536,403.

Embodiments of the present invention which include isolated polynucleotides and recombinant DNA constructs useful for conferring regulation of protein expression, compositions (such as transgenic yeast or fungi) comprising these recombinant DNA constructs, and methods utilizing these recombinant DNA constructs are now described.

Isolated Promoters

The present invention provides isolated promoters for expression of a heterologous polynucleotide in a yeast or fungal species. In some embodiments, the promoter contains one or more introns. In other embodiments, the promoter is modified to delete the original start codon. In further embodiments, the promoter is also modified to introduce a new start codon into the promoter for expression of a nucleic acid of interest that is operably linked to the modified promoter. In other embodiments, the modification to introduce a new start codon also includes a restriction enzyme site for cloning the nucleic acid of interest. In one embodiment, the promoter is derived from the acetyl-CoA-carboxylase gene (ACC1). In another embodiment, the promoter is derived from the perilipin gene (PLN1). In a further embodiment, the promoter is derived from the fatty acid synthetase 1 gene (FAS1).). In another embodiment, the promoter is derived from the translational elongation factor EF-1 alpha (TEF1). In some embodiments, the promoter includes all of the 5' upstream promoter sequence. In other embodiments, the promoter includes a part of the 5' upstream promoter sequence. In each instance the derived promoter retains functional promoter activity. In some embodiments, promoter described herein are capable of driving strong expression in species of the *Rhodosporidium* or *Rhodotorula* genera.

In one embodiment, the promoter comprises a nucleic acid sequence of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to an ACC1in promoter of any one of SEQ ID NOs:74, 77, 80, 81, 82, 83, 87, 88, 89, 90, 91 or 92. In some embodiments, the promoter comprises any one of the preceding ACC1in promoter sequences in which the 3' ATGG or ATG sequence is deleted.

In another embodiment, the promoter comprises a nucleic acid sequence of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to a PLN1in promoter of any one of SEQ ID NOs:75, 85, 93 or 94. In some embodiments, the promoter comprises any one of the preceding PLN1in promoter sequences in which the 3' ATGG or ATG sequence is deleted.

In a further embodiment, the promoter comprises a nucleic acid sequence of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to a FAST in promoter of any one of SEQ ID NOs:76, 86, 95 or 96. In some embodiments, the promoter comprises any one of the preceding FAS1in promoter sequences in which the 3' ATGG or ATG sequence is deleted.

In a further embodiment, the promoter comprises a nucleic acid sequence of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to an ACL1in promoter of any one of SEQ ID NOs:79 or 97. In some embodiments, the promoter comprises any one of the preceding ACL1in promoter sequences in which the 3' ATGG or ATG sequence is deleted.

In a further embodiment, the promoter comprises a nucleic acid sequence of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to an TEF1in promoter of any one of SEQ ID NOs:115-122. In some embodiments, the promoter comprises any one of the preceding TEF1in promoter sequences in which the 3' ATGG or ATG sequence is deleted. The upstream sequence of translational elongation factor EF-1 alpha gene (TEF1, −1000~1) showed 81% promoter activity of that of glyceraldehyde-3-phosphate dehydrogenase promoter (GPD1 promoter). The incorporation of intron 1 and 2 of TEF1 (TEF1in promoter) enhanced its promoter activity by 2 folds, reaching 1.2~3.0 folds of that of GPD1 promoter when cultured in the rich medium, yeast extract-peptone-dextrose broth (YPD) for 1 day. The promoter TEF1in performed slightly lower than GPD1 promoter during lipid accumulation phase, where its promoter activity was 91% of that of GPD1 promoter when cultured in GJ2013 for 2 days. Serial truncation analysis and mutagenesis analysis revealed that the 1.1 kb TEF1in promoter showed the best performance.

In a further embodiment, the promoter comprises a nucleotide sequence, wherein the nucleotide sequence is hybridizable under stringent conditions with a DNA molecule comprising the full complement of any one of SEQ ID NOs:74-77, 79-83, 85-85-96, 97 or 115-122.

Database searches and homology searches of genome and nucleotide databases can be used to identify similar promoters based on the alignment of nucleotides using algorithms or computer programs and these techniques well known to those of skill in the art.

In some embodiments, the present invention relates to an isolated promoter or a promoter as described herein. In other embodiments, the present invention relates to a nucleic acid comprising an isolated promoter or a promoter described herein.

Nucleic Acid Constructs

In an aspect, the present invention provides a nucleic acid construct (also referred to as a recombinant DNA construct or sometimes simply as a nucleic acid) useful for expressing a nucleic acid of interest in a yeast or fungi, or in a yeast or fungal cell. In some embodiments, the nucleic acid construct comprises a promoter described herein operably linked to a nucleic acid of interest.

In one embodiment, the nucleic acid construct comprises an promoter, as described herein, operably linked to a heterologous polynucleotide. In another embodiment, the polynucleotide is operably linked to a transcription terminator. In a further embodiment, the transcription terminator is operable in a yeast or fungal species. Transcription terminators of protein encoding genes are typically located downstream (3') of the gene, after the stop codon (TGA, TAG or TAA). Transcription terminators play an important role in the processing and stability of RNA as well as in translation. Most, but not all transcription terminators, contain a polyadenylation sequence or cleavage site.

In some embodiments, the nucleic acid of interest encodes a protein useful for the production of biobased chemicals with broad applications. In some embodiments, the biobased chemicals may be fatty acids, fatty alcohols, terpenes and carotenoids. In other embodiments, the nucleic acid of interest encodes terpene synthases, P450 cytochrome oxidases, fatty acid reductases, fatty acid-CoA reductases.

In some embodiments, the coding sequence of the nucleic acid of interest is naturally occurring. In other embodiments, the coding sequence of the nucleic acid of interest is modified to contain codons preferred by the yeast or fungi. In one embodiment, the coding sequence is one that is either naturally existent or artificially created and contains at least about 60% GC. In another embodiment, the coding sequence is one that is either naturally existent or artificially created and contains about 70% GC. In a further embodiment, the coding sequence is one that is either naturally existent or artificially created and contains about 75% GC. In one embodiment, at least about 70% of the codon triplets of such coding sequences end with C or G. In another embodiment, more than about 80% of the codon triplets of such coding sequences end with C or G. In one embodiment, the coding sequence for a selectable marker is at least 60% GC, preferably about 70% GC and most preferably about 75% GC in which at least 70% of the codon triplets end with C or G, preferably more than 80% of the codon triplets end with C or G. In one embodiment, such coding sequences are composed of UCG codons in at least about 40% of the total serine (Ser) residues.

The nucleic acid construct may include other transcriptional regulatory regions as are well known in the art.

In some embodiments, the nucleic acid construct further comprises a selectable marker. Selectable markers are well known to the skilled artisan as are nucleic acid constructs incorporating such selectable markers and promoters to drive their expression, such as described in International Patent Application Publication No. WO 2012/169969. Any suitable promoter operably linked to any suitable selectable marker can be used in the present invention. In some embodiments, examples of suitable promoters for use with selectable markers include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidyl-prolyl isomerase (PPI), acetyl-CoA carboxylase (ACC) or transaldolase.

In one embodiment, the coding sequence for the selectable marker is one that is either naturally existent or artificially created and contains at least about 60% GC. In a second embodiment, the coding sequence for the selectable marker is one that is either naturally existent or artificially created and contains about 70% GC. In a third embodiment, the coding sequence for the selectable marker is one that is either naturally existent or artificially created and contains about 75% GC. In one embodiment, at least about 70% of the codon triplets of such coding sequences end with C or G. In another embodiment, more than about 80% of the codon triplets of such coding sequences end with C or G. In one embodiment, the coding sequence for a selectable marker is at least 60% GC, preferably about 70% GC and most preferably about 75% GC in which at least 70% of the codon triplets end with C or G, preferably more than 80% of the codon triplets end with C or G. In one embodiment, such coding sequences are composed of UCG codons in at least about 40% of the total serine (Ser) residues.

In some embodiments, the selectable marker is part of a recombination marker free system. In one embodiment, the recombination marker free system is a Cre-lox recombination marker free system, such as described by Zuo et al. [38]. Such a system is useful for producing selection marker free transgenic yeast or fungi. In some embodiments, the recombination marker free system is positioned between the promoter described herein and the one or more nucleic acid fragments. In this embodiment, the removal of the marker gene by the recombination event places the promoter in operable linkage with the nucleic acid of interest as described herein.

In preparing the nucleic acid construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

In a further aspect, the present invention provides a yeast or fungal cell comprising the nucleic acid construct described herein. In one embodiment, the fungal cell is a cell of a species of the *Rhodosporidium* genus. In another embodiment, the fungal cell is a cell of a species of the *Rhodotorula* genus. In some embodiments, the nucleic acid construct is stably integrated in the genome of the fungal cell. In other embodiments, the fungal cell is part of a composition also comprising a culture medium.

One or more nucleic acid constructs may be introduced directly into a fungal cell using techniques such as electroporation, DNA particle bombardment. Alternatively, the nucleic acid constructs may be combined with suitable T-DNA flanking regions and introduced into an *Agrobacterium tumefaciens* host, which will deliver the gene cassette into the fungal genome. Thus, any method, which provides for effective transformation/transfection of fungi may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

It may be useful to generate a number of individual transformed fungi with any recombinant construct in order to recover fungi free from any positional effects. It may also be preferable to select fungi that contain more than one copy of the introduced nucleic construct such that high levels of expression of the polynucleotide are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

In an additional aspect, the present invention provides a method of preparing and using a fungal species comprising the nucleic acid construct described herein. In one embodiment, a method of preparing the fungal species comprises introducing the nucleic acid construct described herein into a fungal cell and selecting a fungal cell that has the nucleic acid construct stably integrated in its genome. In another embodiment, a method of using the fungal species comprises culturing the fungal species comprising the nucleic acid construct described herein in a medium conventionally used for culturing yeast or fungal species or as described herein, such as GJm2 medium, GJm2 medium or Li2006 medium.

In some embodiments, transformed fungi are transferred to standard growing media (e.g., solid or liquid nutrient media, grain, vermiculite, compost, peat, wood, wood sawdust, straw, etc.) and grown or cultivated in a manner known to the skilled artisan. In one embodiment, the media is minAB medium or minAB medium modified to omit carbon source and $NH_4NO_3$.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods for Examples 2-6

Strains, media and culture conditions: *R. toruloides* strain ATCC 10657 was used as the wild-type strain unless indicated otherwise. *R. toruloides* quadruple disruption mutant dlad (Δdga1Δlro1Δare1Δdga3) was generated by serially deleted the four diacylglycerol acyltransferase genes such as DGA1, LRO1, ARE1 and DGA3 in the nonhomologous end joining-deficient host Δku70e [7], through homologous recombination.

*R. toruloides* was cultured at 28° C. in YPD broth (1% yeast extract, 2% peptone, 2% glucose) or on solid potato-dextrose agar (PDA). *A. tumefaciens* was grown at 28° C. in either liquid or solid 2YT medium (1.6% tryptone, 1% yeast extract, 0.5% NaCl). *E. coli* XL1-Blue was cultured in Luria-Bertani (LB) broth or on LB agar and used for routine DNA manipulation.

Luciferease gene reporter strains in *R. toruloides* were cultured in medium MinRL3 unless indicated otherwise. Medium MinRL3 contains (per liter) 70 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$. The medium pH was adjusted to 6.1. Medium MinRL2 contains the same compositions as MinRL3 except the enhanced glucose concentration to 100 g/L. The promoter activity were determined according to the luciferase activity in the yeast strains during lipid accumulation stage conducted at 30° C., 250 rpm for 5 days unless indicated otherwise.

Some reporter strains were also cultured in lipid production medium "Li2006" [32], medium "GJm" and "GJm2" [33] with modifications where initial glucose level was increased to 70, 100 and 70 g/L, respectively. Briefly, medium Li2006 (per liter) contains 70 g/L glucose, 0.1 g $(NH_4)_2SO_4$, 0.75 g yeast extract, 1.5 g $MgSO_4.7H_2O$, 0.4 g $KH_2PO_4$, $1.91\times10^{-6}$ mol $ZnSO_4$, 1.50 mmol $CaCl_2$, $1.22\times10^{-4}$ mmol $MnCl_2$, and $1.00\times10^{-4}$ mmol $CuSO_4$. Medium GJm (per litre) contains 70 g glucose, 0.4 g $KH_2PO_4$, 1.5 g $MgSO_4.7H_2O$, 10 ml TE solution, pH6.0. TE solution (per liter) contains 4.0 g $CaCl_2.2H_2O$, 0.55 g $FeSO_4.7H_2O$, 0.52 g citric acid.$H_2O$, 0.1 g $ZnSO_4.7H_2O$, 0.076 g $MnSO_4.H_2O$, 0.1 ml smoked $H_2SO_4$[34].

Some reporter strains were cultured in terpenoid production medium "Y4" [35] with some modifications. Briefly, medium Y4 (per liter) contains 100 g/L glucose, 15.7 g/L peptone, 15.7 g/L yeast extract, 12 g/L $(NH4)_2SO_4$, 1 g/L $KH_2PO_4$, 1.5 g/L $MgSO_4.7H2O$ (pH5.5).

Plasmid construction: Oligonucleotides used are listed in Table 1. All DNA restriction and modification enzymes were sourced from New England Biolabs (NEB, USA). Plasmid pKCL2 (FIG. 9) is a pPZP200 derivative [36] that allows efficient knock-in of reporter gene cassette at the CAR2 locus, consisting of a hygromycin resistant cassette ($P_{GPD1-3}$:HPT-3:$T_{SV40}$) and a luciferase reporter cassette ($P_{GPD1}$::RtLUC2:$T_{35S}$) flanking with CAR2 locus sequence [29]. $P_{GPD1-3}$ and $P_{GPD1}$ are the glyceraldehyde 3-phosphate promoter derived from *R. graminis* WP 1 and *R. toruloides* ATCC 10657, with GenBank accession number of JQ806386 and JN208861, respectively [6]. HPT-3 (JQ806387) and RtLUC2 (KR258785) are the codon-optimized synthetic genes encoding the *E. coli* hygromycin phosphotransferase and firefly luciferase (Luc2, ACH53166.1), respectively [6].

TABLE 1

Sequences of Oligonucleotides

| Name | Sequence (5'-3') (SEQ ID NO:) | Restriction Site |
| --- | --- | --- |
| SV40R | TTTccgcggTCGAATTTCCCCGATCGTTCA (8) | $T_{SV40}$ |
| LUC2U | GAGTCGCTCACCTACTGCATC (9) | RtLUC2 |
| ACC1U1 | GAAGGCGGGGGTTCTCGGAAG (10) | ACC1 |
| PLN1U1 | GACGAGGTCATCCGCGAG (11) | PLN1 5'UTR |
| PLN1L1 | GACCAGCTCTACCAGCGCATCAC (12) | PLN1 3'UTR |
| CRP79L1 | TCGCCCTCCTCCCCTGCTCGCAAAT (13) | CRP79 |
| Rt232Sf | TTTactagtGGTCGCTTCTTTCCTCGCAG (14) | ACC1/ACC1in |
| Rt233Nr | TTTccatggGAAGTGAAGTTGGGGAACG (15) | ACC1 |
| Rt310Nr | TTTccatggAGAACCTGTCGTCGCATGA (16) | ACC1in |
| Rt238Sf | TTTactagtCGCGCCTTGTCCGCTTC (17) | ACC1in7 |
| Rt239Sf | TTTactagtCTTCAGAAGGGATGGGAGGAG (18) | ACC1in6 |
| Rt240Sf | TTTactagtCTGGCACGCCGTCGAGGAC (19) | ACC1in5 |
| Rt241Sf | TTTactagtGACCCGGATTACTCGAGCATC (20) | ACC1in4 |
| Rt242Sf | TTTactagtGCTCAAGCGAGCCGATACAG (21) | ACC1in3 |
| Rt243Sf | TTTactagtTGCGGGAGTTGTTGGACAC (22) | ACC1in2 |
| Rt373fusion | GATCGGAAGTGAAGTTGGGGAAC (23) | ACC1int |
| Rt374fusion | TTCGTTCCCCAACTTCACTTCCGATCCCGTGCGTCGCCTCCCTTTC (24) | ACC1int |
| Rt359Sf | TTTACTAGTTCGACTTGTCTTCCTCCGCGA (25) | DUR1/DRU1in |
| Rt360Nr | TTTCCATGGCGAAAGAGGGATGTGAG (26) | DUR1 |
| Rt424Nr | TTTCCATGGAGAAGAGGTTCTGCGCGGA (27) | DUR1in |
| Rt363Sf | TTTACTAGTCTGTGATGCTAGGTGTCGATC (28) | ACL1/ACL1in |
| Rt364Nr | TTTCCATGGCTGCTGCGTTTCCTGGTAC (29) | ACL1 |
| Rt365Nr | TTTCCATGGCGTCGTACTCGCGGATG (30) | ACL1in |
| Rt369Sf | TTTACTAGTGAACTCGACTCATTACGGGAG (31) | FAS1/FAS1in |
| Rt370Nr | TTTCCATGGTGTGCGGTATTCGACGAGTTTG (32) | FAS1 |
| Rt371Nr-1 | TTTCCATGGAGTAGTGCTGTCCGCGCAGA (33) | FAS1in |
| Rt361Sf | TTTACTAGTCTCTAGCCTACGACCGCCTC (34) | FAT1 |
| Rt362Nr | TTTCCATGGTAGCGAGTCGTTCTCTGCAG (35) | FAT1 |
| Rt359Sf | TTTACTAGTTCGACTTGTCTTCCTCCGCGA (36) | DUR1/DUR1in |
| Rt360Nr | TTTCCATGGCGAAAGAGGGATGTGAG (37) | DUR1 |
| Rt424Nr | TTTCCATGGAGAAGAGGTTCTGCGCGGA (38) | DUR1in |
| Rt366Sf | TTTACTAGTCACGCCTCTGTGACTCGGTAC (39) | PLN1/PLN1in |
| Rt367Nr | TTTCCATGGCGTGCGAGTGTGCGTGCGA (40) | PLN1 |
| Rt368Nr | TTTCCATGGGTAGTCCGACACCTGCG (41) | PLN1in |
| Rt403 | AGCTTGGATCCATGTCGCGTAGGCTCGTTCGG (42) | PLN1int3 |
| Rt404 | TTAACGCCGAATTGAATTCGGAGGTTTTTCGACGCACGTGAGTCG (43) | PLN1int3 |

TABLE 1-continued

Sequences of Oligonucleotides

| Name | Sequence (5'-3') (SEQ ID NO:) | Restriction Site |
|---|---|---|
| Rt405 | ACGCGACATGGATCCAAGCTCAAGCTAAGCTGATCCTACC (44) | PLN1int3 |
| Rt406 | GGCGCCCATGCTGAATTAACGCCGAATTGAATTCGCGCG (45) | PLN1int3 |
| Rt407 | CCTTGCGTATAATATTTGCCCACGAGGGACTTGAGATGTGA (46) | |
| Rt408 | GTTAATTCAGCATGGGCGCCCGCGC (47) | |
| Rt411m | CACGCACACTCGCACGCAATCGCCACCGTCAACGAGAAGCAGC (48) | PLN1int1 |
| Rt412m | GCTGCTTCTCGTTGACGGTGGCGATTGCGTGCGAGTGTGCGTG (49) | PLN1int1 |
| Rt413m | AGCACACACGCAGGTGTCGGCCGCCACCATGGAGGACGCCAAGAAC (50) | PLN1int2 |
| Rt414m | GTTCTTGGCGTCCTCCATGGTGGCGGCCGACACCTGCGTGTGTGCT (51) | PLN1int2 |
| Rt415S | TTTACTAGTTTTTCCCGCTCTGCCCTC (52) | PLN1int3 |
| Rt416S | TTTACTAGTACGAACAACAACGAGCCACACA (53) | PLN1int4 |
| Rt417S | TTTACTAGTGCTCACCCTTATCGTCACTC (54) | PLN1int5 |
| Rt418S | TTTACTAGTGCCTCACTCCCTCTCTCGCT (55) | PLN1int6 |
| Rt419S | TTTACTAGTACAAGCACAACACACGGCAC (56) | PLN1int7 |
| Rt420m | ACCGCCATCCACCGCGTGCGGTGAAACCCGCTCACCCGTT (57) | PLN1int8 |
| Rt421m | AACGGGTGAGCGGGTTTCACCGCACGCGGTGGATGGCGGT (58) | PLN1int8 |

All promoter sequences were amplified using *R. toruloides* genomic DNA as the template. Upstream sequence of ACL1 (−1000~−1 and −1000~+167, $P_{ACL1}$ and $P_{ACL1in}$, respectively) was amplified using oligo pair Rt363Sf/Rt364Nr and Rt363Sf/Rt365Nr, respectively. The SpeI-NcoI cut PCR products were inserted to the same sites of vector pKCL2 to create plasmid pKCLAL1 and pKCLAL2 respectively. Upstream sequence of FAS1 (−1001~−1 and −1001~+271 for $P_{FAS1}$ and $P_{FAS1in}$, respectively) was amplified using oligo pair Rt369Sf/Rt370Nr and Rt369Sf/Rt371Nr, respectively. The SpeI-NcoI cut PCR products were inserted to the same sites of pKCL2 to create pKCLF3 and pKCLF4, respectively. Upstream sequence of FAT1 (−1003~−1, $P_{FAT1}$) was amplified using oligo pair Rt361Sf/Rt362Nr, and the SpeI-NcoI cut PCR products were inserted to the same sites of pKCL2 to create pKCLF5. Upstream sequence of DUR1 (−493~−1 and −493~+627, $P_{DUR1}$ and $P_{DUR1in}$, respectively) was amplified using oligo pair Rt359Sf/Rt360Nr and Rt359Sf/Rt424Nr, respectively. The SpeI-NcoI cut PCR products were inserted to the same sites of pKCL2 to create pKCLDU1 and pKCLDU2, respectively.

Upstream sequence of ACC1 (−1501~−1 and −1501~+91, $P_{ACC1}$ and $P_{ACC1in}$, respectively) was amplified using oligo pair Rt232Sf/Rt233Nr and Rt232Sf/Rt310Nr, respectively. The SpeI-NcoI cut PCR products were inserted to the same sites of pKCL2 to create pKCLA1 and pKCLA2, respectively. For serial deletion analysis, ACC1in promoter $P_{ACC1in2}$, $P_{ACC1in3}$, $P_{ACC1in4}$, $P_{ACC1in5}$, $P_{ACC1in6}$ and $P_{ACC1in7}$ from different positions (−1204, −995, −807, −601, −407 and −201 from the first ATG of CDS respectively) was amplified using oligo pair Rt243Sf/Rt310Nr, Rt242Sf/Rt310Nr, Rt241Sf/Rt310Nr, Rt240Sf/Rt310Nr, Rt239Sf/Rt310Nr and Rt238Sf/Rt310Nr, respectively. The PCR products were double digested with SpeI and NcoI and inserted to the same sites of pKCL2 to create plasmid pKCLA3, pKCLA4, pKCLA5, pKCLA6, pKCLA7 and pKCLA8, respectively. For create mutation in the original translational start codon in ACC1, DNA fragments ACC1intL and ACC1intR were amplified using the template of plasmid pKCLA8 and oligo pair SV4OR/Rt373fusion and Rt374fusion/LUC2U, respectively. Fusion PCR was then performed using above gel-purified PCR products (380 bp and 286 bp, respectively) and oligos Rt238Sf and Rt310Nr. The resultant PCR products (0.3 kb) were double digested with SpeI and NcoI and inserted to the same sites of pKCL2 to create plasmid pKCLA81.

Upstream sequence of PLN1 (−362 to −1 and −362 to +152 for $P_{PLN1}$ and $P_{PLN1in}$, respectively) was amplified using oligo pair Rt366Sf/Rt367Nr and Rt366Sf/Rt368Nr, respectively. The SpeI-NcoI PCR products (0.4 kb and 0.5 kb, respectively) were inserted to the same sites of pKCL2 to create pKCLP3 and pKCLP4, respectively. For serial deletion analysis, PLN1in promoter $P_{PLN1int3}$, $P_{PLN1int4}$, $P_{PLN1int5}$, $P_{PLN1int6}$ and $P_{PLN1int7}$ from different upstream positions (−223, −180, −106, −70 and −43, respectively) was amplified using oligo pair Rt415Sf/Rt368Nr, Rt416Sf/Rt368Nr, Rt417Sf/Rt368Nr, Rt418Sf/Rt368Nr and Rt419Sf/Rt368Nr, respectively. The resultant PCR products were individually double digested with SpeI and NcoI and inserted to the same sites of pKCL2 to create plasmid pKCLP43, pKCLP44, pKCLP45, pKCLP46 and pKCLP47, respectively.

To make mutation in the original translational start codon of PLN1, DNA fragment PLN1int1L and PLN1int1R were amplified using the template of plasmid pKCLP4 and oligo pair SV40R/Rt412m and Rt411m/LUC2U, respectively. The plasmid pKCLP41 was created by three-fragment Gibson assembly, including the SpeI-NcoI double digested pKCLP4 vector (12.5 kb) and above two gel-purified PCR products, i.e. PLN1int1L and PLN1int1R (713 bp and 341 bp, respectively), according to the supplier's instruction (NEBuilder kit, NEB, England). To delete the ct box #4 in promoter PLN1in (FIG. 5A), DNA fragment PLN1int8L and PLN1int8R were amplified using the template of plasmid pKCLP4 and oligo pair SV40R/Rt421m and Rt420m/LUC2U, respectively. As in construction of pKCLP41, the plasmid pKCLP48 was created by three-fragment Gibson assembly, including the SpeI-NcoI double digested pKCLP4 vector (12.5 kb) and above two gel-purified PCR products, PLN1int8L and PLN1int8R PCR fragments (808 bp and 269 bp, respectively).

*Agrobacterium tumefaciens*-mediated transformation: The binary vectors were electroporated into *A. tumefaciens* AGL1 (2.5 kV, 25 μF, 400Ω) and subsequently selected with 2YT agar medium supplemented with streptomycin (100 μg/ml). Fungi transformation via ATMT was performed as described previously [6].

Isolation of genomic and total RNA: Genomic DNA and RNA of *R. toruloides* was extracted as described previously [6]. The concentration and purity of the extracted DNA and RNA were analyzed by NanoDrop® ND-1000 Spectrophotometer (Nanodrop Technologies, USA) and agarose gel electrophoresis.

Gene annotation in *R. toruloides*: Based on the very high sequence homology between *R. toruloides* ATCC 10657 and *R. glutinis* ATCC 204091, genome database of *R. glutinis* ATCC 204091 was used as reference unless indicated otherwise. *Saccharomyces cerevisiae* and *Yarrowia lipolytica* proteins were usually used as the queries for BLAST searches in *Rhodotorula glutinis* ATCC 204091 genome database. The precise gene and mRNA sequences were further identified using 5' and 3' RACE analyses coupled with RT-PCR.

Rapid amplification of cDNA ends (RACE): The 5' and 3' end of target cDNA sequences were obtained by 5' RACE and 3' RACE using BD SMARTer™ RACE cDNA Amplification Kit (Clontech, Calif., USA) according to the manufacturer's instruction. Oligos for 5' RACE and 3' RACE were listed in Table 1. The full-length cDNAs was amplified by reverse transcription PCR using DNase I-treated total RNA as the template and specific oligos as listed in Table 1.

Reporter assay: Binary T-DNA vectors were electroporated into *Agrobacterium tumefaciens* AGL2 and *A. tumefaciens*-mediated transformation (ATMT) of *R. toruloides* was performed as previously described [6]. Strains bearing the knock-in T-DNA at the CAR2 locus were identified by the albino phenotype followed by confirmation with Southern blotting.

Luciferase reporter strain was cultured in YPD broth to mid-exponential phase. Cells were washed twice with water and inoculated to the indicated medium at an optical density (OD$_{600}$) of 0.5 and cultured at 30° C. with agitation (250 rpm). Luciferase activity was determined by one-step measurement method as described previously [37] with some modifications. Briefly, cell culture (10 μl) was mixed with 85 μl of PBS buffer (pH7.4) and loaded into a well of Fluoro-Nunc 96-well plate (Thermo Fisher Scientific, Langenselbold, Germany) for measurement of bioluminescence. Cell density was measured at OD of 600 nm with 10-20 fold dilution of cell culture in PBS buffer to a final volume of 100 μl, and loaded to a well of 96-well flat-bottom transparent plate (Nunc, Roskilde, Denmark). All data was measured and acquired with the Tecan Infinite M200 plate reader coupled with the iCycler version 3.0 software (Tecan, Salzburg, Austria). Cell density was measured at OD of 600 nm and luminescent values were measured after mixed with 5 μl of 10 mM D-luciferin (DMSO solution, catalog No. L9504, Sigma-Aldrich). The relative promoter activity (RPA) was calculated by normalization against that of GPD1 promoter.

Example 2

Characterization of the Genes Involved in Lipid Accumulation Process

Genomic sequences for ACC1, ACL1, FAS1, FAT1, DUR1 and PLN1 were identified by database search against public database as well as in-house EST and genome database for *R. toruloides* or *R. glutinis* strains (see Methods). ACC1, ACL1, FAS1, FAT1, DUR1 and PLN1 gene was found located in genome scaffold No. 18, 9, 18, 9, 25 and 10, respectively in the genome of *R. glutinis* ATCC 204091. 5' and 3'; RACE analyses or search of in-house EST database revealed that 5'UTR is 150 nt, 179 nt, 142 nt (RNA-seq data), 61 nt (RNA-seq data), 303 nt (RNAseq data) and 194 nt in length, respectively. Notably, the 5'UTRs of both FAS1 and PLN1 mRNA were interrupted by an intron in the respective genomic sequence (FIGS. 1C and 1F, respectively). Detailed information on the structure of the genes is shown in Table 2.

TABLE 2

Gene Annotations

| Gene | CDS Length (nt) | Scaffold No. | 5'LTR (nt) | 3'UTR (nt) | Exons | Protein (aa) |
|------|-----------------|--------------|------------|------------|-------|--------------|
| DUR1 | 4446 | 25 | 303$^b$ | 109$^b$ | 12 | 1239 |
| FAT1 | 2860 | 9 | 61$^b$ | 105$^b$ | 14 | 639 |
| FAS1 | 9628 | 18 | 142$^{ab}$ | 101$^b$ | 16 | 2928 |
| ACL1 | 4417 | 9 | 178$^b$ | 216 | 10 | 1157 |
| ACC1 | 7347 | 18 | 150 | 187$^b$ | 11 | 2232 |
| PLN1 | 1256 | 10 | 115$^{ab}$ | 230$^b$ | 7 | |

Example 3

Analysis of Promoter by Luciferase Reporter Assay

Although regulatory elements for gene transcription in eukaryotes are usually contained within the region preceding the transcriptional start site, exceptions have been found, eg the DAO1 gene of *R. toruloides* and FBA1 gene of *Y. lypolitica* [28, 29]. The discrepancy between the abundant protein level [4] and weak promoter activity of the isolated upstream DNA sequence of ACC1 gene [11] lead us to speculate the intronic sequence might play a major role. Therefore, the upstream DNA sequence for DUR1, FAS1, ACC1 and PLN1 were fused to a luciferase reporter gene (RtLUC2, GenBank accession no. KR258785) in two versions, one with intron(s) and the other without intron(s) except that of FAT1. The ranges of the promoters were shown in FIGS. 1A-1F. The reporter gene was flanked with homologous sequences of CAR2 genome locus as previously reported and can be inserted into the CAR2 locus site-specifically by homologous recombination, eliminating variation of reporter activity resulted from positional effect [30].

Figure 3:
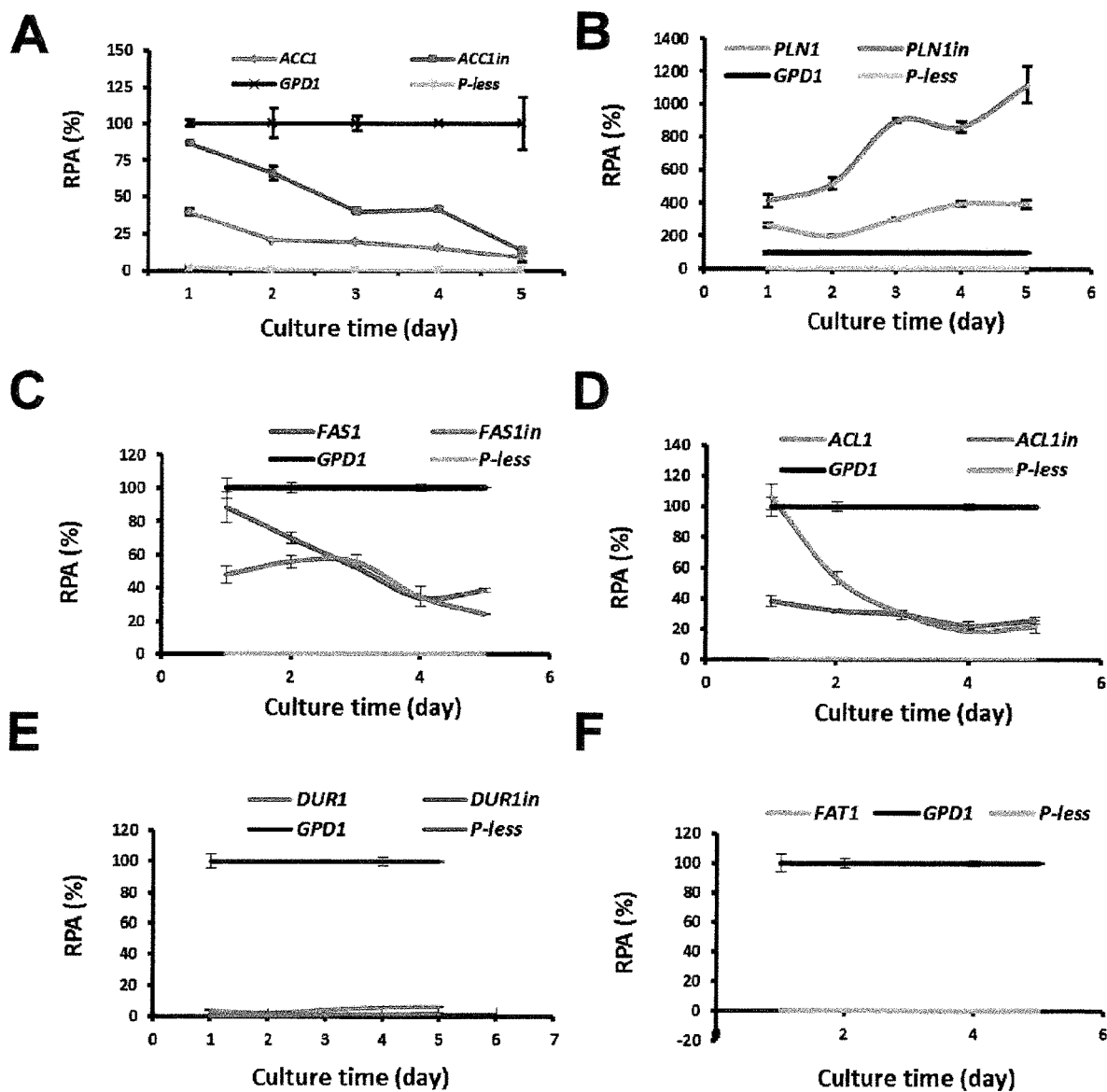
FIGS. 3A-3F show the comparisons of promoter activity.

Consistent with our previous result [11], the 1504 nt intron-less upstream sequence of ACC1 gene (SEQ ID NO:59) showed little activity as determined with luciferase reporter assay. In contrast, inclusion of intron 1 (SEQ ID NO:60) dramatically enhanced the promoter activity (FIG. 2B; FIG. 3A).

Notably, PLN1 promoter (−362 to +3; SEQ ID NO:61) showed 2-4-fold higher activity than GPD1 promoter, which is usually one of the strongest promoters in fungi (FIG. 3B). Surprisingly, PLN1in containing of both intron 1 and intron 2 sequence ($P_{PLN1in}$, −362 to +155; SEQ ID NO:62) displayed much higher activity, reaching up to 11 times that of GPD1 promoter. (FIG. 3B).

The activity pattern of FAS1 and ACL1 promoters share strong similarity (FIGS. 3C and 3D). The intron 1 of both promoters showed repressing effect (SEQ ID NOs:63, 64, 65, 66) during the initial stage of culture as the intron-less promoters showed higher activity. The repressing effect disappeared after day 3, concomitant with lipid accumulation. Thus, the intron-containing FAS1 and ACL1 promoters are useful to delay expression of gene of interest during lipid accumulation stage.

On the other hand, DUR1, DUR1in and FAT1 (SEQ ID NOs:67, 68, 69) promoters all displayed weak activity (FIGS. 3E and 3F).

Example 4

Further Characterization of ACC1in and PLN1in Promoters

Nested deletion analysis revealed that the length of upstream sequence of ACC1 gene drastically influenced promoter activity. The "−201 Acc1in" fragment (from −201 to +95 nt from first ATG; SEQ ID NO:70) was about 5 fold stronger the full length ACC1in fragment, reaching about 80% of GPD1 promoter (FIG. 3B). The "−995 ACC1in" fragment (from −995 to +95 nt; SEQ ID NO:71) ranked $2^{nd}$ in reporter activity.

GC content analysis at BiologicsCorp (http colon slash slash www dot biologicscorp dot corn slash tools slash GCContent) revealed two higher GC regions located at −66~−47 and −30~+43. Notably, a 14-nt GC-rich stretch (GGCGGGCCCGCGCC (SEQ ID NO:72), GC content 100%) was be found within intron 1 (+28~+41, FIG. 4C). Because the protein expressed with the ACC1in promoter will contain a four-aa peptide (MPFS; SEQ ID NO:73) derived from N-terminus of Acc1 (FIG. 3A), the native translational start codon of ACC1in promoter was mutated to ATC and the sequence CTGGCG in exon 2 was changed to CCATGG so that protein translation will start from this created NcoI site (FIG. 4A). Lucifereuse assay with this modified fragment (SEQ ID NO:74) did not significantly change the promoter activity (FIG. 4D).

Similarly, nested deletions were made for the PLN1in promoter. The breakpoint of the fragment was made so that the potential function of four ct-rich cis-acting elements could be tested. Similar to the ACC1in promoter, the original translation start codon was changed to ATC and a new translation initiation codon was created in exon 3 (FIG. 4B). As expected this modifications (SEQ ID NO:6; $P_{PLN1int1}$) did not significantly affect the promoter activity. In addition, promoter activity steadily decreased as the length of the fragment shortened. (FIGS. 5A and 5B). ct box #4 (nucleotides +075 to +100 in FIG. 4B) within the intron 2 was found critical for strong promoter function, deletion of which resulted in 98.1% reduction of reporter activity and ct box #2 (nucleotides −105 to −81 in FIG. 4B) also appeared to play a significant role (FIG. 5B).

FAS1in and ACL1in are similarly modified to change the original ATG start codon to ATC and to add a new ATG start codon to produce promoters having SEQ ID NO:76 and SEQ ID NO:80, respectively.

Example 5

Activity of PLN1in Promoter in Various Media

Figure 6:
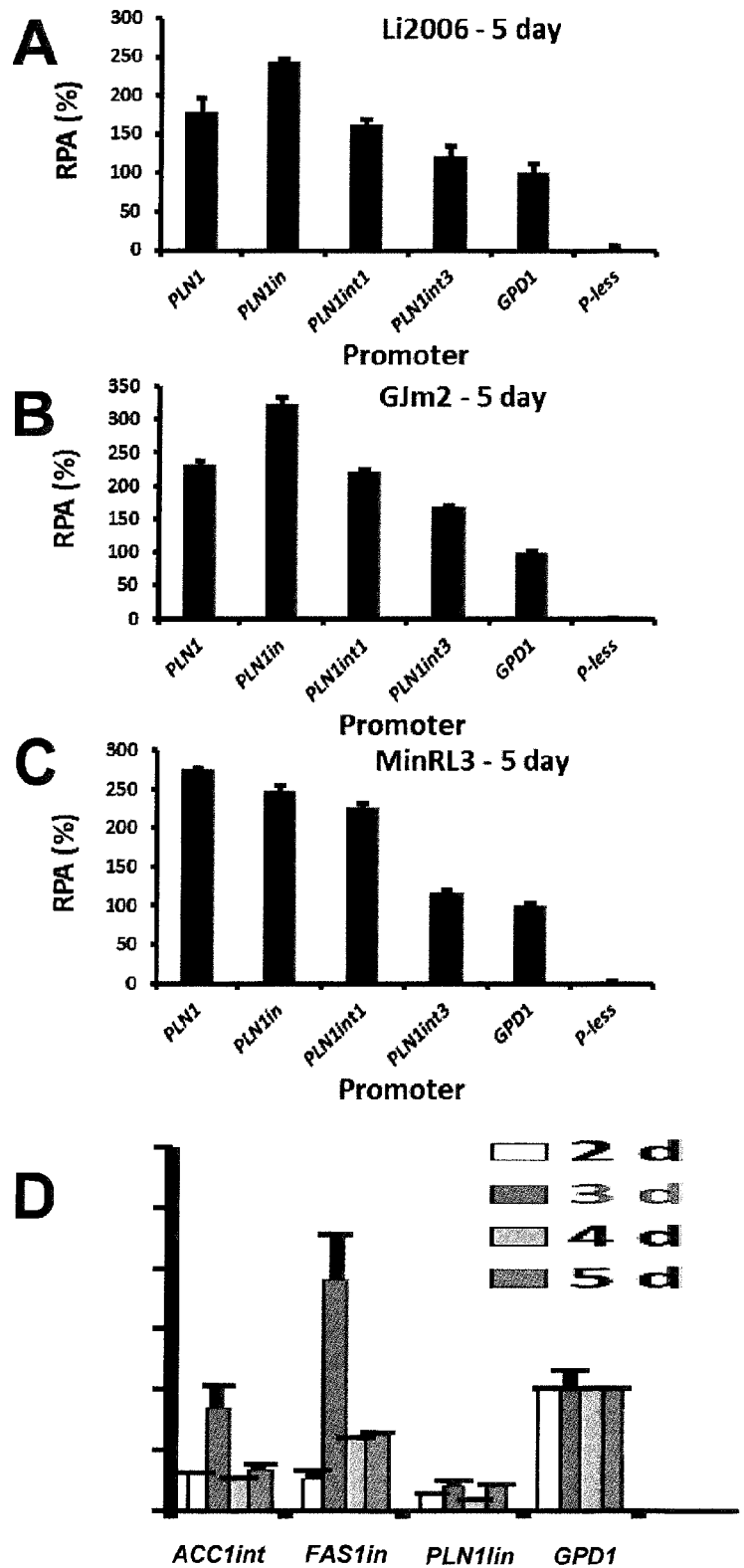
FIGS. 6A-6D show comparison of promoter activities in different media. *R. toruloides* luciferase gene reporter strain for PLN1 (SEQ ID NO: 4), PLN1in (SEQ ID NO:5), PLN1int1 (SEQ ID NO:6) and PLN1int3 (−223 to +155; See FIG. 5A) was cultured in Medium Li2006 (FIG. 6A), Medium GJm2 (FIG. 6B), Medium MinRL3 (FIG. 6C), or Y4 medium (FIG. 6D). Relative promoter activity was determined on the 5th day. The activity of GPD1 promoter was set as 100%.
Figure 8:
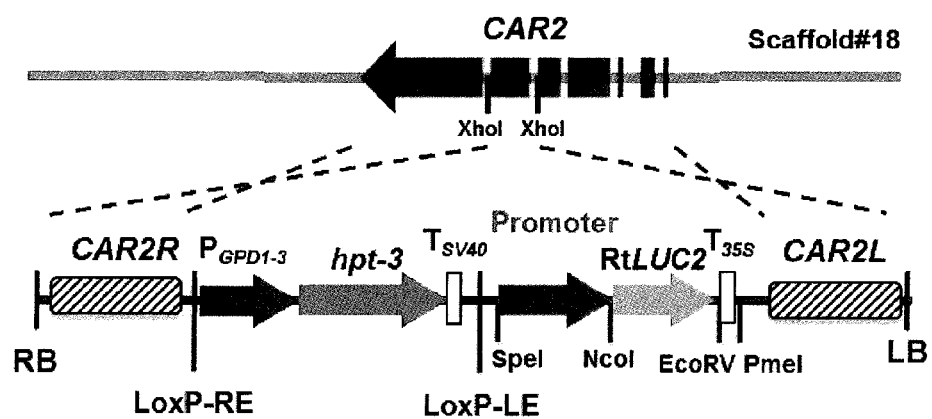
FIG. 8 shows a diagram of luciferase reporter constructs. LB and RB: right and left border of *Agrobacterium* T-DNA; loxP-RE and loxP-LE are the mutant cre recombinase recognition sites; RtLUC2: codon optimized luciferease gene, CAR2R and CAR2L indicate the right and left arm for homologous recombination at CAR2 locus respectively. HPT-3 codon optimized hygromycin resistance gene; "promoter": location of promoters inserted in the reporter assay.

To see if the superior performance of the PLN1in promoter could be replicated in different lipid production media, luciferase reporter strains containing PLN1 (SEQ ID NO:4), PLN1in (SEQ ID NO:5), PLN1int (SEQ ID NO:6) and PLN1int1 fragments (FIG. 5A) were cultured in Li2006 medium, GJm2 medium and MinRL3 medium (refer to material and method for the compositions) for 5 days, where the same concentration of glucose (70 g/L) was used initially. PLN1 and PLN1in exhibited 2-3 folds higher activity compared to GPD1 promoter in all media (FIG. 6). Consistent with earlier observations, promoter PLN1in showed higher strength than the intron-less promoter PLN1 in the medium of Li2006 and GJm2 (~1.4 fold increase each, FIGS. 6A and 6B), although this was not obvious in medium MinRL3 (FIG. 6C). PLN1int1 fragment (SEQ ID NO:6) was slightly weaker than PLN1in fragment, possibly due to the fact that the nucleotide at −3 upstream of the newly created translation initiation was "T" rather than G/A, i.e. the translation codon is located in a less favorable Kozak consensus sequence [31]. Changing C to G at −3 position will correct this problem.

Surprisingly, PLN1in promoter was much weaker in Y4 medium while FAS1in (with ATG to ATC mutation and re-created ATG (SEQ ID NO:76)) and ACC1int promoter (with ATG to ATC mutation and re-created ATG in exon 2 (SEQ ID NO:77)) showed significantly improved activity (FIG. 7D).

Example 6

Activity of Lipid Production Related Promoters in Lipid Deficient Mutant

To evaluate the performances of the above promoters in a non-oil accumulating genetic background, reporter constructs for ACL1int (SEQ ID NO:77), PLN1 (SEQ ID NO:4), PLN1in (SEQ ID NO:5) and PLN1int1 (SEQ ID NO:6) were transformed into a R. toruloides quadruple mutant strain, dlad, in which all 4 diacylglycerol acyltransferases, Dga1, Lro1, Are1 and Dga3, were deleted by homologous recombination. This mutant contains very little TAG (FIGS. 7A and 7B). Reporter strains were cultured in lipid production medium MinRL3 for 5 days and luciferase assays were daily performed. Results revealed the similar promoter performances in the mutant dlad as compared to the wild-type strain (compare FIG. 7C and FIG. 6B). PLN1, PLN1in and PLN1int1 are closely related to lipid accumulation conditions, which are independent of the integrity of the lipid biosynthesis pathway.

Example 7

Materials and Methods for Examples 8-11

DNA construction: Oligonucleotides used are listed in Table 3. All DNA restriction and modification enzymes were sourced from New England Biolabs (NEB, Mass., USA). The sequence fidelity of all constructed plasmids was verified by sequencing.

TABLE 3

Sequences of Oligonucleotides

| Name | Sequence (5'-3') (SEQ ID NO:) | Information |
|---|---|---|
| Rt356Sf | TTTACTAGTGCACGCGAAGCGGTAGAAGC (98) | TEF1, TEF1in(t) |
| Rt357Nr2 | TTTCCATGGATCCCCCCCAGTACACAGTAC (99) | TEF1 |
| Rt358Nr | TTTCCATGGAGTCGACGTGGCCTGCG (100) | TEF1in |
| Rt409m | GTGTACTGGGGGGATAGATCGGCAAG GAAAAGGGACACGT (101) | TEF1inm1 |
| Rt410m | ACGTGTCCCTTTTCCTTGCCGATCTAT CCCCCCAGTACAC (102) | TEF1inm1 |
| Rt437Sf | TTTACTAGTGGCAAACACAGCAACGAC (103) | TEF1int1 |
| Rt438Sf | TTTACTAGTCGTTCTTCGACGTCCGAG (104) | TEF1int2 |
| Rt439Sf | TTTACTAGTGGCTGGGTGTGCGGAG (105) | TEF1int3 |
| Rt440Sf | TTTACTAGTGCACCTCGCGTCAACCCTC (106) | TEF1int4 |

The promoter sequences were amplified using *R. toruloides* genomic DNA as the template unless indicated otherwise. Upstream sequence of TEF1 (−1000~−1) and TEF1in (−1000~+130) (FIG. 9A) was amplified using oligo pair Rt356Sf/Rt357Nr2 and Rt356Sf/Rt358Nr, respectively. The resulting PCR products of TEF1 and TEF1in promoter were double digested with SpeI and NcoI and inserted to the same sites of vector pKCL2 to create plasmid pKCLT1 and pKCLT2, respectively. For serial deletion analysis, TEF1in promoter $P_{TEF1int1}$, $P_{TEF1int2}$, $P_{TEF1int3}$ and $P_{TEF1int4}$ from different upstream positions (−797, −600, −382, and −193, respectively) was amplified using oligo pair Rt437Sf/Rt358Nr, Rt438Sf/Rt358Nr, Rt439Sf/Rt358Nr, and Rt440Sf/Rt358Nr, respectively. The resulting PCR products were double digested with SpeI and NcoI and inserted to the same sites of pKCL2 to create plasmid pKCLT22, pKCLT23, pKCLT24 and pKCLT25, respectively. To make mutation in the original translational start codon of TEF1in promoter (TEF1int1 promoter), similar as PLN1int1 promoter, DNA fragment TEF1intL and TEF1int1R were amplified using the template of plasmid pKCLT2 and oligo pair SV40R/Rt409m and Rt410m/LUC2U, respectively. The plasmid pKCLT21 was created by three-fragment Gibson assembly, including the SpeI-NcoI double digested pKCLT2 vector (12.5 kb) and above two gel-purified PCR products, i.e. TEF1inm1L and TEF1inm1R (1349 bp and 319 bp, respectively), according to the supplier's instruction (NEBuilder kit, NEB, England).

Example 8

Bioinformatics Analysis of TEF1

Genomic sequences for translational elongation factor EF-1 alpha gene (TEF1) was identified by BLAST search against the public database as well as in-house EST and genome database of *R. toruloides* strains [39, 40] using the query of orthologous Tef1p from *Saccharomyces cerevisiae* (Table 4). The putative homolog of TEF1 was found located in the genome sequencing scaffold No. 13 of *R. glutinis* ATCC 204091 (Table 4). Analysis by 5' RACE and transcriptomics showed that the cDNA of TEF1 (SEQ ID NO:112) contains a 5' untranslated region (5'UTR) of 45 nt in length (Table 4, FIGS. 9A and 9B). The genomic sequence is shown in SEQ ID NO:111.

TABLE 4

Gene Annotations

| Gene | Scaffold No. | CDS Length (nt) | 5'UTR (nt) | 3'UTR (nt) | Exon | Protein (aa) | Query [c] |
|---|---|---|---|---|---|---|---|
| ACC1 | 18 | 7,347 | 150 | 187[b] | 11 | 2,232 | YNR016C |
| ACL1 | 9 | 4,417 | 178[b] | 216 | 10 | 1,157 | YALI0E34793g |
| FAS1 | 18 | 9,628 | 142[ab] | 101[b] | 16 | 2,928 | YKL182W |
| FAT1 | 9 | 2,860 | 61[b] | 105[b] | 14 | 639 | YBR041W |
| DUR1 | 25 | 4,446 | 303[b] | 109[b] | 12 | 1,239 | YBR208C |
| PLN1 | 10 | 1,256 | 115[ab] | 230[b] | 7 | 261 | RHTO-05627 |
| TEF1 | 13 | 2,142 | 45[ab] | 252[b] | 10 | 461 | YPR080W |

Example 9

Promoter Analysis

Figure 10:
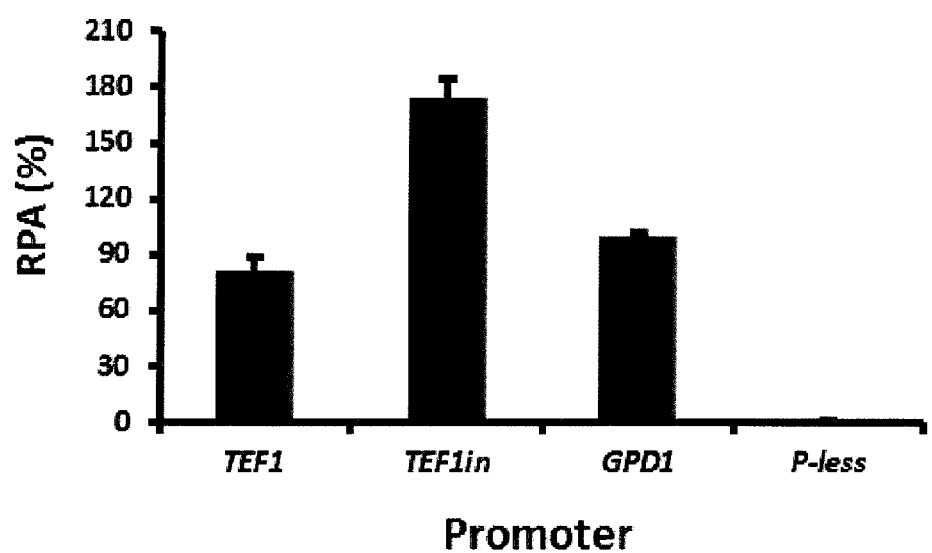
FIG. 10 shows a comparison of promoter strength of TEF1 and TEF1in. All promoter strength was calculated by normalization against that of GPD1 promoter and named as relative promoter activity (RPA). Cells were cultured in YPD medium for 1 day and assayed by luciferase activities.

Upstream DNA sequence of TEF1 was amplified by PCR in two versions, with or without the intronic sequence (FIGS. 9A and 9B), and fused to the codon-optimized luciferase reporter gene RtLUC2 (GenBank accession number KR258785) [29] in the binary vector pKCL2. Against the intron-less TEF1 promoter (−1000~−1), the intronic TEF1in promoter (−100 to +130) yielded significantly higher luciferase activity when cultured in the rich media like YPD broth (FIG. 10), reaching 1.7 fold of that of GPD1 promoter after cultured for 1 day (FIG. 10), while the TEF1 promoter behaved only 81% of promoter strength of GPD1 promoter. Thus, the TEF1in promoter is able to drive strong gene expression, and the $2^{nd}$ intron of TEF1 can behave as an enhancer of 2 fold enhancement in promoter strength.

Example 10

Truncation Analysis

Figure 11A:
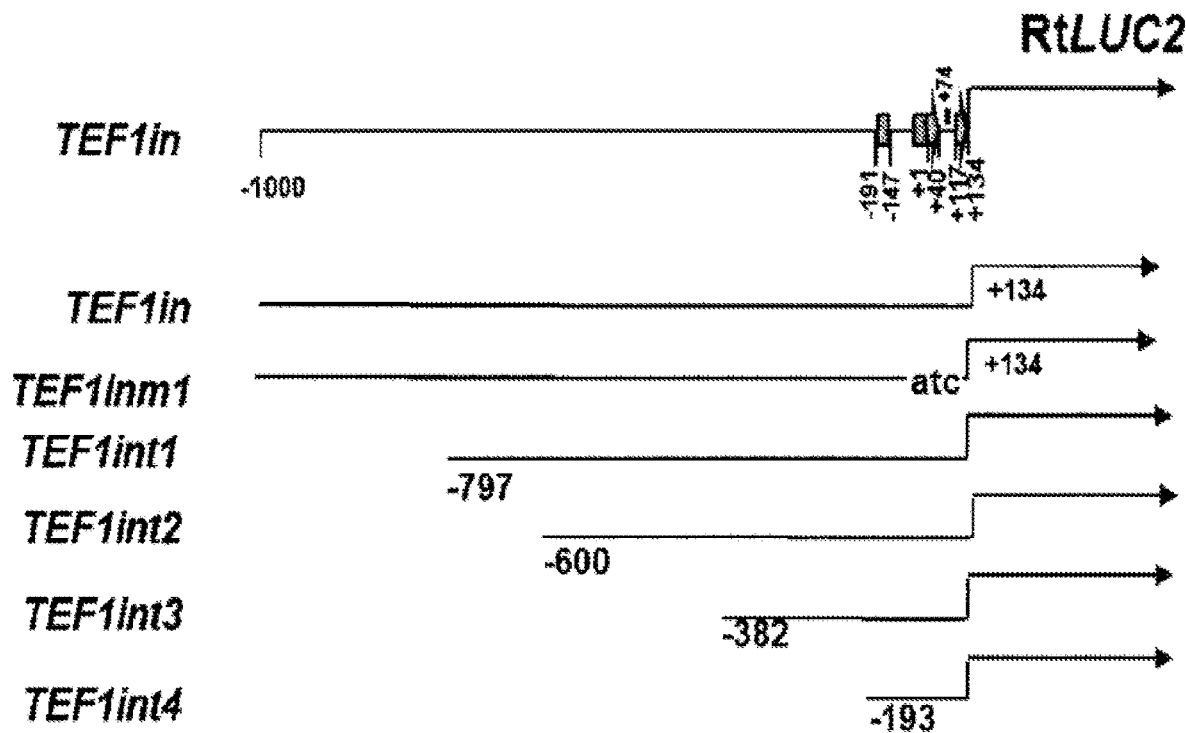
FIGS. 11A and 11B show a serial truncation analysis of TEF1in promoter.
Figure 11B:
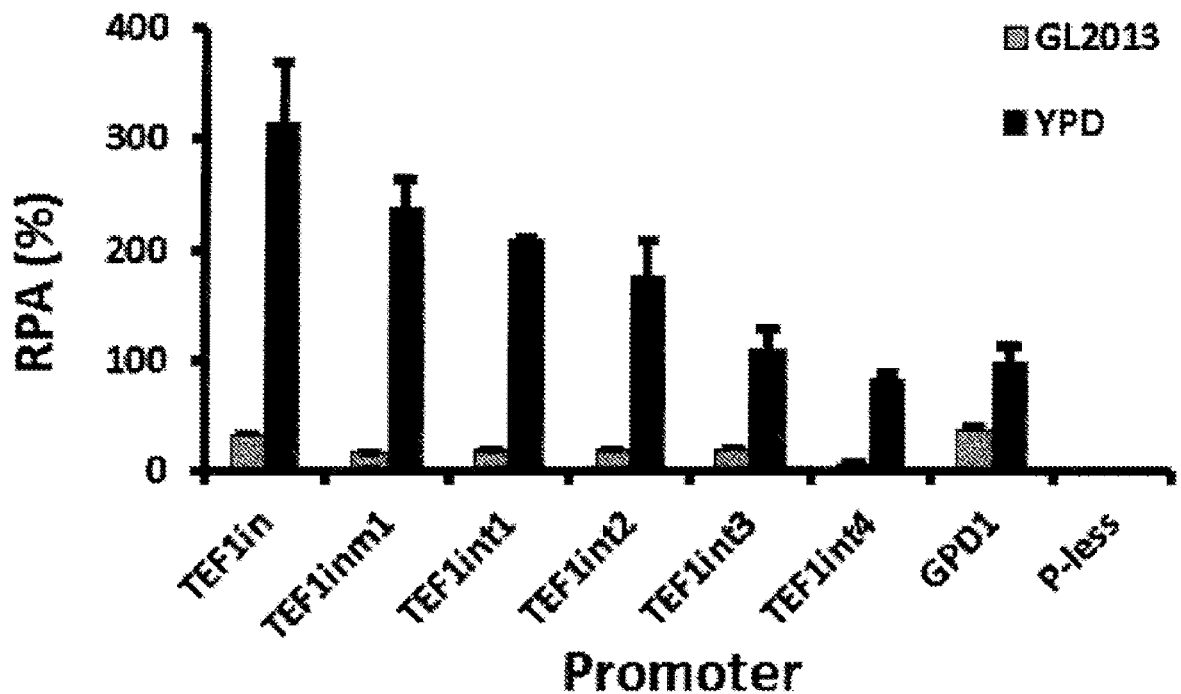

To investigate the potential upstream activating sequence (UAS) within the TEF1in promoter, a serial truncation of promoter sequence was generated (FIG. 11A). Luciferase reporter assay revealed that promoter activity decreased gradually upon the stepwise shortness of promoter sequence (FIG. 11B). The site-mutagenesis of the translation start codon (ATG to ATC in TEF1int1 promoter) also attenuated the promoter strength by 25% (FIG. 11B). Taken together, the 1.1 kb intron 1 and 2-incorporating upstream sequence of TEF1 is the best promoter.

Example 11

Media Effects

To investigate the performance of TEF1in promoter in lipid accumulation phase, we assayed the luciferase expression after cultured in GJ2013 medium for 2 days, and controlled by cultivation in YPD broth under the same conditions. Results showed that rich media (YPD broth) supported a much better performance of TEF1in promoter, exhibiting >3 fold promoter strength of that of GPD1 promoter (FIG. 11B). Both TEF1in and GPD1 promoter performed greatly worse in lipid production media (GJ2013 medium). In GJ2013 medium, GPD1 exhibited 37% of promoter strength in rich media, while TEF1in promoter kept only 11% of promoter strength in rich media (FIG. 11B). Collectively, it suggests that TEF1in promoter was more sensitive to the environmental nutrient conditions, and nutrient limitation or starvation could decrease its promoter activity.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Sampaio J P, Gadanho M, Bauer R, Weiß M: Taxonomic studies in the Microbotryomycetidae: *Leucosporidium golubevii* sp. nov., *Leucosporidiella* gen. nov. and the new orders Leucosporidiales and Sporidiobolales. *Mycol Prog* 2003, 2:53-68.
2. Yamazaki M, Komagata K: Taxonomic significance of electrophoretic comparison of enzymes in the genera *Rhodotorula* and *Rhodosporidium*. *International Journal of Systematic Bacteriology* 1981, 31:361-381.
3. Zhao X, Wu S, Hu C, Wang Q, Hua Y, Zhao Z K: Lipid production from Jerusalem artichoke by *Rhodosporidium toruloides* Y4. *J Ind Microbiol Biotechnol* 2010, 37:581-585.
4. Liu H, Zhao X, Wang F, Li Y, Jiang X, Ye M, Zhao Z K, Zou H: Comparative proteomic analysis of *Rhodosporidium toruloides* during lipid accumulation. *Yeast* 2009, 26:553-566.
5. Turcotte G, Kosaric N: Biosynthesis of lipids by *Rhodosporidium toruloides* ATCC 10788. *J Biotechnol* 1988, 8:221-237.
6. Liu Y, Koh C M, Sun L, Hlaing M M, Du M, Peng N, Ji L: Characterization of glyceraldehyde-3-phosphate dehydrogenase gene RtGPD1 and development of genetic transformation method by dominant selection in oleaginous yeast *Rhodosporidium toruloides*. *Appl Microbiol Biotechnol* 2013, 97:719-729.
7. Koh C M, Liu Y, Moehninsi, Du M, Ji L: Molecular characterization of KU70 and KU80 homologues and exploitation of a KU70-deficient mutant for improving gene deletion frequency in *Rhodosporidium toruloides*. *BMC Microbiol* 2014, 14:50-59.
8. Lin X, Wang Y, Zhang S, Zhu Z, Zhou Y J, Yang F, Sun W, Wang X, Zhao Z K: Functional integration of multiple genes into the genome of the oleaginous yeast *Rhodosporidium toruloides*. *FEMS Yeast Res* 2014, 14:547-555.
9. Abbott E P, Ianiri G, Castoria R, Idnurm A: Overcoming recalcitrant transformation and gene manipulation in *Pucciniomycotina* yeasts. *Appl Microbiol Biotechnol* 2012, 97:283-295.
10. Tai M, Stephanopoulos G: Engineering the push and pull of lipid biosynthesis in oleaginous yeast *Yarrowia lipolytica* for biofuel production. *Metabolic engineering* 2013, 15:1-9.
11. Ji L, Peng N, Cheng H I: Polynucleotide sequences from *Rhodosporidium* and *Rhodotorula* and use thereof. 2014, WO 2014/142747.
12. Zhu Z, Zhang S, Liu H, Shen H, Lin X, Yang F, Zhou Y J, Jin G, Ye M, Zou H, Zhao Z K: A multi-omic map of the lipid-producing yeast *Rhodosporidium toruloides*. *Nat Commun* 2012, 3:1112.

13. Ratledge C, Wynn J P: The biochemistry and molecular biology of lipid accumulation in oleaginous microorganisms. *Adv Appl Microbiol* 2002, 51:1-51.
14. Kolodziej S J, Penczek P A, Schroeter J P, Stoops J K: Structure-function relationships of the *Saccharomyces cerevisiae* fatty acid synthase. Three-dimensional structure. *J Biol Chem* 1996, 271:28422-28429.
15. Leibundgut M, Jenni S, Frick C, Ban N: Structural basis for substrate delivery by acyl carrier protein in the yeast fatty acid synthase. *Science* 2007, 316:288-290.
16. Lomakin I B, Xiong Y, Steitz T A: The crystal structure of yeast fatty acid synthase, a cellular machine with eight active sites working together. *Cell* 2007, 129:319-332.
17. Schweizer M, Roberts L M, Holtke H J, Takabayashi K, Hollerer E, Hoffmann B, Muller G, Kottig H, Schweizer E: The pentafunctional FAS1 gene of yeast: its nucleotide sequence and order of the catalytic domains. *Mol Gen Genet* 1986, 203:479-486.
18. Mohamed A H, Chirala S S, Mody N H, Huang W Y, Wakil S J: Primary structure of the multifunctional alpha subunit protein of yeast fatty acid synthase derived from FAS2 gene sequence. *J Biol Chem* 1988, 263:12315-12325.
19. Schuller H J, Schutz A, Knab S, Hoffmann B, Schweizer E: Importance of general regulatory factors Rap1p, Abf1p and Reb1p for the activation of yeast fatty acid synthase genes FAS1 and FAS2. *Eur J Biochem* 1994, 225:213-222.
20. Schuller H J, Schorr R, Hoffmann B, Schweizer E: Regulatory gene INO4 of yeast phospholipid biosynthesis is positively autoregulated and functions as a transactivator of fatty acid synthase genes FAS1 and FAS2 from *Saccharomyces cerevisiae*. *Nucleic Acids Res* 1992, 20:5955-5961.
21. Schwank S, Ebbert R, Rautenstrauss K, Schweizer E, Schuller H J: Yeast transcriptional activator INO2 interacts as an Ino2p/Ino4p basic helix-loop-helix heteromeric complex with the inositol/choline-responsive element necessary for expression of phospholipid biosynthetic genes in *Saccharomyces cerevisiae*. *Nucleic Acids Res* 1995, 23:230-237.
22. Wenz P, Schwank S, Hoja U, Schuller H J: A downstream regulatory element located within the coding sequence mediates autoregulated expression of the yeast fatty acid synthase gene FAS2 by the FAS1 gene product. *Nucleic Acids Res* 2001, 29:4625-4632.
23. Kimmel A R, Brasaemle D L, McAndrews-Hill M, Sztalryd C, Londos C: Adoption of PERILIPIN as a unifying nomenclature for the mammalian PAT-family of intracellular lipid storage droplet proteins. *J Lipid Res* 2010, 51:468-471.
24. Athenstaedt K, Jolivet P, Boulard C, Zivy M, Negroni L, Nicaud J M, Chardot T: Lipid particle composition of the yeast *Yarrowia lipolytica* depends on the carbon source. *Proteomics* 2006, 6:1450-1459.
25. Wang C, St Leger R J: The *Metarhizium anisopliae* Perilipin Homolog MPL1 Regulates Lipid Metabolism, Appressorial Turgor Pressure, and Virulence. *J Biol Chem* 2007, 282:21110-21115.
26. Zhu Z, Ding Y, Gong Z, Yang L, Zhang S, Zhang C, Lin X, Shen H, Zou H, Xie Z, et al: Dynamics of the Lipid Droplet Proteome of the Oleaginous Yeast *Rhodosporidium toruloides*. *Eukaryot Cell* 2015, 14:252-264.
27. Digel M, Ehehalt R, Fullekrug J: Lipid droplets lighting up: insights from live microscopy. *FEBS Lett* 2010, 584:2168-2175.
28. Hong S P, Seip J, Walters-Pollak D, Rupert R, Jackson R, Xue Z, Zhu Q: Engineering *Yarrowia lipolytica* to express secretory invertase with strong FBA1IN promoter. *Yeast* 2012, 29:59-72.
29. Liu Y, Koh C M J, Ngoh S T, Ji L: Engineering an efficient and tight d-amino acid-inducible gene expression system in *Rhodosporidium/Rhodotorula* species. *Microbial Cell Factories* 2015, 14:170-185.
30. Koh C M, Liu Y, Du M, Ji L: Molecular characterization of KU70 and KU80 homologues and exploitation of a KU70-deficient mutant for improving gene deletion frequency in *Rhodosporidium toruloides*. *BMC Microbiology* 2014, 14:50.
31. Kozak M: Point mutations define a sequence flanking the AUG initiator codon that modulates translation by eukaryotic ribosomes. *Cell* 1986, 44:283-292.
32. Li Y-H, Liu B, Zhao Z-B, Bai F-W: Optimization of Culture Conditions for Lipid Production by *Rhodosporidium toruloides*. *Chinese Journal of Biotechnology* 2006, 22:650-656.
3. Jin G, Zhang Y, Shen H, Yang X, Xie H, Zhao Z K: Fatty acid ethyl esters production in aqueous phase by the oleaginous yeast *Rhodosporidium toruloides*. *Bioresour Technol* 2013, 150:266-270.
34. Meesters P A, Eggink G: Isolation and characterization of a delta-9 fatty acid desaturase gene from the oleaginous yeast *Cryptococcus curvatus* CBS 570. *Yeast* 1996, 12:723-730.
35. Li Y, Zhao Z, Bai F: High-density cultivation of oleaginous yeast *Rhodosporidium toruloides* Y4 in fed-batch culture. *Enzyme and Microbial Technology* 2007, 41:312-317.
36. Lee L Y, Gelvin S B: T-DNA binary vectors and systems. *Plant Physiol* 2008, 146:325-332.
37. Leskinen P, Virta M, Karp M: One-step measurement of firefly luciferase activity in yeast. *Yeast* 2003, 20:1109-1113.
38. Zuo, J, Niu, Q W, Moller, S G, Chua, N H: Chemical-regulated, site-specific DNA excision in transgenic plants. *Nat Biotechnol,* 2001. 19:157-161.
39. Hu J, Ji L: Draft genome sequences of *Rhodosporidium toruloides* strains ATCC 10788 and ATCC 10657 with compatible mating types. *Genome announcements* 2016, 4:e00098-00016.
40. Paul D, Magbanua Z, Arick M, 2nd, French T, Bridges S M, Burgess S C, Lawrence M L: Genome Sequence of the Oleaginous Yeast *Rhodotorula glutinis* ATCC 204091. *Genome Announc* 2014, 2:1-2.

What is claimed is:

1. A nucleic acid comprising a promoter, the promoter comprising a nucleotide sequence having at least 95% sequence identity, based on the Clustal V or Clustal W method of alignment, when compared to the nucleotide sequence set forth in SEQ ID NO: 75, 85, 93 or 94,
   wherein the promoter sequence has been modified to change a 5' upstream start codon to a non-start codon and to change the 3' end to contain a start codon, and
   wherein the promoter is capable of driving strong expression of RNA or proteins in a species selected from *Rhodosporidium* or *Rhodotorula* genus.

2. The nucleic acid of claim 1, further comprising the promoter operably linked to a nucleic acid of interest.

3. The nucleic acid of claim 2, wherein the nucleic acid of interest is further operably linked to a transcription terminator.

4. A transgenic yeast or fungal cell comprising the nucleic acid of claim 1.

5. The transgenic yeast or fungal cell of claim 4, wherein the cell is a cell of a species of *Rhodosporidium* genus or *Rhodotorula* genus.

6. A composition comprising a culture medium and the transgenic yeast or fungal cell of claim 4.

7. A method for preparing a transgenic yeast or fungal cell comprising:
   (a) introducing the nucleic acid of claim 1 into a yeast or fungal cell and
   (b) selecting a transgenic yeast or fungal cell which comprises the nucleic acid construct.

8. A method of expressing a nucleic acid of interest in a yeast or fungal cell comprising culturing the transgenic yeast or fungal cell of claim 4 in a culture medium under conditions suitable for expression of the nucleic acid of interest.

9. A composition comprising a culture medium and the transgenic yeast or fungal cell of claim 5.

10. A method of expressing a nucleic acid of interest in a yeast or fungal cell comprising culturing the transgenic yeast or fungal cell of claim 5 in a culture medium under conditions suitable for expression of the nucleic acid of interest.

11. A transgenic yeast or fungal cell comprising the nucleic acid of claim 3.

12. The transgenic yeast or fungal cell of claim 11, wherein the cell is a cell of a species of *Rhodosporidium* genus or *Rhodotorula* genus.

13. A composition comprising a culture medium and the transgenic yeast or fungal cell of claim 11.

14. A method for preparing a transgenic yeast or fungal cell comprising:
   (a) introducing the nucleic acid of claim 3 into a yeast or fungal cell and
   (b) selecting a transgenic yeast or fungal cell which comprises the nucleic acid construct.

15. A method of expressing a nucleic acid of interest in a yeast or fungal cell comprising culturing the transgenic yeast or fungal cell of claim 11 in a culture medium under conditions suitable for expression of the nucleic acid of interest.

16. A method of expressing a nucleic acid of interest in a yeast or fungal cell comprising culturing the transgenic yeast or fungal cell of claim 12 in a culture medium under conditions suitable for expression of the nucleic acid of interest.

17. The nucleic acid of claim 1, wherein the promoter contains an intron 1 and an intron 2 and wherein intron 2 contains a ct box.

18. The nucleic acid of claim 17, wherein intron 1 contains a ct box.

19. The nucleic acid of claim 18, wherein the promoter comprises:
   (a) the nucleotide sequence set forth in SEQ ID NO:75;
   (b) a nucleotide sequence having at least 95% sequence identity, based on the Clustal V or Clustal W method of alignment, when compared to the nucleotide sequence set forth in SEQ ID NO:75;
   (c) the nucleotide sequence set forth in SEQ ID NO:93; or
   (d) a nucleotide sequence having at least 95% sequence identity, based on the Clustal V or Clustal W method of alignment, when compared to the nucleotide sequence set forth in SEQ ID NO:93.

* * * * *

SEQUENCE LISTING

<160> NUMBER OF SEQ ID NOS: 122

<210> SEQ ID NO 1
<211> LENGTH: 299
<212> TYPE: DNA
<213> ORGANISM: Rhodosporidium toruloides

<400> SEQUENCE: 1

```
cgcgccttgt ccgcttcccc atcctcgtcc tgctcttgct ctcttcccta ccacactctc    60
ccgcttgcgg gctctctttc tcgcttggcg ctcctgctac cgctactcta gactctccta   120
gtctccctgc acaaccatcc ctatcccctc cgcctctctc gcacaccccc acagcttcg    180 ttccccaact tcacttccga tgccgtgcgt cgcctccctt cgcctggcg ggcccgcgcc    240 tgcttccgag acaactact gattgtggga tcatgcgacg acaggttctc tggcgaggc    299
```

<210> SEQ ID NO 2
<211> LENGTH: 562
<212> TYPE: DNA
<213> ORGANISM: Rhodosporidium toruloides

<400> SEQUENCE: 2

```
cacgcctctg tgactcggta cggagagaga gagcgttggg ttgggttggg gattgtggcg    60
agcgaagggc gacccagcag ccagggagag ggagttggtc tggatgcaaa ccatgcgcat   120
ctcctctcgc agttgaatcg ttttteeecge tetgeceteg ctctctcttc cttctgctct   180
ttactcgctc acgaacaaca acgagccaca cagcgtgagc acacaccgct gcactcactc    240
gctgtcacgg accgcagctc acccttatcg tcactccctc tcccaccgca cagcctcact    300
ccctctctcg ctctccctca caagcacaac acacggcaca ctcgcacgca cactcgcacg    360
caatggccac cgtcaacgag aagcagcccg ccaccgacgc gccctcgcg cacgagaccg    420 ccatccaccg cgtgcgtccc catccctccc actgtcttcc tcgtgaaacc cgctcacccg    480
ttcgcaagca cacacgcagg tgtcggacta ccccgtgatc aaagacaccc tctcctcgct    540
cgactcgtac gcccactcgc ac                                             562
```

<210> SEQ ID NO 3
<211> LENGTH: 80
<212> TYPE: DNA
<213> ORGANISM: Rhodosporidium toruloides

<400> SEQUENCE: 3

```
gtgcgtcgcc tcccttcgc ctggcgggcc cgcgcctgct tccgaggaca actactgatt    60
gtgggatcat gcgacgacag                                                80
```

<210> SEQ ID NO 4
<211> LENGTH: 365
<212> TYPE: DNA
<213> ORGANISM: Rhodosporidium toruloides

<400> SEQUENCE: 4

```
cacgcctctg tgactcggta cggagagaga gagcgttggg ttgggttggg gattgtggcg    60
agcgaagggc gacccagcag ccagggagag ggagttggtc tggatgcaaa ccatgcgcat   120
ctcctctcgc agttgaatcg ttttteeecge tetgeceteg ctctctcttc cttctgctct   180
ttactcgctc acgaacaaca acgagccaca cagcgtgagc acacaccgct gcactcactc    240
gctgtcacgg accgcagctc acccttatcg tcactccctc tcccaccgca cagcctcact    300
ccctctctcg ctctccctca caagcacaac acacggcaca ctcgcacgca cactcgcacg    360
ccatg                                                                365
```

<210> SEQ ID NO 5
<211> LENGTH: 517
<212> TYPE: DNA

<213> ORGANISM: Rhodosporidium toruloides

<400> SEQUENCE: 5

| | |
|---|---|
| cacgcctctg tgactcggta cggagagaga gagcgttggg ttgggttggg gattgtggcg | 60 |
| agcgaagggc gacccagcag ccagggagag ggagttggtc tggatgcaaa ccatgcgcat | 120 |
| ctcctctcgc agttgaatcg ttttccccgc tctgccctcg ctctctcttc cttctgctct | 180 |
| ttactcgctc acgaacaaca acgagccaca cagcgtgagc acacaccgct gcactcactc | 240 |
| gctgtcacgg accgcagctc acccttatcg tcactccctc tcccaccgca cagcctcact | 300 |
| ccctctctcg ctctccctca caagcacaac acacggcaca ctcgcacgca cactcgcacg | 360 |
| caatggccac cgtcaacgag aagcagcccg ccaccgacgc gccctcgcg cacgagaccg | 420 |
| ccatccaccg cgtgcgtccc catccctccc actgtcttcc tcgtgaaacc cgctcacccg | 480 |
| ttcgcaagca cacgcagg tgtcggacta ccccatg | 517 |

<210> SEQ ID NO 6
<211> LENGTH: 517
<212> TYPE: DNA
<213> ORGANISM: Rhodosporidium toruloides

<400> SEQUENCE: 6

| | |
|---|---|
| cacgcctctg tgactcggta cggagagaga gagcgttggg ttgggttggg gattgtggcg | 60 |
| agcgaagggc gacccagcag ccagggagag ggagttggtc tggatgcaaa ccatgcgcat | 120 |
| ctcctctcgc agttgaatcg ttttccccgc tctgccctcg ctctctcttc cttctgctct | 180 |
| ttactcgctc acgaacaaca acgagccaca cagcgtgagc acacaccgct gcactcactc | 240 |
| gctgtcacgg accgcagctc acccttatcg tcactccctc tcccaccgca cagcctcact | 300 |
| ccctctctcg ctctccctca caagcacaac acacggcaca ctcgcacgca cactcgcacg | 360 |
| caatcgccac cgtcaacgag aagcagcccg ccaccgacgc gccctcgcg cacgagaccg | 420 |
| ccatccaccg cgtgcgtccc catccctccc actgtcttcc tcgtgaaacc cgctcacccg | 480 |
| ttcgcaagca cacgcagg tgtcggacta ccccatg | 517 |

<210> SEQ ID NO 7
<211> LENGTH: 378
<212> TYPE: DNA
<213> ORGANISM: Rhodosporidium toruloides

<400> SEQUENCE: 7

| | |
|---|---|
| gttttttcccg ctctgccctc gctctctctt ccttctgctc tttactcgct cacgaacaac | 60 |
| aacgagccac acagcgtgag cacacaccgc tgcactcact cgctgtcacg gaccgcagct | 120 |
| cacccttatc gtcactccct ctcccaccgc acagcctcac tccctctctc gctctccctc | 180 |
| acaagcacaa cacacggcac actcgcacgc acactcgcac gcaatcgcca ccgtcaacga | 240 |
| gaagcagccc gccaccgacg cgccctcgc gcacgagacc gccatccacc gcgtgcgtcc | 300 |
| ccatccctcc cactgtcttc ctcgtgaaac ccgctcaccc gttcgcaagc acacgcag | 360 |
| gtgtcggact accccatg | 378 |

<210> SEQ ID NO 8
<211> LENGTH: 30
<212> TYPE: DNA
<213> ORGANISM: Artificial Sequence
<220> FEATURE:
<223> OTHER INFORMATION: oligonucleotide

<400> SEQUENCE: 8
tttccgcggt cgaatttccc cgatcgttca                                    30

<210> SEQ ID NO 9
<211> LENGTH: 21
<212> TYPE: DNA
<213> ORGANISM: Artificial Sequence
<220> FEATURE:
<223> OTHER INFORMATION: oligonucleotide

<400> SEQUENCE: 9
gagtcgctca cctactgcat c                                             21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide

<400> SEQUENCE: 10
gaaggcgggg gttctcggaa g                                             21

<210> SEQ ID NO 11
<211> LENGTH: 18
<212> TYPE: DNA
<213> ORGANISM: Artificial Sequence
<220> FEATURE:
<223> OTHER INFORMATION: oligonucleotide

<400> SEQUENCE: 11
gacgaggtca tccgcgag                                                 18

<210> SEQ ID NO 12
<211> LENGTH: 23
<212> TYPE: DNA
<213> ORGANISM: Artificial Sequence
<220> FEATURE:
<223> OTHER INFORMATION: oligonucleotide

<400> SEQUENCE: 12
gaccagctct accagcgcat cac                                           23

<210> SEQ ID NO 13
<211> LENGTH: 25
<212> TYPE: DNA
<213> ORGANISM: Artificial Sequence
<220> FEATURE:
<223> OTHER INFORMATION: oligonucleotide

<400> SEQUENCE: 13
tcgccctcct ccctgctcg caaat                                          25

<210> SEQ ID NO 14
<211> LENGTH: 29
<212> TYPE: DNA
<213> ORGANISM: Artificial Sequence
<220> FEATURE:
<223> OTHER INFORMATION: oligonucleotide

<400> SEQUENCE: 14
tttactagtg gtcgcttctt tcctcgcag                                     29

<210> SEQ ID NO 15
<211> LENGTH: 28
<212> TYPE: DNA

```
<213> ORGANISM: Artificial Sequence
<220> FEATURE:
<223> OTHER INFORMATION: oligonucleotide

<400> SEQUENCE: 15
tttccatggg aagtgaagtt ggggaacg                                          28

<210> SEQ ID NO 16
<211> LENGTH: 28
<212> TYPE: DNA
<213> ORGANISM: Artificial Sequence
<220> FEATURE:
<223> OTHER INFORMATION: oligonucleotide

<400> SEQUENCE: 16
tttccatgga gaacctgtcg tcgcatga                                          28

<210> SEQ ID NO 17
<211> LENGTH: 26
<212> TYPE: DNA
<213> ORGANISM: Artificial Sequence
<220> FEATURE:
<223> OTHER INFORMATION: oligonucleotide

<400> SEQUENCE: 17
tttactagtc gcgccttgtc cgcttc                                            26

<210> SEQ ID NO 18
<211> LENGTH: 30
<212> TYPE: DNA
<213> ORGANISM: Artificial Sequence
<220> FEATURE:
<223> OTHER INFORMATION: oligonucleotide

<400> SEQUENCE: 18
tttactagtc ttcagaaggg atgggaggag                                        30

<210> SEQ ID NO 19
<211> LENGTH: 28
<212> TYPE: DNA
<213> ORGANISM: Artificial Sequence
<220> FEATURE:
<223> OTHER INFORMATION: oligonucleotide

<400> SEQUENCE: 19
tttactagtc tggcacgccg tcgaggac                                          28

<210> SEQ ID NO 20
<211> LENGTH: 30
<212> TYPE: DNA
<213> ORGANISM: Artificial Sequence
<220> FEATURE:
<223> OTHER INFORMATION: oligonucleotide

<400> SEQUENCE: 20
tttactagtg acccggatta ctcgagcatc                                        30

<210> SEQ ID NO 21
<211> LENGTH: 29
<212> TYPE: DNA
<213> ORGANISM: Artificial Sequence
<220> FEATURE:
<223> OTHER INFORMATION: oligonucleotide

<400> SEQUENCE: 21
tttactagtg ctcaagcgag ccgatacag                                         29
```

<210> SEQ ID NO 22
<211> LENGTH: 28
<212> TYPE: DNA
<213> ORGANISM: Artificial Sequence
<220> FEATURE:
<223> OTHER INFORMATION: oligonucleotide

<400> SEQUENCE: 22
tttactagtt gcgggagttg ttggacac                                28

<210> SEQ ID NO 23
<211> LENGTH: 23
<212> TYPE: DNA
<213> ORGANISM: Artificial Sequence
<220> FEATURE:
<223> OTHER INFORMATION: oligonucleotide

<400> SEQUENCE: 23
gatcggaagt gaagttgggg aac                                    23

<210> SEQ ID NO 24
<211> LENGTH: 46
<212> TYPE: DNA
<213> ORGANISM: Artificial Sequence
<220> FEATURE:
<223> OTHER INFORMATION: oligonucleotide

<400> SEQUENCE: 24
ttcgttcccc aacttcactt ccgatcccgt gcgtcgcctc cctttc           46

<210> SEQ ID NO 25
<211> LENGTH: 30
<212> TYPE: DNA
<213> ORGANISM: Artificial Sequence
<220> FEATURE:
<223> OTHER INFORMATION: oligonucleotide

<400> SEQUENCE: 25
tttactagtt cgacttgtct tcctccgcga                             30

<210> SEQ ID NO 26
<211> LENGTH: 26
<212> TYPE: DNA
<213> ORGANISM: Artificial Sequence
<220> FEATURE:
<223> OTHER INFORMATION: oligonucleotide

<400> SEQUENCE: 26
tttccatggc gaaagaggga tgtgag                                 26

<210> SEQ ID NO 27
<211> LENGTH: 28
<212> TYPE: DNA
<213> ORGANISM: Artificial Sequence
<220> FEATURE:
<223> OTHER INFORMATION: oligonucleotide

<400> SEQUENCE: 27
tttccatgga gaagaggttc tgcgcgga                               28

<210> SEQ ID NO 28
<211> LENGTH: 30
<212> TYPE: DNA
<213> ORGANISM: Artificial Sequence
<220> FEATURE:

<223> OTHER INFORMATION: oligonucleotide

<400> SEQUENCE: 28
tttactagtc tgtgatgcta ggtgtcgatc                                30

<210> SEQ ID NO 29
<211> LENGTH: 28
<212> TYPE: DNA
<213> ORGANISM: Artificial Sequence
<220> FEATURE:
<223> OTHER INFORMATION: oligonucleotide

<400> SEQUENCE: 29
tttccatggc tgctgcgttt cctggtac                                  28

<210> SEQ ID NO 30
<211> LENGTH: 26
<212> TYPE: DNA
<213> ORGANISM: Artificial Sequence
<220> FEATURE:
<223> OTHER INFORMATION: oligonucleotide

<400> SEQUENCE: 30
tttccatggc gtcgtactcg cggatg                                    26

<210> SEQ ID NO 31
<211> LENGTH: 30
<212> TYPE: DNA
<213> ORGANISM: Artificial Sequence
<220> FEATURE:
<223> OTHER INFORMATION: oligonucleotide

<400> SEQUENCE: 31
tttactagtg aactcgactc attacgggag                                30

<210> SEQ ID NO 32
<211> LENGTH: 31
<212> TYPE: DNA
<213> ORGANISM: Artificial Sequence
<220> FEATURE:
<223> OTHER INFORMATION: oligonucleotide

<400> SEQUENCE: 32
tttccatggt gtgcggtatt cgacgagttt g                              31

<210> SEQ ID NO 33
<211> LENGTH: 29
<212> TYPE: DNA
<213> ORGANISM: Artificial Sequence
<220> FEATURE:
<223> OTHER INFORMATION: oligonucleotide

<400> SEQUENCE: 33
tttccatgga gtagtgctgt ccgcgcaga                                 29

<210> SEQ ID NO 34
<211> LENGTH: 29
<212> TYPE: DNA
<213> ORGANISM: Artificial Sequence
<220> FEATURE:
<223> OTHER INFORMATION: oligonucleotide

<400> SEQUENCE: 34
tttactagtc tctagcctac gaccgcctc                                 29

```
<210> SEQ ID NO 35
<211> LENGTH: 29
<212> TYPE: DNA
<213> ORGANISM: Artificial Sequence
<220> FEATURE:
<223> OTHER INFORMATION: oligonucleotide

<400> SEQUENCE: 35
tttccatggt agcgagtcgt tctctgcag                                   29

<210> SEQ ID NO 36
<211> LENGTH: 30
<212> TYPE: DNA
<213> ORGANISM: Artificial Sequence
<220> FEATURE:
<223> OTHER INFORMATION: oligonucleotide

<400> SEQUENCE: 36
tttactagtt cgacttgtct tcctccgcga                                  30

<210> SEQ ID NO 37
<211> LENGTH: 26
<212> TYPE: DNA
<213> ORGANISM: Artificial Sequence
<220> FEATURE:
<223> OTHER INFORMATION: oligonucleotide

<400> SEQUENCE: 37
tttccatggc gaaagaggga tgtgag                                      26

<210> SEQ ID NO 38
<211> LENGTH: 28
<212> TYPE: DNA
<213> ORGANISM: Artificial Sequence
<220> FEATURE:
<223> OTHER INFORMATION: oligonucleotide

<400> SEQUENCE: 38
tttccatgga gaagaggttc tgcgcgga                                    28

<210> SEQ ID NO 39
<211> LENGTH: 30
<212> TYPE: DNA
<213> ORGANISM: Artificial Sequence
<220> FEATURE:
<223> OTHER INFORMATION: oligonucleotide

<400> SEQUENCE: 39
tttactagtc acgcctctgt gactcggtac                                  30

<210> SEQ ID NO 40
<211> LENGTH: 28
<212> TYPE: DNA
<213> ORGANISM: Artificial Sequence
<220> FEATURE:
<223> OTHER INFORMATION: oligonucleotide

<400> SEQUENCE: 40
tttccatggc gtgcgagtgt gcgtgcga                                    28

<210> SEQ ID NO 41
<211> LENGTH: 27
<212> TYPE: DNA
<213> ORGANISM: Artificial Sequence
<220> FEATURE:
<223> OTHER INFORMATION: oligonucleotide
```

<400> SEQUENCE: 41
tttccatggg gtagtccgac acctgcg                                    27

<210> SEQ ID NO 42
<211> LENGTH: 32
<212> TYPE: DNA
<213> ORGANISM: Artificial Sequence
<220> FEATURE:
<223> OTHER INFORMATION: oligonucleotide

<400> SEQUENCE: 42
agcttggatc catgtcgcgt aggctcgttc gg                              32

<210> SEQ ID NO 43
<211> LENGTH: 45
<212> TYPE: DNA
<213> ORGANISM: Artificial Sequence
<220> FEATURE:
<223> OTHER INFORMATION: oligonucleotide

<400> SEQUENCE: 43
ttaacgccga attgaattcg gaggtttttc gacgcacgtg agtcg                45

<210> SEQ ID NO 44
<211> LENGTH: 40
<212> TYPE: DNA
<213> ORGANISM: Artificial Sequence
<220> FEATURE:
<223> OTHER INFORMATION: oligonucleotide

<400> SEQUENCE: 44
acgcgacatg gatccaagct caagctaagc tgatcctacc                      40

<210> SEQ ID NO 45
<211> LENGTH: 39
<212> TYPE: DNA
<213> ORGANISM: Artificial Sequence
<220> FEATURE:
<223> OTHER INFORMATION: oligonucleotide

<400> SEQUENCE: 45
ggcgcccatg ctgaattaac gccgaattga attcgcgcg                       39

<210> SEQ ID NO 46
<211> LENGTH: 41
<212> TYPE: DNA
<213> ORGANISM: Artificial Sequence
<220> FEATURE:
<223> OTHER INFORMATION: oligonucleotide

<400> SEQUENCE: 46
ccttgcgtat aatatttgcc cacgagggac ttgagatgtg a                    41

<210> SEQ ID NO 47
<211> LENGTH: 25
<212> TYPE: DNA
<213> ORGANISM: Artificial Sequence
<220> FEATURE:
<223> OTHER INFORMATION: oligonucleotide

<400> SEQUENCE: 47
gttaattcag catgggcgcc cgcgc                                      25

<210> SEQ ID NO 48
<211> LENGTH: 43

```
<212> TYPE: DNA
<213> ORGANISM: Artificial Sequence
<220> FEATURE:
<223> OTHER INFORMATION: oligonucleotide

<400> SEQUENCE: 48
cacgcacact cgcacgcaat cgccaccgtc aacgagaagc agc                43

<210> SEQ ID NO 49
<211> LENGTH: 43
<212> TYPE: DNA
<213> ORGANISM: Artificial Sequence
<220> FEATURE:
<223> OTHER INFORMATION: oligonucleotide

<400> SEQUENCE: 49
gctgcttctc gttgacggtg gcgattgcgt gcgagtgtgc gtg                43

<210> SEQ ID NO 50
<211> LENGTH: 46
<212> TYPE: DNA
<213> ORGANISM: Artificial Sequence
<220> FEATURE:
<223> OTHER INFORMATION: oligonucleotide

<400> SEQUENCE: 50
agcacacacg caggtgtcgg ccgccaccat ggaggacgcc aagaac             46

<210> SEQ ID NO 51
<211> LENGTH: 46
<212> TYPE: DNA
<213> ORGANISM: Artificial Sequence
<220> FEATURE:
<223> OTHER INFORMATION: oligonucleotide

<400> SEQUENCE: 51
gttcttggcg tcctccatgg tggcggccga cacctgcgtg tgtgct             46

<210> SEQ ID NO 52
<211> LENGTH: 27
<212> TYPE: DNA
<213> ORGANISM: Artificial Sequence
<220> FEATURE:
<223> OTHER INFORMATION: oligonucleotide

<400> SEQUENCE: 52
tttactagtt tttcccgctc tgccctc                                  27

<210> SEQ ID NO 53
<211> LENGTH: 31
<212> TYPE: DNA
<213> ORGANISM: Artificial Sequence
<220> FEATURE:
<223> OTHER INFORMATION: oligonucleotide

<400> SEQUENCE: 53
tttactagta cgaacaacaa cgagccacac a                             31

<210> SEQ ID NO 54
<211> LENGTH: 29
<212> TYPE: DNA
<213> ORGANISM: Artificial Sequence
<220> FEATURE:
<223> OTHER INFORMATION: oligonucleotide

<400> SEQUENCE: 54
```

```
tttactagtg ctcacccttg tcgtcactc                                        29
```

<210> SEQ ID NO 55
<211> LENGTH: 29
<212> TYPE: DNA
<213> ORGANISM: Artificial Sequence
<220> FEATURE:
<223> OTHER INFORMATION: oligonucleotide

<400> SEQUENCE: 55

```
tttactagtg cctcactccc tctctcgct                                        29
```

<210> SEQ ID NO 56
<211> LENGTH: 29
<212> TYPE: DNA
<213> ORGANISM: Artificial Sequence
<220> FEATURE:
<223> OTHER INFORMATION: oligonucleotide

<400> SEQUENCE: 56

```
tttactagta caagcacaac acacggcac                                        29
```

<210> SEQ ID NO 57
<211> LENGTH: 40
<212> TYPE: DNA
<213> ORGANISM: Artificial Sequence
<220> FEATURE:
<223> OTHER INFORMATION: oligonucleotide

<400> SEQUENCE: 57

```
accgccatcc accgcgtgcg gtgaaacccg ctcacccgtt                            40
```

<210> SEQ ID NO 58
<211> LENGTH: 40
<212> TYPE: DNA
<213> ORGANISM: Artificial Sequence
<220> FEATURE:
<223> OTHER INFORMATION: oligonucleotide

<400> SEQUENCE: 58

```
aacgggtgag cgggtttcac cgcacgcggt ggatggcggt                            40
```

<210> SEQ ID NO 59
<211> LENGTH: 1504
<212> TYPE: DNA
<213> ORGANISM: Rhodosporidium toruloides

<400> SEQUENCE: 59

```
ggtcgcttct ttcctcgcag cacgcttttg tcggctccct gatcagcaca caagctaact       60
aacgctctgg tttcgctggc agtcatgcac ggccttggct cgtcaacctc gttctgggaa      120
gcgcccttct cccgctcaaa cctgtcctcc cgcttccgcc tcatccgcta cgacttcgac      180
ggccacggtc tctcgcccgt ctcgtccctc gacgcagcag atgacggcgc catgatcccg      240
ctcgacgacc tcgtcgggga cttggcggct gtgatcgagt gggctggggt ggagaaggtt      300
gcgggagttg ttggacactc gatgagcggg ctggtggcga gcacatttgc ggccaagtac      360
ccgcagaagc tcgacaagct cggtgagtcg cattgaacct tcctccgccg tctcttctcc      420
gctgacgatt cgtcgacttg gccctgcttc tcgcgcagtc ctcctcggcg caatgcgctc      480
tctgaaccct accgtccaaa gcaacatgct caagcgagcc gatacagtcc tcgaatccgg      540
cctctcagca atcgtcgcac aagtcgtctc cgccgctttg tccgacaagt caaagcagga      600
ctcgcccctc tcggcagcga tggtgcgaac gctcgtgctt ggaacggacc cgagagggta      660
```

```
cgcggcggcg tgtagggcgc ttgcgggtgc gaaggacccg gattactcga gcatcaaggc      720
cgagacgttg ggtgcgttcg cttgttctcc ttcctctgct tttctcccag caactgacgc      780
aagcgtctgc aacacagtcg tcgcaggcga gtttgactac ctctcgaaca aggagacgac      840
cgacgcgctg gtcaacgaca tcccgggcgc ggagaaggtc cagatggaca gtgtcggcca      900
ctggcacgcc gtcgaggacc ccgttggact cgccaagatc ctcgatgggt tcttcttgca      960
ggggaaatga ggttgggaag ggggatagac tggggagaac ggcaggtgc gtacgcagcg      1020 gacgtcggtc gggaggactt tttcggggag gatattcgct gactgactcc gacgtcgctt     1080
tcctccttgc agtatcttca gaagggatgg gaggaggcga actgcaaggg taatgaacga     1140
gacaacgccg agggaggaag cgccggaact ctcgggggcg aagaaggagt ggtgtcttcg     1200
ccagcgaaca gcttccgggg tgggttggac agcgccagta gaattccagc gtcgcaacag     1260
agctctagtc gaccgcgatc acccacaagg acgagagcgg gtcgcgcctt gtccgcttcc     1320
ccatcctcgt cctgctcttg ctctcttccc taccacactc tcccgcttgc gggctctctt     1380
tctcgcttgg cgctcctgct accgctactc tagactctcc tagtctccct gcacaaccat     1440
ccctatcccc tccgcctctc tcgcacaccc cccacagctt cgttccccaa cttcacttcc     1500
gatg                                                                  1504
```

```
<210> SEQ ID NO 60
<211> LENGTH: 1596
<212> TYPE: DNA
<213> ORGANISM: Rhodosporidium toruloides

<400> SEQUENCE: 60
```

```
ggtcgcttct ttcctcgcag cacgcttttg tcggctccct gatcagcaca caagctaact       60
aacgctctgg tttcgctggc agtcatgcac ggccttggct cgtcaacctc gttctgggaa      120
gcgcccttct cccgctcaaa cctgtcctcc cgcttccgcc tcatccgcta cgacttcgac      180
ggccacggtc tctcgcccgt ctcgtccctc gacgcagcag atgacggcgc catgatcccg      240
ctcgacgacc tcgtcgggga cttggcggct gtgatcgagt gggctggggt ggagaaggtt      300
gcgggagttg ttggacactc gatgagcggg ctggtggcga gcacatttgc ggccaagtac      360
ccgcagaagc tcgacaagct cggtgagtcg cattgaacct tcctccgccg tctcttctcc      420
gctgacgatt cgtcgacttg gccctgcttc tcgcgcagtc ctcctcggcg caatgcgctc      480
tctgaaccct accgtccaaa gcaacatgct caagcgagcc gatacagtcc tcgaatccgg      540
cctctcagca atcgtcgcac aagtcgtctc cgccgctttg tccgacaagt caaagcagga      600
ctcgcccctc tcggcagcga tggtgcgaac gctcgtgctt ggaacggacc cgagagggta      660
cgcggcggcg tgtagggcgc ttgcgggtgc gaaggacccg gattactcga gcatcaaggc      720
cgagacgttg ggtgcgttcg cttgttctcc ttcctctgct tttctcccag caactgacgc      780
aagcgtctgc aacacagtcg tcgcaggcga gtttgactac ctctcgaaca aggagacgac      840
cgacgcgctg gtcaacgaca tcccgggcgc ggagaaggtc cagatggaca gtgtcggcca      900
ctggcacgcc gtcgaggacc ccgttggact cgccaagatc ctcgatgggt tcttcttgca      960
ggggaaatga ggttgggaag ggggatagac tggggagaac ggcaggtgc gtacgcagcg      1020 gacgtcggtc gggaggactt tttcggggag gatattcgct gactgactcc gacgtcgctt     1080
tcctccttgc agtatcttca gaagggatgg gaggaggcga actgcaaggg taatgaacga     1140
gacaacgccg agggaggaag cgccggaact ctcgggggcg aagaaggagt ggtgtcttcg     1200
```

```
ccagcgaaca gcttccgggg tgggttggac agcgccagta gaattccagc gtcgcaacag    1260
agctctagtc gaccgcgatc acccacaagg acgagagcgg gtcgcgcctt gtccgcttcc    1320
ccatcctcgt cctgctcttg ctctcttccc taccacactc tcccgcttgc gggctctctt    1380
tctcgcttgg cgctcctgct accgctactc tagactctcc tagtctccct gcacaaccat    1440
ccctatcccc tccgcctctc tcgcacaccc cccacagctt cgttccccaa cttcacttcc    1500
gatgccgtgc gtcgcctccc tttcgcctgg cgggcccgcg cctgcttccg aggacaacta    1560
ctgattgtgg gatcatgcga cgacaggttc tctggc                              1596

<210> SEQ ID NO 61
<211> LENGTH: 365
<212> TYPE: DNA
<213> ORGANISM: Rhodosporidium toruloides

<400> SEQUENCE: 61
cacgcctctg tgactcggta cggagagaga gagcgttggg ttgggttggg gattgtggcg      60
agcgaagggc gacccagcag ccagggagag ggagttggtc tggatgcaaa ccatgcgcat     120
ctcctctcgc agttgaatcg ttttccccgc tctgccctcg ctctctcttc cttctgctct     180
ttactcgctc acgaacaaca acgagccaca cagcgtgagc acacaccgct gcactcactc     240
gctgtcacgg accgcagctc acccttatcg tcactccctc tcccaccgca cagcctcact     300
ccctctctcg ctctccctca caagcacaac acacggcaca ctcgcacgca cactcgcacg     360
caatg                                                                 365

<210> SEQ ID NO 62
<211> LENGTH: 517
<212> TYPE: DNA
<213> ORGANISM: Rhodosporidium toruloides

<400> SEQUENCE: 62
cacgcctctg tgactcggta cggagagaga gagcgttggg ttgggttggg gattgtggcg      60
agcgaagggc gacccagcag ccagggagag ggagttggtc tggatgcaaa ccatgcgcat     120
ctcctctcgc agttgaatcg ttttccccgc tctgccctcg ctctctcttc cttctgctct     180
ttactcgctc acgaacaaca acgagccaca cagcgtgagc acacaccgct gcactcactc     240
gctgtcacgg accgcagctc acccttatcg tcactccctc tcccaccgca cagcctcact     300
ccctctctcg ctctccctca caagcacaac acacggcaca ctcgcacgca cactcgcacg     360
caatggccac cgtcaacgag aagcagcccg ccaccgacgc gccccgcgcg cacgagaccg     420
ccatccaccg cgtgcgtccc catccctccc actgtcttcc tcgtgaaacc cgctcacccg     480
ttcgcaagca cacacgcagg tgtcggacta ccccgtg                              517

<210> SEQ ID NO 63
<211> LENGTH: 742
<212> TYPE: DNA
<213> ORGANISM: Rhodosporidium toruloides

<400> SEQUENCE: 63
gaactcgact cattacggga ggcgccgaca agacgatcaa ggttcgtcca ggacagccct      60
tctctgccgt cgagtttcgt tcccgctgac accctgcctt gtgcgcagat ctactctgag     120
caagcatagg tcgttccagc tgtaccggcg cggtgatcgt cgttgtgcga gtgtaacatt     180
gtgcgatacc cagcagccta tcggaggaca gcgagtgcct cgagagctgg agacgaggag     240
tcgggtgaag cgggcaaggc tggcctcgct ggatgctgag acgtcccaca gcatcgtgca     300
```

```
cgaaggagga ggggacgggc ggggacgaag cggtgttggt cgtcgggacc tcgtcgtccg      360
aaagttgggt cgtcgctccg tcgcgcggct cgcttctctc gtttccttct cttccacccg      420
ctcgctctgc ttcttgcttg aactggctca gcttggctcg ctaggaacga actactcgct      480
acactacccc aggtgcgcaa cggacttccc actctccagc tctcggacct cgacgagcga      540
aagacgaacc ccaacgacct ctcctctcgc ctgcctcgtc ttgctcagca cctaacgaca      600
cacgagcgac ccagcccgac tagactcgcg caaacctcgc aaactgaccc gcttgccatt      660
cgcctctcca gctccctctc ccgtcctcg tctccccact tcgctaccct ctcttcaaac       720
tcgtcgaata ccgcacagga tg                                               742

<210> SEQ ID NO 64
<211> LENGTH: 1010
<212> TYPE: DNA
<213> ORGANISM: Rhodosporidium toruloides

<400> SEQUENCE: 64
gaactcgact cattacggga ggcgccgaca agacgatcaa ggttcgtcca ggacagccct       60
tctctgccgt cgagtttcgt tcccgctgac accctgcctt gtgcgcagat ctactctgag      120
caagcatagg tcgttccagc tgtaccggcg cggtgatcgt cgttgtgcga gtgtaacatt      180
gtgcgatacc cagcagccta tcggaggaca gcgagtgcct cgagagctgg agacgaggag      240
tcgggtgaag cgggcaaggc tggcctcgct ggatgctgag acgtcccaca gcatcgtgca      300
cgaaggagga ggggacgggc ggggacgaag cggtgttggt cgtcgggacc tcgtcgtccg      360
aaagttgggt cgtcgctccg tcgcgcggct cgcttctctc gtttccttct cttccacccg      420
ctcgctctgc ttcttgcttg aactggctca gcttggctcg ctaggaacga actactcgct      480
acactacccc aggtgcgcaa cggacttccc actctccagc tctcggacct cgacgagcga      540
aagacgaacc ccaacgacct ctcctctcgc ctgcctcgtc ttgctcagca cctaacgaca      600
cacgagcgac ccagcccgac tagactcgcg caaacctcgc aaactgaccc gcttgccatt      660
cgcctctcca gctccctctc ccgtcctcg tctccccact tcgctaccct ctcttcaaac       720
tcgtcgaata ccgcacagga tggttgcggc gcaggagttg ccgcttgcgc tgagcatcag      780
cttcgcgccc gagtcgtcga ccatctcgat gacgctgttc aaccagcccg agacgtcgaa      840
acccgccctc cccctcgagc tcaagtacaa gtacgacccc tcgacgccgt acgcccgat       900 ccacgagatc accgaggacc gtaaccagag gatcaagcag gtgcgcgaaa ggccgttcaa      960
gcgaagggcg agcgagaact gatgaatttc tgcgcggaca gcactactcc                1010

<210> SEQ ID NO 65
<211> LENGTH: 1003
<212> TYPE: DNA
<213> ORGANISM: Rhodosporidium toruloides

<400> SEQUENCE: 65
ctgtgatgct aggtgtcgat cgagggagga ggtggacgag gagaagccag tctgagcgaa       60
gttgacatcc gcctcatctc tccctctcgc tgcgctcgtc tcgctcttca cgtcctcagc      120
ctcacaacgt cgagtaccac cagcagcaag ctcagcaact ctgcacggcg ccgcctgttc      180
gcccgagtgt tcggagcggt gggaggaact cctcggcctt tcgcagctgg tcgtccacga      240
gtcgctggag gatgaaactt tcggtcgtgg tcaacagcgt ccttacaacg tcgcgtggca      300
agtatcaagc gaaaagagcg tggtgacgag gggtgagagc ggttgaaaga agcggagggt      360
```

| | |
|---|---|
| cggagcgatt cgcggtgttg caacggcggc ggggaaagtt gcttgcgctc cgtcgtctgg | 420 |
| ctctcttgct tcctactact cgctagtacc cagtacaagc tactacaggc tatgcagact | 480 |
| cctactcgcc tgctacagct tgcgcactat gacttcgtcc ccctcctccg ctcgaccact | 540 |
| cgtcggactc gcctcacacg acggcgacaa cgcctggccg ccctcgctcc gactgggtac | 600 |
| agcagaggag gacccgctgg tggactttcg ggggtcgaga caccgcggca ctgtacttca | 660 |
| ctacgcccat cctctcgacg gtggctgtat gcggtgatgt cccctcgctc ctgggccgcc | 720 |
| tgctgtccct cggccgcagg acgcgtcctt gcgcccgttg gagcgtgtaa cttgctcgaa | 780 |
| tacgcgcatc tagcacacac gcactgctac tgagcttgca cgaggcgacc tgctcgctcg | 840 |
| ggcccccaac agcccttcac ccgcctcgtt cgacctcgac tttcctttct tccttccact | 900 |
| cctcactccg ctcacctcga gcaacctcaa acagactcgc ttcggcttct ccttccttct | 960 |
| ataccccccca accaccgacg taccaggaaa cgcagcagca atg | 1003 |

<210> SEQ ID NO 66
<211> LENGTH: 1170
<212> TYPE: DNA
<213> ORGANISM: Rhodosporidium toruloides

<400> SEQUENCE: 66

| | |
|---|---|
| ctgtgatgct aggtgtcgat cgagggagga ggtggacgag gagaagccag tctgagcgaa | 60 |
| gttgacatcc gcctcatctc tccctctcgc tgcgctcgtc tcgctcttca cgtcctcagc | 120 |
| ctcacaacgt cgagtaccac cagcagcaag ctcagcaact ctgcacggcg ccgcctgttc | 180 |
| gcccgagtgt tcggagcggt gggaggaact cctcggcctt tcgcagctgg tcgtccacga | 240 |
| gtcgctggag gatgaaactt tcggtcgtgg tcaacagcgt ccttacaacg tcgcgtggca | 300 |
| agtatcaagc gaaaagagcg tggtgacgag gggtgagagc ggttgaaaga agcggagggt | 360 |
| cggagcgatt cgcggtgttg caacggcggc ggggaaagtt gcttgcgctc cgtcgtctgg | 420 |
| ctctcttgct tcctactact cgctagtacc cagtacaagc tactacaggc tatgcagact | 480 |
| cctactcgcc tgctacagct tgcgcactat gacttcgtcc ccctcctccg ctcgaccact | 540 |
| cgtcggactc gcctcacacg acggcgacaa cgcctggccg ccctcgctcc gactgggtac | 600 |
| agcagaggag gacccgctgg tggactttcg ggggtcgaga caccgcggca ctgtacttca | 660 |
| ctacgcccat cctctcgacg gtggctgtat gcggtgatgt cccctcgctc ctgggccgcc | 720 |
| tgctgtccct cggccgcagg acgcgtcctt gcgcccgttg gagcgtgtaa cttgctcgaa | 780 |
| tacgcgcatc tagcacacac gcactgctac tgagcttgca cgaggcgacc tgctcgctcg | 840 |
| ggcccccaac agcccttcac ccgcctcgtt cgacctcgac tttcctttct tccttccact | 900 |
| cctcactccg ctcacctcga gcaacctcaa acagactcgc ttcggcttct ccttccttct | 960 |
| ataccccccca accaccgacg taccaggaaa cgcagcagca atgtcggcga aggtgcgtcg | 1020 |
| aatcgccttc ccgcgacctc gagacgacat tcctgactt ctccctccct atccctcttc | 1080 |
| tgtcctctct gcctaatcct tgatgcctct accatcccac tcgacgactc acgaacccac | 1140 |
| ccgcagccca tccgcgagta cgacgccatg | 1170 |

<210> SEQ ID NO 67
<211> LENGTH: 496
<212> TYPE: DNA
<213> ORGANISM: Rhodosporidium toruloides

<400> SEQUENCE: 67

| | |
|---|---|
| ttcgacttgt cttcctccgc gactcgttct gttgctccgc aactcccgct cttagccgcg | 60 |

```
ccgctatctc tgcgatactc agacgaaacg cttgagcttt ctgccagtcg acccgtgacg      120
attccgcccc cgcttggcgg ctacgcctct tccccgcttc tcctcgtcct ttccgagggt      180
tgttgctgcc gtcaacgtcc agcctgcgct tcactggact gccgttggag ctcaaacgct      240
actggccctc tagtcaactc gcctagcgac tccagcgcag ccctcgctct gcttcagacc      300
cttccccact tcctccccct tcttcgatct cgcaaacagc gacaacacct tccgccagcc      360
gcacgacaag cttgacttca ccctaaacct ctcatcttat cagcacaaga ccccgcgaa      420 actcgcatca gcgaccactc actccaaccg acgaacccct ccctccgacc ctccctcaca      480
tccctctttc gccatg                                                      496
```

<210> SEQ ID NO 68
<211> LENGTH: 1120
<212> TYPE: DNA
<213> ORGANISM: Rhodosporidium toruloides

<400> SEQUENCE: 68

```
ttcgacttgt cttcctccgc gactcgttct gttgctccgc aactcccgct cttagccgcg      60
ccgctatctc tgcgatactc agacgaaacg cttgagcttt ctgccagtcg acccgtgacg      120
attccgcccc cgcttggcgg ctacgcctct tccccgcttc tcctcgtcct ttccgagggt      180
tgttgctgcc gtcaacgtcc agcctgcgct tcactggact gccgttggag ctcaaacgct      240
actggccctc tagtcaactc gcctagcgac tccagcgcag ccctcgctct gcttcagacc      300
cttccccact tcctccccct tcttcgatct cgcaaacagc gacaacacct tccgccagcc      360
gcacgacaag cttgacttca ccctaaacct ctcatcttat cagcacaaga ccccgcgaa      420 actcgcatca gcgaccactc actccaaccg acgaacccct ccctccgacc ctccctcaca      480
tccctctttc gccatgtccg cgacaaagca gcacagctc ctcatcgcca accgcggcga      540
gatcgctttg cgatgcatgc gttcagctgc cgcactcaag atcccgaccg tcgccatcta      600
catggaggca gacgcatccg ctcctcacgt cttcaaagcc gatgaagcgg ctctcgttcc      660
cgcctacatc gaccaagatg ccgtcctcaa cgtctgccgc gagaagggcg tcacgatgat      720
tcacccgggc tacggcttcc tgagcgagaa cgaggcgttc gcggccaaag tcgagaaagc      780
cgggatcatc tggctcggac cgacgccgtc gcaaatcgag gcgatgggtc tcaagcacga      840
agcgcgtgct cgtgcgatca aggcggacgt ccctgtcctt ccgggctcgg aactcgtcga      900
gacgctcgac ttggcgctcg agcaggcgag caaggtcggc tacccgatcc tcctgaaggc      960
gactgcgggt ggtggaggga tgggaatgag catctgcggg agcgagggcg agctcaagaa     1020
ggcgttccag ggcacgaccg acctcagcaa ggtgcgtctt cgcttccttt tgttcaacta     1080
tctcaagctc acgctctctt ccgcgcagaa cctcttctcc                           1120
```

<210> SEQ ID NO 69
<211> LENGTH: 1006
<212> TYPE: DNA
<213> ORGANISM: Rhodosporidium toruloides

<400> SEQUENCE: 69

```
ctctagccta cgaccgcctc atcctgcgcc gcctgtcctg cagtggcgta ttgcttttcg      60
caccagctac gatctccgct ggacttcccg ggctactcct cctgggaatg ctgcgagctg     120
ttgggtgacc gagtcgggcg caaaggaggt cgggggagga atgggcggcc cgtctcgctc     180
tctcacgcct cagaacgccc agctgaagct ttgcccggac gtatgactac ttcagcgagt     240
```

```
agcccagctt tcagcaggc aaaggatgtg tgtagtgagg atcggggtgt cgacctcccc   300
ttctcctccc cctcgtcacc tctctcgctc gtcacaccac cagaatgggt ctttcaatct   360
ctcgcctgtg tcagttggtt ctctgagctc tgggcgcctt gttccagccc acctggaggc   420
ttgggggacg agattggcgc cgtcaaagcc aggagtgttg gcgcaccgtc cccgtctcg    480 cgcacgcctc tgggacggcc gctcaggatc tcgtactgac tactgaactc ctgcatgtac   540
gcctgaacca tccacgcctc tccccgccac cgccatcgct tgctgttgac cgtctcccc    600 tccaacacgc gtcgctacgt ctggctcgac ttacctgatt gcgctcactc gtcgcgcgaa   660
tggacgactg tgcactcgct tgattgccta cacccgttgt ggctgtcgac attccaggtg   720
aaggggagga ggaagggaa ggttcgaaga agaccttgca atggacggcg gtctgctccg    780
tccacagggc gttgagtctc cgtcgttccg gagcacaagc acggcgtgcg cacgttctca   840
gcgagaagga cagcaagcgt ttgcgagtga aaggggacg ttcgagttgg ccggcctgag    900
ggacttcgcc gagagcgaca ccgccttcgc cgtctcacgc tcgtcgctct ctcgctctcg   960
cgctttctga ggcttgtact gctgcagaga acgactcgct accatg                 1006

<210> SEQ ID NO 70
<211> LENGTH: 296
<212> TYPE: DNA
<213> ORGANISM: Rhodosporidium toruloides

<400> SEQUENCE: 70
gtcgcgcctt gtccgcttcc ccatcctcgt cctgctcttg ctctcttccc taccacactc    60
tcccgcttgc gggctctctt tctcgcttgg cgctcctgct accgctactc tagactctcc   120
tagtctccct gcacaaccat ccctatcccc tccgcctctc tcgcacaccc ccacagctt    180 cgttccccaa cttcacttcc gatgccgtgc gtcgcctccc tttcgcctgg cgggcccgcg   240
cctgcttccg aggacaacta ctgattgtgg gatcatgcga cgacaggttc tctggc       296

<210> SEQ ID NO 71
<211> LENGTH: 1090
<212> TYPE: DNA
<213> ORGANISM: Rhodosporidium toruloides

<400> SEQUENCE: 71
tgctcaagcg agccgataca gtcctcgaat ccggcctctc agcaatcgtc gcacaagtcg    60
tctccgccgc tttgtccgac aagtcaaagc aggactcgcc cctctcggca gcgatggtgc   120
gaacgctcgt gcttggaacg gacccgagag ggtacgcggc ggcgtgtagg gcgcttgcgg   180
gtgcgaagga cccggattac tcgagcatca aggccgagac gttgggtgcg ttcgcttgtt   240
ctccttcctc tgcttttctc ccagcaactg acgcaagcgt ctgcaacaca gtcgtcgcag   300
gcgagtttga ctacctctcg aacaaggaga cgaccgacgc gctggtcaac gacatcccgg   360
gcgcggagaa ggtccagatg gacagtgtcg gccactggca cgccgtcgag gaccccgttg   420
gactcgccaa gatcctcgat gggttcttct tgcagggaa atgaggttgg aaggggggga   480
tagactgggg agaacggcag gtgcgtacgc agcggacgtc ggtcgggagg acttttcgg    540 ggaggatatt cgctgactga ctccgacgtc gctttcctcc ttgcagtatc ttcagaaggg   600
atgggaggag gcgaactgca agggtaatga acgagacaac gccgagggag gaagcgccgg   660
aactctcggg ggcgaagaag gagtggtgtc ttcgccagcg aacagcttcc ggggtgggtt   720
ggacagcgcg agtagaattc cagcgtcgca acagagctct agtcgaccgc gatcacccac   780
aaggacgaga gcgggtcgcg ccttgtccgc ttccccatcc tcgtcctgct cttgctctct   840
```

```
tccctaccac actctcccgc ttgcgggctc tctttctcgc ttggcgctcc tgctaccgct      900
actctagact ctcctagtct ccctgcacaa ccatccctat cccctccgcc tctctcgcac      960
accccccaca gcttcgttcc ccaacttcac ttccgatgcc gtgcgtcgcc tcctttcgc      1020 ctggcgggcc cgcgcctgct tccgaggaca actactgatt gtgggatcat gcgacgacag     1080
gttctctggc                                                            1090
```

<210> SEQ ID NO 72
<211> LENGTH: 14
<212> TYPE: DNA
<213> ORGANISM: Rhodosporidium toruloides

<400> SEQUENCE: 72

```
ggcgggcccg cgcc                                                         14
```

<210> SEQ ID NO 73
<211> LENGTH: 4
<212> TYPE: PRT
<213> ORGANISM: Rhodosporidium toruloides

<400> SEQUENCE: 73

Met Pro Phe Ser
1

<210> SEQ ID NO 74
<211> LENGTH: 295
<212> TYPE: DNA
<213> ORGANISM: Rhodosporidium toruloides

<400> SEQUENCE: 74

```
cgcgccttgt ccgcttcccc atcctcgtcc tgctcttgct ctcttcccta ccacactctc       60
ccgcttgcgg gctctctttc tcgcttggcg ctcctgctac cgctactcta gactctccta      120
gtctccctgc acaaccatcc ctatcccctc cgctctctc gcacaccccc cacagcttcg       180
ttccccaact tcacttccga tcccgtgcgt cgcctccctt cgcctggcg ggcccgcgcc       240 tgcttccgag gacaactact gattgtggga tcatgcgacg acaggttctc catgg           295
```

<210> SEQ ID NO 75
<211> LENGTH: 518
<212> TYPE: DNA
<213> ORGANISM: Rhodosporidium toruloides

<400> SEQUENCE: 75

```
cacgcctctg tgactcggta cggagagaga gagcgttggg ttgggttggg gattgtggcg       60
agcgaagggc gacccagcag ccaggggagg ggagttggtc tggatgcaaa ccatgcgcat      120
ctcctctcgc agttgaatcg ttttccgc tctgccctcg ctctctcttc cttctgctct        180
ttactcgctc acgaacaaca acgagccaca cagcgtgagc acacaccgct gcactcactc      240
gctgtcacgg accgcagctc acccttatcg tcactccctc tcccaccgca cagcctcact      300
ccctctctcg ctctccctca caagcacaac acacggcaca ctcgcacgca cactcgcacg      360
caatcgccac cgtcaacgag aagcagcccg ccaccgacgc gccctcgcg cacgagaccg       420 ccatccaccg cgtgcgtccc catccctccc actgtcttcc tcgtgaaacc cgctcacccg      480
ttcgcaagca cacacgcagg tgtcggacta ccccatgg                              518
```

<210> SEQ ID NO 76
<211> LENGTH: 1014

```
<212> TYPE: DNA
<213> ORGANISM: Rhodosporidium toruloides

<400> SEQUENCE: 76
gaactcgact cattacggga ggcgccgaca agacgatcaa ggttcgtcca ggacagccct      60
tctctgccgt cgagtttcgt tcccgctgac accctgcctt gtgcgcagat ctactctgag     120
caagcatagg tcgttccagc tgtaccggcg cggtgatcgt cgttgtgcga gtgtaacatt     180
gtgcgatacc cagcagccta tcggaggaca gcgagtgcct cgagagctgg agacgaggag     240
tcgggtgaag cgggcaaggc tggcctcgct ggatgctgag acgtcccaca gcatcgtgca     300
cgaaggagga ggggacgggc ggggacgaag cggtgttggt cgtcgggacc tcgtcgtccg     360
aaagttgggt cgtcgctccg tcgcgcggct cgcttctctc gtttccttct cttccacccg     420
ctcgctctgc ttcttgcttg aactggctca gcttggctcg ctaggaacga actactcgct     480
acactacccc aggtgcgcaa cggacttccc actctccagc tctcggacct cgacgagcga     540
aagacgaacc ccaacgacct ctcctctcgc ctgcctcgtc ttgctcagca cctaacgaca     600
cacgagcgac ccagcccgac tagactcgcg caaacctcgc aaactgaccc gcttgccatt     660
cgcctctcca gctccctctc cccgtcctcg tctccccact tcgctaccct ctcttcaaac     720
tcgtcgaata ccgcacagga tcgttgcggc gcaggagttg ccgcttgcgc tgagcatcag     780
cttcgcgccc gagtcgtcga ccatctcgat gacgctgttc aaccagcccg agacgtcgaa     840
acccgccctc cccctcgagc tcaagtacaa gtacgacccc tcgacgccgt acgccccgat     900
ccacgagatc accgaggacc gtaaccgagg gatcaagcag gtgcgcgaaa ggccgttcaa     960
gcgaagggcg agcgagaact gatgaatttc tgcgcggaca gcactactcc atgg          1014

<210> SEQ ID NO 77
<211> LENGTH: 297
<212> TYPE: DNA
<213> ORGANISM: Rhodosporidium toruloides

<400> SEQUENCE: 77
gtcgcgcctt gtccgcttcc ccatcctcgt cctgctcttg ctctcttccc taccacactc      60
tcccgcttgc gggctctctt tctcgcttgg cgctcctgct accgctactc tagactctcc     120
tagtctccct gcacaaccat ccctatcccc tccgcctctc tcgcacaccc ccacagcctt     180
cgttccccaa cttcacttcc gatcccgtgc gtcgcctccc tttcgcctgg cgggcccgcg     240
cctgcttccg aggacaacta ctgattgtgg gatcatgcga cgacaggttc tccatgg          297

<210> SEQ ID NO 78
<211> LENGTH: 44
<212> TYPE: PRT
<213> ORGANISM: Rhodosporidium toruloides

<400> SEQUENCE: 78

Met Ala Thr Val Asn Glu Lys Gln Pro Ala Thr Asp Ala Pro Leu Ala
1               5                   10                  15

His Glu Thr Ala Ile His Arg Val Ser Asp Tyr Pro Val Ile Lys Asp
            20                  25                  30

Thr Leu Ser Ser Leu Asp Ser Tyr Ala His Ser His
        35                  40

<210> SEQ ID NO 79
<211> LENGTH: 1171
<212> TYPE: DNA
<213> ORGANISM: Rhodosporidium toruloides
```

<400> SEQUENCE: 79

```
ctgtgatgct aggtgtcgat cgagggagga ggtggacgag gagaagccag tctgagcgaa    60
gttgacatcc gcctcatctc tccctctcgc tgcgctcgtc tcgctcttca cgtcctcagc   120
ctcacaacgt cgagtaccac cagcagcaag ctcagcaact ctgcacggcg ccgcctgttc   180
gcccgagtgt tcggagcggt gggaggaact cctcggcctt tcgcagctgg tcgtccacga   240
gtcgctggag gatgaaactt tcggtcgtgg tcaacagcgt ccttacaacg tcgcgtggca   300
agtatcaagc gaaaagagcg tggtgacgag gggtgagagc ggttgaaaga agcggagggt   360
cggagcgatt cgcggtgttg caacggcggc ggggaaagtt gcttgcgctc cgtcgtctgg   420
ctctcttgct tcctactact cgctagtacc cagtacaagc tactacaggc tatgcagact   480
cctactcgcc tgctacagct tgcgcactat gacttcgtcc ccctcctccg ctcgaccact   540
cgtcggactc gcctcacacg acggcgacaa cgcctggccg ccctcgctcc gactgggtac   600
agcagaggag gacccgctgg tggactttcg ggggtcgaga caccgcggca ctgtacttca   660
ctacgcccat cctctcgacg gtggctgtat gcggtgatgt ccctcgctc ctgggccgcc     720
tgctgtccct cggccgcagg acgcgtcctt cgcccgttg gagcgtgtaa cttgctcgaa    780
tacgcgcatc tagcacacac gcactgctac tgagcttgca cgaggcgacc tgctcgctcg   840
ggcccccaac agcccttcac ccgcctcgtt cgacctcgac tttccttttct tccttccact   900
cctcactccg ctcacctcga gcaacctcaa acagactcgc ttcggcttct ccttccttct   960
atacccccca accaccgacg taccaggaaa cgcagcagca atctcggcga aggtgcgtcg  1020
aatcgccttc ccgcgacctc gagacgacat tcctgacttt ctccctccct atccctcttc  1080
tgtcctctct gcctaatcct tgatgcctct accatcccac tcgacgactc acgaacccac  1140
ccgcagccca tccgcgagta cgacgccatg g                                 1171
```

<210> SEQ ID NO 80
<211> LENGTH: 1091
<212> TYPE: DNA
<213> ORGANISM: Rhodosporidium toruloides

<400> SEQUENCE: 80

```
tgctcaagcg agccgataca gtcctcgaat ccggcctctc agcaatcgtc gcacaagtcg    60
tctccgccgc tttgtccgac aagtcaaagc aggactcgcc cctctcggca gcgatggtgc   120
gaacgctcgt gcttggaacg gacccgagag ggtacgcggc ggcgtgtagg gcgcttgcgg   180
gtgcgaagga cccggattac tcgagcatca aggccgagac gttgggtgcg ttcgcttgtt   240
ctccttcctc tgcttttctc ccagcaactg acgcaagcgt ctgcaacaca gtcgtcgcag   300
gcgagtttga ctacctctcg aacaaggaga cgaccgacgc gctggtcaac gacatcccgg   360
gcgcggagaa ggtccagatg gacagtgtcg gccactggca cgccgtcgag gaccccgttg   420
gactcgccaa gatcctcgat gggttcttct tgcaggggaa atgaggttgg aagggggga    480
tagactgggg agaacggcag gtgcgtacgc agcggacgtc ggtcgggagg acttttttcgg   540
ggaggatatt cgctgactga ctccgacgtc gctttcctcc ttgcagtatc ttcagaaggg   600
atgggaggag gcgaactgca agggtaatga acgagacaac gccgagggag gaagcgccgg   660
aactctcggg ggcgaagaag gagtggtgtc ttcgccagcg aacagcttcc ggggtgggtt   720
ggacagcgcc agtagaattc cagcgtcgca acagagctct agtcgaccgc gatcacccac   780
aaggacgaga gcgggtcgcg ccttgtccgc ttccccatcc tcgtcctgct cttgctctct   840
```

```
tccctaccac actctcccgc ttgcgggctc tctttctcgc ttggcgctcc tgctaccgct    900
actctagact ctcctagtct ccctgcacaa ccatccctat cccctccgcc tctctcgcac    960 acccccaca gcttcgttcc ccaacttcac ttccgatccc gtgcgtcgcc tcccttttcgc   1020 ctggcgggcc cgcgcctgct tccgaggaca actactgatt gtgggatcat gcgacgacag   1080
gttctccatg g                                                       1091
```

<210> SEQ ID NO 81
<211> LENGTH: 297
<212> TYPE: DNA
<213> ORGANISM: Rhodosporidium toruloides

<400> SEQUENCE: 81

```
gtcgcgcctt gtccgcttcc ccatcctcgt cctgctcttg ctctcttccc taccacactc     60
tcccgcttgc gggctctctt tctcgcttgg cgctcctgct accgctactc tagactctcc    120
tagtctccct gcacaaccat ccctatcccc tccgcctctc tcgcacaccc ccacagcttc    180
cgttccccaa cttcacttcc gatgccgtgc gtcgcctccc tttcgcctgg cgggcccgcg    240
cctgcttccg aggacaacta ctgattgtgg gatcatgcga cgacaggttc tccatgg      297
```

<210> SEQ ID NO 82
<211> LENGTH: 297
<212> TYPE: DNA
<213> ORGANISM: Rhodosporidium toruloides

<400> SEQUENCE: 82

```
gtcgggcctt gtctccttcc ccatcctcga cctcctcctg ctctcttccc taccacactc     60
tcccgcttgc gggctttctt tctcgcttgg cgctcttgct accgctactc tagactctcc    120
tagtctccct gcacaacaac cctgctccct cccgcctctc tcgcacaccc ccacagcttc    180
cgttccccaa cttcacttcc gatgccgtgc gtcgcctccc tttcgcctag cgggcctgcg    240
cctgcttctg agaacgactg ctgactgtgg aatgatttgc cgacagattc tccatgg      297
```

<210> SEQ ID NO 83
<211> LENGTH: 297
<212> TYPE: DNA
<213> ORGANISM: Rhodosporidium toruloides

<400> SEQUENCE: 83

```
gtcgggcctt gtctccttcc ccatcctcga cctcctcctg ctctcttccc taccacactc     60
tcccgcttgc gggctttctt tctcgcttgg cgctcttgct accgctactc tagactctcc    120
tagtctccct gcacaacaac cctgctccct cccgcctctc tcgcacaccc ccacagcttc    180
cgttccccaa cttcacttcc gatcccgtgc gtcgcctccc tttcgcctag cgggcctgcg    240
cctgcttctg agaacgactg ctgactgtgg aatgatttgc cgacagattc tccatgg      297
```

<210> SEQ ID NO 84
<211> LENGTH: 409
<212> TYPE: DNA
<213> ORGANISM: Rhodosporidium toruloides

<400> SEQUENCE: 84

```
gttggggaaa gtggcgagcg agcgaagggc gacttggaag tgaagagagt tgggagctgg     60
tccggatgca aaccatgcgc atctcgttcg tcgtgcaatc gttttttccg ccttctcgct    120
cttctcgctc tctctcttgc tcttcactcg cttgtaagca aacaacgagc acagcgacac    180
agcgtgagca cactcgctcg cactcgcact gactcgggca gctcaccctt atcgtcatcc    240
```

```
cacccgcaca gcctcactct cctctctctt tcacacacgc actcaaaaca cgcacgcacg    300
caagatggcc accgtcaacg agaagcagcc cgccaccgac gcgcccctcg cgcacgagac    360
cgccatccac cgcgtgcgtc cccatctctt cctcgtgaaa acccgctca                409

<210> SEQ ID NO 85
<211> LENGTH: 452
<212> TYPE: DNA
<213> ORGANISM: Rhodosporidium toruloides

<400> SEQUENCE: 85
gttggggaaa gtggcgagcg agcgaagggc gacttggaag tgaagagagt tgggagctgg     60
tccggatgca aaccatgcgc atctcgttcg tcgtgcaatc gttttccccg ccttctcgct    120
cttctcgctc tctctcttgc tcttcactcg cttgtaagca aacaacgagc acagcgacac    180
agcgtgagca cactcgctcg cactcgcact gactcgggca gctcacccctt atcgtcatcc    240 cacccgcaca gcctcactct cctctctctt tcacacacgc actcaaaaca cgcacgcacg    300
caagatcgcc accgtcaacg agaagcagcc cgccaccgac gcgcccctcg cgcacgagac    360
cgccatccac cgcgtgcgtc cccatctctt cctcgtgaaa acccgctcaa caactcacac    420
acgtgcaaca cagggctcgg actaccccat gg                                  452

<210> SEQ ID NO 86
<211> LENGTH: 988
<212> TYPE: DNA
<213> ORGANISM: Rhodosporidium toruloides

<400> SEQUENCE: 86
actcggctca tcacgggagg cgccgacaag acgaccaagg tgcgtccaag acggactcct     60
tctccgatcc cgctgacatt ctgcctcgcg cacgcagatc tattctgagc aagcatgagg    120
ccgttccacc tgaaccggcg aggtggtccc cgtcgtgaga gtgtaatatc gttgcgatac    180
ccatgcagcc tcggaggaca tcgagcgcga cgagagtggg agaacgagga gccggttgaa    240
gcggacacgg ttggcctcgc tggatgctgc aagtcgcaca gcactgtgct caaaagacga    300
ggagacgagc gagacggagc ggtgttggac gagggacctc gtcgtccgaa agttgggtcg    360
ctcggctcgc ttccgcttct tcctcccgct cactctgctt cttgctcgac tggctctcgc    420
ttggtctcgc taggaacgaa actacctcgc taaactaccc aggtgcgcag cgactttccc    480
gatcgcgact ctccgacctc gacgagcgaa gacgaacccc aacgactctc ctctcgcttc    540
cttcttcccg ctcagcgccg cagcgacgtg cgcacgacca atccagtccg agtggactcg    600
agcgaacctc gcactgaccc gcttgccgtt cgcctctcca gctttctcct cccgctcctc    660
ctctccccac ttcgctacca ctcttcaaac gactcgtcaa acaccgcaca ggatcgtcgc    720
ggcgcaggac ttgccgctcg cgctgagcat cagcttcgcg cccgagtcgt cgaccatctc    780
gatgacgctg ttcaaccagc ccgaggcgtc gaaacccgcc ctcccctcg agctcaagta    840 caagtacgac ccctcgacgc cgtacgcccc gatccacgag atcaccgagg accgtaatca    900
gaggatcaag caggtgcgcg cgcggccgtt tgagcgagag acgggcgaga aactgatcaa    960
tttccggttc gacagcacta ctccatgg                                       988

<210> SEQ ID NO 87
<211> LENGTH: 294
<212> TYPE: DNA
<213> ORGANISM: Rhodosporidium toruloides
```

```
<400> SEQUENCE: 87
cgcgccttgt ccgcttcccc atcctcgtcc tgctcttgct ctcttcccta ccacactctc      60
ccgcttgcgg gctctctttc tcgcttggcg ctcctgctac cgctactcta gactctccta     120
gtctccctgc acaaccatcc ctatcccctc cgctctctc gcacaccccc acagcttcg       180 ttccccaact tcacttccga tcccgtgcgt cgcctcccctt tcgcctggcg ggcccgcgcc    240
tgcttccgag gacaactact gattgtggga tcatgcgacg acaggttctc catg            294

<210> SEQ ID NO 88
<211> LENGTH: 296
<212> TYPE: DNA
<213> ORGANISM: Rhodosporidium toruloides

<400> SEQUENCE: 88
gtcgcgcctt gtccgcttcc ccatcctcgt cctgctcttg ctctcttccc taccacactc      60
tcccgcttgc gggctctctt tctcgcttgg cgctcctgct accgctactc tagactctcc     120
tagtctccct gcacaaccat ccctatcccc tccgctctc tcgcacaccc ccacagctt      180 cgttccccaa cttcacttcc gatcccgtgc gtcgcctccc tttcgcctgg cgggcccgcg     240
cctgcttccg aggacaacta ctgattgtgg gatcatgcga cgacaggttc tccatg         296

<210> SEQ ID NO 89
<211> LENGTH: 1090
<212> TYPE: DNA
<213> ORGANISM: Rhodosporidium toruloides

<400> SEQUENCE: 89
tgctcaagcg agccgataca gtcctcgaat ccggcctctc agcaatcgtc gcacaagtcg      60
tctccgccgc tttgtccgac aagtcaaagc aggactcgcc cctctcggca gcgatggtgc     120
gaacgctcgt gcttggaacg gacccgagag ggtacgcggc ggcgtgtagg gcgcttgcgg     180
gtgcgaagga cccggattac tcgagcatca aggccgagac gttgggtgcg ttcgcttgtt     240
ctccttcctc tgcttttctc ccagcaactg acgcaagcgt ctgcaacaca gtcgtcgcag     300
gcgagtttga ctacctctcg aacaaggaga cgaccgacgc gctggtcaac gacatcccgg     360
gcgcggagaa ggtccagatg gacagtgtcg gccactggca cgccgtcgag gaccccgttg     420
gactcgccaa gatcctcgat gggttcttct gcaggggaa atgaggttgg aagggggga      480 tagactgggg agaacggcag gtgcgtacgc agcggacgtc ggtcgggagg acttttttcgg    540 ggaggatatt cgctgactga ctccgacgtc gctttcctcc ttgcagtatc ttcagaaggg     600
atgggaggag gcgaactgca agggtaatga acagacaac gccgagggag gaagcgccgg     660
aactctcggg ggcgaagaag gagtggtgtc ttcgccagcg aacagcttcc ggggtgggtt     720
ggacagcgcc agtagaattc cagcgtcgca acagagctct agtcgaccgc gatcacccac     780
aaggacgaga gcgggtcgcg ccttgtccgc ttccccatcc tcgtcctgct cttgctctct     840
tccctaccac actctcccgc ttgcgggctc tctttctcgc ttggcgctcc tgctaccgct     900
actctagact ctcctagtct ccctgcacaa ccatccctat cccctccgcc tctctcgcac     960
accccccaca gcttcgttcc ccaacttcac ttccgatccc gtgcgtcgcc tccctttcgc    1020
ctggcgggcc cgcgcctgct tccgaggaca actactgatt gtgggatcat gcgacgacag    1080
gttctccatg                                                           1090

<210> SEQ ID NO 90
<211> LENGTH: 296
```

<212> TYPE: DNA
<213> ORGANISM: Rhodosporidium toruloides

<400> SEQUENCE: 90

```
gtcgcgcctt gtccgcttcc ccatcctcgt cctgctcttg ctctcttccc taccacactc    60
tcccgcttgc gggctctctt tctcgcttgg cgctcctgct accgctactc tagactctcc   120
tagtctccct gcacaaccat ccctatcccc tccgcctctc tcgcacaccc cccacagctt   180
cgttccccaa cttcacttcc gatgccgtgc gtcgcctccc tttcgcctgg cgggcccgcg   240
cctgcttccg aggacaacta ctgattgtgg gatcatgcga cgacaggttc tccatg       296
```

<210> SEQ ID NO 91
<211> LENGTH: 296
<212> TYPE: DNA
<213> ORGANISM: Rhodosporidium toruloides

<400> SEQUENCE: 91

```
gtcgggcctt gtctccttcc ccatcctcga cctcctcctg ctctcttccc taccacactc    60
tcccgcttgc gggctttctt tctcgcttgg cgctcttgct accgctactc tagactctcc   120
tagtctccct gcacaacaac cctgctccct ccgcctctc tcgcacaccc cccacagctt    180
cgttccccaa cttcacttcc gatgccgtgc gtcgcctccc tttcgcctag cgggcctgcg   240
cctgcttctg agaacgactg ctgactgtgg aatgatttgc cgacagattc tccatg       296
```

<210> SEQ ID NO 92
<211> LENGTH: 296
<212> TYPE: DNA
<213> ORGANISM: Rhodosporidium toruloides

<400> SEQUENCE: 92

```
gtcgggcctt gtctccttcc ccatcctcga cctcctcctg ctctcttccc taccacactc    60
tcccgcttgc gggctttctt tctcgcttgg cgctcttgct accgctactc tagactctcc   120
tagtctccct gcacaacaac cctgctccct ccgcctctc tcgcacaccc cccacagctt    180
cgttccccaa cttcacttcc gatccgtgc gtcgcctccc tttcgcctag cgggcctgcg    240
cctgcttctg agaacgactg ctgactgtgg aatgatttgc cgacagattc tccatg       296
```

<210> SEQ ID NO 93
<211> LENGTH: 517
<212> TYPE: DNA
<213> ORGANISM: Rhodosporidium toruloides

<400> SEQUENCE: 93

```
cacgcctctg tgactcggta cggagagaga gagcgttggg ttgggttggg gattgtggcg    60
agcgaagggc gacccagcag ccagggagag ggagttggtc tggatgcaaa ccatgcgcat   120
ctcctctcgc agttgaatcg ttttccccgc tctgccctcg ctctctcttc cttctgctct   180
ttactcgctc acgaacaaca acgagccaca cagcgtgagc acacaccgct gcactcactc   240
gctgtcacgg accgcagctc acccttatcg tcactccctc tcccaccgca cagcctcact   300
ccctctctcg ctctccctca caagcacaac acacggcaca ctcgcacgca cactcgcacg   360
caatcgccac cgtcaacgag aagcagcccg ccaccgacgc gccctcgcg cacgagaccg    420
ccatccaccg cgtgcgtccc catccctccc actgtcttcc tcgtgaaacc cgctcacccg   480
ttcgcaagca cacacgcagg tgtcggacta ccccatg                             517
```

<210> SEQ ID NO 94

<211> LENGTH: 451
<212> TYPE: DNA
<213> ORGANISM: Rhodosporidium toruloides

<400> SEQUENCE: 94

```
gttgggaaaa gtggcgagcg agcgaagggc gacttggaag tgaagagagt tgggagctgg      60
tccggatgca aaccatgcgc atctcgttcg tcgtgcaatc gttttccccg ccttctcgct     120
cttctcgctc tctctcttgc tcttcactcg cttgtaagca aacaacgagc acagcgacac     180
agcgtgagca cactcgctcg cactcgcact gactcgggca gctcacccct tatcgtcatcc    240
cacccgcaca gcctcactct cctctctctt tcacacacgc actcaaaaca cgcacgcacg     300
caagatcgcc accgtcaacg agaagcagcc cgccaccgac gcgcccctcg cgcacgagac     360
cgccatccac cgcgtgcgtc cccatctctt cctcgtgaaa acccgctcaa caactcacac     420
acgtgcaaca cagggctcgg actaccccat g                                    451
```

<210> SEQ ID NO 95
<211> LENGTH: 1013
<212> TYPE: DNA
<213> ORGANISM: Rhodosporidium toruloides

<400> SEQUENCE: 95

```
gaactcgact cattacggga ggcgccgaca agacgatcaa ggttcgtcca ggacagccct      60
tctctgccgt cgagtttcgt tcccgctgac accctgcctt gtgcgcagat ctactctgag     120
caagcatagg tcgttccagc tgtaccggcg cggtgatcgt cgttgtgcga gtgtaacatt     180
gtgcgatacc cagcagccta tcggaggaca gcgagtgcct cgagagctgg agacgaggag     240
tcgggtgaag cgggcaaggc tggcctcgct ggatgctgag acgtcccaca gcatcgtgca     300
cgaaggagga ggggacgggc ggggacgaag cggtgttggt cgtcgggacc tcgtcgtccg     360
aaagttgggt cgtcgctccg tcgcgcggct cgcttctctc gtttccttct cttccacccg     420
ctcgctctgc ttcttgcttg aactggctca gcttggctcg ctaggaacga actactcgct     480
acactacccc aggtgcgcaa cggacttccc actctccagc tctcggacct cgacgagcga     540
aagacgaacc ccaacgacct ctcctctcgc ctgcctcgtc ttgctcagca cctaacgaca     600
cacgagcgac ccagcccgac tagactcgcg caaacctcgc aaactgaccc gcttgccatt     660
cgcctctcca gctccctctc ccgtcctcg tctccccact tcgctaccct ctcttcaaac     720
tcgtcgaata ccgcacagga tcgttgcggc gcaggagttg ccgcttgcgc tgagcatcag     780
cttcgcgccc gagtcgtcga ccatctcgat gacgctgttc aaccagcccg agacgtcgaa     840
acccgccctc cccctcgagc tcaagtacaa gtacgacccc tcgacgccgt acgccccgat     900
ccacgagatc accgaggacc gtaaccgag atcaagcag gtgcgcgaaa ggccgttcaa      960
gcgaagggcg agcgagaact gatgaatttc tgcgcggaca gcactactcc atg           1013
```

<210> SEQ ID NO 96
<211> LENGTH: 987
<212> TYPE: DNA
<213> ORGANISM: Rhodosporidium toruloides

<400> SEQUENCE: 96

```
actcggctca tcacgggagg cgccgacaag acgaccaagg tgcgtccaag acggactcct      60
tctccgatcc cgctgacatt ctgcctcgcg cacgcagatc tattctgagc aagcatgagg     120
ccgttccacc tgaaccggcg aggtggtccc cgtcgtgaga gtgtaatatc gttgcgatac     180
ccatgcagcc tcggaggaca tcgagcgcga cgagagtggg agaacgagga gccggttgaa     240
```

```
gcggacacgg ttggcctcgc tggatgctgc aagtcgcaca gcactgtgct caaaagacga      300
ggagacgagc gagacggagc ggtgttggac gagggacctc gtcgtccgaa agttgggtcg      360
ctcggctcgc ttccgcttct tcctcccgct cactctgctt cttgctcgac tggctctcgc      420
ttggtctcgc taggaacgaa actacctcgc taaactaccc aggtgcgcag cgactttccc      480
gatcgcgact ctccgacctc gacgagcgaa gacgaacccc aacgactctc ctctcgcttc      540
cttcttcccg ctcagcgccg cagcgacgtg cgcacgacca atccagtccg agtggactcg      600
agcgaacctc gcactgaccc gcttgccgtt cgcctctcca gctttctcct cccgctcctc      660
ctctccccac ttcgctacca ctcttcaaac gactcgtcaa acaccgcaca ggatcgtcgc      720
ggcgcaggac ttgccgctcg cgctgagcat cagcttcgcg cccgagtcgt cgaccatctc      780
gatgacgctg ttcaaccagc ccgaggcgtc gaaacccgcc ctcccctcg agctcaagta       840 caagtacgac ccctcgacgc cgtacgcccc gatccacgag atcaccgagg accgtaatca      900
gaggatcaag caggtgcgcg cgcggccgtt tgagcgagag acgggcgaga aactgatcaa      960
tttccggttc gacagcacta ctccatg                                         987
```

<210> SEQ ID NO 97
<211> LENGTH: 1170
<212> TYPE: DNA
<213> ORGANISM: Rhodosporidium toruloides

<400> SEQUENCE: 97

```
ctgtgatgct aggtgtcgat cgagggagga ggtggacgag gagaagccag tctgagcgaa       60
gttgacatcc gcctcatctc tccctctcgc tgcgctcgtc tcgctcttca cgtcctcagc      120
ctcacaacgt cgagtaccac cagcagcaag ctcagcaact ctgcacggcg ccgcctgttc      180
gcccgagtgt tcggagcggt gggaggaact cctcggcctt tcgcagctgg tcgtccacga      240
gtcgctggag gatgaaactt tcggtcgtgg tcaacagcgt ccttacaacg tcgcgtggca      300
agtatcaagc gaaaagagcg tggtgacgag gggtgagagc ggttgaaaga agcggagggt      360
cggagcgatt cgcggtgttg caacggcggc ggggaaagtt gcttgcgctc cgtcgtctgg      420
ctctcttgct tcctactact cgctagtacc cagtacaagc tactacaggc tatgcagact      480
cctactcgcc tgctacagct tgcgcactat gacttcgtcc ccctcctccg ctcgaccact      540
cgtcggactc gcctcacacg acggcgacaa cgcctggccg ccctcgctcc gactgggtac      600
agcagaggag gacccgctgg tggactttcg ggggtcgaga caccgcggca ctgtacttca      660
ctacgcccat cctctcgacg gtggctgtat gcggtgatgt cccctcgctc ctgggccgcc      720
tgctgtccct cggccgcagg acgcgtcctt gcgcccgttg gagcgtgtaa cttgctcgaa      780
tacgcgcatc tagcacacac gcactgctac tgagcttgca cgaggcgacc tgctcgctcg      840
ggcccccaac agcccttcac ccgcctcgtt cgacctcgac tttcctttct tccttccact      900
cctcactccg ctcacctcga gcaacctcaa acagactcgc ttcggcttct ccttccttct      960
atacccccca accaccgacg taccaggaaa cgcagcagca atctcggcga aggtgcgtcg     1020
aatcgccttc ccgcgacctc gagacgacat tcctgacttt ctccctccct atccctcttc     1080
tgtcctctct gcctaatcct tgatgcctct accatcccac tcgacgactc acgaacccac     1140
ccgcagccca tccgcgagta cgacgccatg                                      1170
```

<210> SEQ ID NO 98
<211> LENGTH: 29
<212> TYPE: DNA

<213> ORGANISM: Rhodosporidium toruloides

<400> SEQUENCE: 98
tttactagtg cacgcgaagc ggtagaagc  29

<210> SEQ ID NO 99
<211> LENGTH: 30
<212> TYPE: DNA
<213> ORGANISM: Rhodosporidium toruloides

<400> SEQUENCE: 99
tttccatgga tcccccccag tacacagtac  30

<210> SEQ ID NO 100
<211> LENGTH: 26
<212> TYPE: DNA
<213> ORGANISM: Rhodosporidium toruloides

<400> SEQUENCE: 100
tttccatgga gtcgacgtgg cctgcg  26

<210> SEQ ID NO 101
<211> LENGTH: 41
<212> TYPE: DNA
<213> ORGANISM: Rhodosporidium toruloides

<400> SEQUENCE: 101
gtgtactggg ggggatagat cggcaaggaa aagggacacg t  41

<210> SEQ ID NO 102
<211> LENGTH: 41
<212> TYPE: DNA
<213> ORGANISM: Rhodosporidium toruloides

<400> SEQUENCE: 102
acgtgtccct tttccttgcc gatctatccc ccccagtaca c  41

<210> SEQ ID NO 103
<211> LENGTH: 27
<212> TYPE: DNA
<213> ORGANISM: Rhodosporidium toruloides

<400> SEQUENCE: 103
tttactagtg gcaaacacag caacgac  27

<210> SEQ ID NO 104
<211> LENGTH: 27
<212> TYPE: DNA
<213> ORGANISM: Rhodosporidium toruloides

<400> SEQUENCE: 104
tttactagtc gttcttcgac gtccgag  27

<210> SEQ ID NO 105
<211> LENGTH: 25
<212> TYPE: DNA
<213> ORGANISM: Rhodosporidium toruloides

<400> SEQUENCE: 105
tttactagtg gctgggtgtg cggag  25

<210> SEQ ID NO 106
<211> LENGTH: 28

```
<212> TYPE: DNA
<213> ORGANISM: Rhodosporidium toruloides

<400> SEQUENCE: 106
tttactagtg cacctcgcgt caaccctc                                              28

<210> SEQ ID NO 107
<211> LENGTH: 1150
<212> TYPE: DNA
<213> ORGANISM: Rhodosporidium toruloides

<400> SEQUENCE: 107
gcacgcgaag cggtagaagc aatgaagcga ggcgagagcg agagaggcag ggcttcagcc    60
atgtccagct gatcggctgt aacgtcgcgc cgggccagtc tgttgaattt gttgcgtcgc   120
ctgagcgtaa tagaagtgca gtagtctact ccgcatgccg agaacgtcga agagcgcgaa   180
gtagggagtc gagggaagcg agggtggcaa acacagcaac gacaagcggt tccgcttcgc   240
tcaaaagctc gttgacgttg ttttgacgtt ttgaagacag tacaacagca gcaagaggcg   300
tgcgaagcgt tggtggcgag agcagcgaca aggagggagg aatgagggag tggtggcgag   360
ggctcgcaaa cgggcgtacg cctcgaatgg agacgtgcga gtcgttcttc gacgtccgag   420
ggatgccgag cgccgagacg gagcacgcaa cgagcgagag gagagcagcc gcgcaaggtg   480
attcgagtgg cgcaagcgga ggacgacgag gagacgacg agggaggagg agggatggcg   540
agcgagcatc ggacggcggg gcgcgagaga cggcgtgagg agccgggtgt ggagagtttg   600
aggaggcgcg ggatgcgaag tggctgggtg tgcggagtga gcggtggcaa agagcgcact   660
tagagtctag agcgaggcag tagtagtaga gctgtatgaa tgaatacaaa gtgtgaatac   720
aacagtttgt aatgcgattc tgagcttgga cgtgtgcgcg cgagagggcg acttgcaagc   780
cagcgcccgc tcgctcttct tccttctgca cctcgcgtca accctcgcat ctcacaccta   840
cactcgcatt caaagtgcgt acactctccc acgacacacg gggacggcgc acaccaccgc   900
gcgtcgcttg aacggcgtcg ccacttcgag ccgtcactga cttcgtcctc gtcctccctc   960
ctctactctc ttgtactgta ctgtgtactg gggggggatag atgggcaagg aaaagggaca  1020
cgtcaacgtc gtcgttatcg gtacgttcag cgtcgtcgag gcgagtctgg cgaggaggag  1080
gacgtcgagc tgacctcgcc ccgtcctccc gcgcaggcca cgtcgactcc ggcaagtcga  1140
ccaccaccgg                                                         1150

<210> SEQ ID NO 108
<211> LENGTH: 13
<212> TYPE: PRT
<213> ORGANISM: Rhodosporidium toruloides

<400> SEQUENCE: 108

Met Gly Lys Glu Lys Gly His Val Asn Val Val Val Ile
1               5                   10

<210> SEQ ID NO 109
<211> LENGTH: 12
<212> TYPE: PRT
<213> ORGANISM: Rhodosporidium toruloides

<400> SEQUENCE: 109

Gly His Val Asp Ser Gly Lys Ser Thr Thr Thr Gly
1               5                   10

<210> SEQ ID NO 110
```

```
<211> LENGTH: 1000
<212> TYPE: DNA
<213> ORGANISM: Rhodosporidium toruloides

<400> SEQUENCE: 110
gcacgcgaag cggtagaagc aatgaagcga ggcgagagcg agagaggcag ggcttcagcc      60
atgtccagct gatcggctgt aacgtcgcgc cgggccagtc tgttgaattt gttgcgtcgc     120
ctgagcgtaa tagaagtgca gtagtctact ccgcatgccg agaacgtcga agagcgcgaa     180
gtagggagtc gagggaagcg agggtggcaa acacagcaac gacaagcggt tccgcttcgc     240
tcaaaagctc gttgacgttg ttttgacgtt ttgaagacag tacaacagca gcaagaggcg     300
tgcgaagcgt tggtggcgag agcagcgaca aggagggagg aatgagggag tggtggcgag     360
ggctcgcaaa cgggcgtacg cctcgaatgg agacgtgcga gtcgttcttc gacgtccgag     420
ggatgccgag cgccgagacg gagcacgcaa cgagcgagag gagagcagcc gcgcaaggtg     480
attcgagtgg cgcaagcgga ggacgacgag gagacggacg agggaggagg agggatggcg     540
agcgagcatc ggacggcggg gcgcgagaga cggcgtgagg agccgggtgt ggagagtttg     600
aggaggcgcg ggatgcgaag tggctgggtg tgcggagtga gcggtggcaa agagcgcact     660
tagagtctag agcgaggcag tagtagtaga gctgtatgaa tgaatacaaa gtgtgaatac     720
aacagtttgt aatgcgattc tgagcttgga cgtgtgcgcg cgagagggcg acttgcaagc     780
cagcgcccgc tcgctcttct tccttctgca cctcgcgtca accctcgcat ctcacaccta     840
cactcgcatt caaagtgcgt acactctccc acgacacacg gggacggcgc acaccaccgc     900
gcgtcgcttg aacggcgtcg ccacttcgag ccgtcactga cttcgtcctc gtcctccctc     960
ctctactctc ttgtactgta ctgtgtactg gggggggatag                         1000

<210> SEQ ID NO 111
<211> LENGTH: 2142
<212> TYPE: DNA
<213> ORGANISM: Rhodosporidium toruloides

<400> SEQUENCE: 111
atgggcaagg aaaagggaca cgtcaacgtc gtcgttatcg gtacgttcag cgtcgtcgag      60
gcgagtctgg cgaggaggag gacgtcgagc tgacctcgcc ccgtcctccc gcgcaggcca     120
cgtcgactcc ggcaagtcga ccaccaccgg acacttgatc tacaagtgcg gcggtatcga     180
caagcgtacc atcgagaagt tgtgcgtcga aaatcgttct ctgcctccca gcccgctcgg     240
acccccaagct gaccctcgca ctctcgtccc acagcgagaa ggaggccgct gagctcggca     300
agggtgagtc gtggtccagc tcgtcgaatt tttcgagcgc gcgagcactc tgcgccgtcg     360
cccgcctcgt ctcgaggtcc tgacggggtg acgtggagct cggtcgccag cgagcacctc     420
gactgacctc gctcgcctcg ctctcgtctg ccaggttcgt tcaagtacgc atgggtcctc     480
gacaagctca aggccgagcg cgagcgtggt atcaccatcg acatcgctct ctggaagttc     540
gagaccccca aggttcgttc gccgtctttc gtctcgcctc gcaactgagt gctaacgtgc     600
gcccgcacgc agtacatgat caccgtcatc gacgcccggg tcaccgtga cttcatcaag      660
aacatgatca ccgtaccctc gcaggccgac tgcgccatcc tcatcattgc cgccggcact     720
ggtgagttcg aggccggtat ctcgaaggac ggccagaccc gcgagcacgc cctcctcgcc     780
ttcaccctcg gtgtccgcca gctcatcgtt gccatcaaca agatggacac gaccaagtac     840
tcggaggccc gttacgagga gatcatcaag gagacgtcca actttatcaa gaaggtcggc     900
ttcaaccccca agggcgtccc cttcgtcccc atctcgggat ggcacggcga caacatgatc     960
```

-continued

```
gaggcgacca ccaacatgcc ctggtacaag ggatggaaga aggagaccaa gtcgggcgag    1020
gtcaccggca agaccctcct cgacgccatc gacgccatcg agccccctc gcgcccacc     1080 gacaagcccc tccgtcttcc cctccaggtg cgttcgctcg ttctcgcttg tttgcgaccc    1140
tcctcgctga cactcgtctt cgctcgcaca ggacgtctac aagatcggcg gtatcggcac    1200
agtgcccgtc ggccgtgtcg agactggcac gatcaaggcc ggcatggtcg tcaccttcgc    1260
cccgtcgaac gtcaccaccg aggtcaagtc ggtcgagatg caccacgagc agctcgaggc    1320
cggtctcccc ggagacaatg ttggcttcaa cgtcaagaac gtctcggtca aggacatccg    1380
ccgcggcaat gtctgcggtg actcgaagaa cgacccctcc caaggaggctg cgtcgttcaa    1440 ggcccaggtc atcgtcatga accaccccgg ccagatcggc aacggctacg cgcccgtcct    1500
cgactgccac acggcccaca ttgcgtgcaa gttcgacacg ctcctcgaga gatcgaccg     1560 ccgctcgggc aagtcggtcg aggacctccc caagttcatc aagtcgggtg acgccgccat    1620
cgtcaagatg gttccctcga agccgatgtg cgtcgagtcg ttcgccgagt accctccct     1680 cggtcgtttc gccgtccgtg acatgcgcca accgttgcc gtcggtgtca tcaaggtgcg     1740
tcccgcgttt ctctcgcatg ttctcgacag ctcaacgata ctgacgctgt tttccacgat    1800
tcaggcagtc gagaagactg acggcaaggg cggcaagggt gcgtcttttc tcctctctct    1860
cgtgcggagt cctctcgtct tggtgaccga gagctgacct cttccgtcct tcccttcctc    1920
ttccctcgtg cgctctctcc ctctcctacg ctcactcgtc gtgctcctct cgctgtcgcc    1980
tcactcgccc cttcgccgc cgcccctcg tacctgacg accctcctcg accacagtca      2040
ccaaggtccg tcctccttcc ttcctcgctc tctggcacaa cccgctgaca ctcccttgcc    2100
cacccgcagt cggcggagaa ggctgccggc aagaagaagt aa                       2142
```

<210> SEQ ID NO 112
<211> LENGTH: 1683
<212> TYPE: DNA
<213> ORGANISM: Rhodosporidium toruloides
<220> FEATURE:
<221> NAME/KEY: CDS
<222> LOCATION: (46)..(1431)

<400> SEQUENCE: 112

```
acctcgcgtc aaccctcgca tctcacacct acactcgcat tcaaa atg ggc aag gaa    57
                                                 Met Gly Lys Glu
                                                   1 aag gga cac gtc aac gtc gtc gtt atc ggc cac gtc gac tcc ggc aag     105
Lys Gly His Val Asn Val Val Val Ile Gly His Val Asp Ser Gly Lys
  5                  10                  15                  20 tcg acc acc acc gga cac ttg atc tac aag tgc ggc ggt atc gac aag     153
Ser Thr Thr Thr Gly His Leu Ile Tyr Lys Cys Gly Gly Ile Asp Lys
                 25                  30                  35 cgt acc atc gag aag ttc gag aag gag gcc gct gag ctc ggc aag ggt     201
Arg Thr Ile Glu Lys Phe Glu Lys Glu Ala Ala Glu Leu Gly Lys Gly
             40                  45                  50 tcg ttc aag tac gca tgg gtc ctc gac aag ctc aag gcc gag cgc gag     249
Ser Phe Lys Tyr Ala Trp Val Leu Asp Lys Leu Lys Ala Glu Arg Glu
         55                  60                  65 cgt ggt atc acc atc gac atc gct ctc tgg aag ttc gag acc ccc aag     297
Arg Gly Ile Thr Ile Asp Ile Ala Leu Trp Lys Phe Glu Thr Pro Lys
     70                  75                  80 tac atg atc acc gtc atc gac gcc ccg ggt cac cgt gac ttc atc aag     345
Tyr Met Ile Thr Val Ile Asp Ala Pro Gly His Arg Asp Phe Ile Lys
 85                  90                  95                 100
```

```
aac atg atc acc ggt acc tcg cag gcc gac tgc gcc atc ctc atc att    393
Asn Met Ile Thr Gly Thr Ser Gln Ala Asp Cys Ala Ile Leu Ile Ile
            105                 110                 115 gcc gcc ggc act ggt gag ttc gag gcc ggt atc tcg aag gac ggc cag    441
Ala Ala Gly Thr Gly Glu Phe Glu Ala Gly Ile Ser Lys Asp Gly Gln
            120                 125                 130 acc cgc gag cac gcc ctc ctc gcc ttc acc ctc ggt gtc cgc cag ctc    489
Thr Arg Glu His Ala Leu Leu Ala Phe Thr Leu Gly Val Arg Gln Leu
            135                 140                 145 atc gtt gcc atc aac aag atg gac acg acc aag tac tcg gag gcc cgt    537
Ile Val Ala Ile Asn Lys Met Asp Thr Thr Lys Tyr Ser Glu Ala Arg
150                 155                 160 tac gag gag atc atc aag gag acg tcc aac ttt atc aag aag gtc ggc    585
Tyr Glu Glu Ile Ile Lys Glu Thr Ser Asn Phe Ile Lys Lys Val Gly
165                 170                 175                 180 ttc aac ccc aag ggc gtc ccc ttc gtc ccc atc tcg gga tgg cac ggc    633
Phe Asn Pro Lys Gly Val Pro Phe Val Pro Ile Ser Gly Trp His Gly
                185                 190                 195 gac aac atg atc gag gcg acc acc aac atg ccc tgg tac aag gga tgg    681
Asp Asn Met Ile Glu Ala Thr Thr Asn Met Pro Trp Tyr Lys Gly Trp
            200                 205                 210 aag aag gag acc aag tcg ggc gag gtc acc ggc aag acc ctc ctc gac    729
Lys Lys Glu Thr Lys Ser Gly Glu Val Thr Gly Lys Thr Leu Leu Asp
            215                 220                 225 gcc atc gac gcc atc gag ccc ccc tcg cgc ccc acc gac aag ccc ctc    777
Ala Ile Asp Ala Ile Glu Pro Pro Ser Arg Pro Thr Asp Lys Pro Leu
            230                 235                 240 cgt ctt ccc ctc cag gac gtc tac aag atc ggc ggt atc ggc aca gtg    825
Arg Leu Pro Leu Gln Asp Val Tyr Lys Ile Gly Gly Ile Gly Thr Val
245                 250                 255                 260 ccc gtc ggc cgt gtc gag act ggc acg atc aag gcc ggc atg gtc gtc    873
Pro Val Gly Arg Val Glu Thr Gly Thr Ile Lys Ala Gly Met Val Val
                265                 270                 275 acc ttc gcc ccg tcg aac gtc acc acc gag gtc aag tcg gtc gag atg    921
Thr Phe Ala Pro Ser Asn Val Thr Thr Glu Val Lys Ser Val Glu Met
            280                 285                 290 cac cac gag cag ctc gag gcc ggt ctc ccc gga gac aat gtt ggc ttc    969
His His Glu Gln Leu Glu Ala Gly Leu Pro Gly Asp Asn Val Gly Phe
            295                 300                 305 aac gtc aag aac gtc tcg gtc aag gac atc cgc cgc ggc aat gtc tgc   1017
Asn Val Lys Asn Val Ser Val Lys Asp Ile Arg Arg Gly Asn Val Cys
            310                 315                 320 ggt gac tcg aag aac gac cct ccc aag gag gct gcg tcg ttc aag gcc   1065
Gly Asp Ser Lys Asn Asp Pro Pro Lys Glu Ala Ala Ser Phe Lys Ala
325                 330                 335                 340 cag gtc atc gtc atg aac cac ccc ggc cag atc ggc aac ggc tac gcg   1113
Gln Val Ile Val Met Asn His Pro Gly Gln Ile Gly Asn Gly Tyr Ala
                345                 350                 355 ccc gtc ctc gac tgc cac acg gcc cac att gcg tgc aag ttc gac acg   1161
Pro Val Leu Asp Cys His Thr Ala His Ile Ala Cys Lys Phe Asp Thr
            360                 365                 370 ctc ctc gag aag atc gac cgc cgc tcg ggc aag tcg gtc gag gac ctc   1209
Leu Leu Glu Lys Ile Asp Arg Arg Ser Gly Lys Ser Val Glu Asp Leu
            375                 380                 385 ccc aag ttc atc aag tcg ggt gac gcc gcc atc gtc aag atg gtt ccc   1257
Pro Lys Phe Ile Lys Ser Gly Asp Ala Ala Ile Val Lys Met Val Pro
            390                 395                 400 tcg aag ccg atg tgc gtc gag tcg ttc gcc gag tac cct ccc ctc ggt   1305
Ser Lys Pro Met Cys Val Glu Ser Phe Ala Glu Tyr Pro Pro Leu Gly
```

-continued

```
              405                 410                 415                 420
cgt ttc gcc gtc cgt gac atg cgc cag acc gtt gcc gtc ggt gtc atc      1353
Arg Phe Ala Val Arg Asp Met Arg Gln Thr Val Ala Val Gly Val Ile
                    425                 430                 435 aag gca gtc gag aag act gac ggc aag ggc ggc aag gtc acc aag tcg      1401
Lys Ala Val Glu Lys Thr Asp Gly Lys Gly Gly Lys Val Thr Lys Ser
                    440                 445                 450 gcg gag aag gct gcc ggc aag aag aag taa acgggcggac tcgaacaagt        1451
Ala Glu Lys Ala Ala Gly Lys Lys Lys
                    455                 460 cccctcgcac gcttctcctt cctctcgctc cccacctcgc attccacacg cctttccgga    1511
tacgaagcag cagtcgtgtc tgaacaacgc ctctctccct ctccctccat ccgcttgtcg    1571
tcatcgcttg atcccctccc ctcctcccga gcgtgttgtt ccctctgcct gctgtctagg    1631
actcctgaaa ggtttacccc ccgtttcgtg tgcaattcgg tttgactcca ta            1683
```

<210> SEQ ID NO 113
<211> LENGTH: 461
<212> TYPE: PRT
<213> ORGANISM: Rhodosporidium toruloides

<400> SEQUENCE: 113

```
Met Gly Lys Glu Lys Gly His Val Asn Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Leu Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ala Leu Trp Lys Phe
65                  70                  75                  80

Glu Thr Pro Lys Tyr Met Ile Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Ile Leu Ile Ile Ala Ala Gly Thr Gly Glu Phe Glu Ala Gly Ile Ser
        115                 120                 125

Lys Asp Gly Gln Thr Arg Glu His Ala Leu Leu Ala Phe Thr Leu Gly
    130                 135                 140

Val Arg Gln Leu Ile Val Ala Ile Asn Lys Met Asp Thr Thr Lys Tyr
145                 150                 155                 160

Ser Glu Ala Arg Tyr Glu Glu Ile Ile Lys Glu Thr Ser Asn Phe Ile
                165                 170                 175

Lys Lys Val Gly Phe Asn Pro Lys Gly Val Pro Phe Val Pro Ile Ser
            180                 185                 190

Gly Trp His Gly Asp Asn Met Ile Glu Ala Thr Thr Asn Met Pro Trp
        195                 200                 205

Tyr Lys Gly Trp Lys Lys Glu Thr Lys Ser Gly Glu Val Thr Gly Lys
    210                 215                 220

Thr Leu Leu Asp Ala Ile Asp Ala Ile Glu Pro Ser Arg Pro Thr
225                 230                 235                 240

Asp Lys Pro Leu Arg Leu Pro Leu Gln Asp Val Tyr Lys Ile Gly Gly
                245                 250                 255

Ile Gly Thr Val Pro Val Gly Arg Val Glu Thr Gly Thr Ile Lys Ala
```

```
                260              265              270
Gly Met Val Val Thr Phe Ala Pro Ser Asn Val Thr Thr Glu Val Lys
            275              280              285
Ser Val Glu Met His His Glu Gln Leu Glu Ala Gly Leu Pro Gly Asp
            290              295              300
Asn Val Gly Phe Asn Val Lys Asn Val Ser Val Lys Asp Ile Arg Arg
305              310              315              320
Gly Asn Val Cys Gly Asp Ser Lys Asn Asp Pro Pro Lys Glu Ala Ala
                325              330              335
Ser Phe Lys Ala Gln Val Ile Val Met Asn His Pro Gly Gln Ile Gly
            340              345              350
Asn Gly Tyr Ala Pro Val Leu Asp Cys His Thr Ala His Ile Ala Cys
            355              360              365
Lys Phe Asp Thr Leu Leu Glu Lys Ile Asp Arg Arg Ser Gly Lys Ser
            370              375              380
Val Glu Asp Leu Pro Lys Phe Ile Lys Ser Gly Asp Ala Ala Ile Val
385              390              395              400
Lys Met Val Pro Ser Lys Pro Met Cys Val Glu Ser Phe Ala Glu Tyr
                405              410              415
Pro Pro Leu Gly Arg Phe Ala Val Arg Asp Met Arg Gln Thr Val Ala
            420              425              430
Val Gly Val Ile Lys Ala Val Glu Lys Thr Asp Gly Lys Gly Gly Lys
            435              440              445
Val Thr Lys Ser Ala Glu Lys Ala Ala Gly Lys Lys Lys
            450              455              460

<210> SEQ ID NO 114
<211> LENGTH: 1003
<212> TYPE: DNA
<213> ORGANISM: Rhodosporidium toruloides

<400> SEQUENCE: 114
gcacgcgaag cggtagaagc aatgaagcga ggcgagagcg agagaggcag ggcttcagcc     60
atgtccagct gatcggctgt aacgtcgcgc cgggccagtc tgttgaattt gttgcgtcgc    120
ctgagcgtaa tagaagtgca gtagtctact ccgcatgccg agaacgtcga agagcgcgaa    180
gtagggagtc gagggaagcg agggtggcaa acacagcaac gacaagcggt tccgcttcgc    240
tcaaaagctc gttgacgttg ttttgacgtt ttgaagacag tacaacagca gcaagaggcg    300
tgcgaagcgt tggtggcgag agcagcgaca aggaggagg aatgagggag tggtggcgag    360
ggctcgcaaa cgggcgtacg cctcgaatgg agacgtgcga gtcgttcttc gacgtccgag    420
ggatgccgag cgccgagacg gagcacgcaa cgagcgagag gagagcagcc gcgcaaggtg    480
attcgagtgg cgcaagcgga ggacgacgag gagacggacg agggaggagg agggatggcg    540
agcgagcatc ggacggcggg gcgcgagaga cggcgtgagg agccgggtgt ggagagtttg    600
aggaggcgcg ggatgcgaag tggctgggtg tgcggagtga gcggtggcaa agagcgcact    660
tagagtctag agcgaggcag tagtagtaga gctgtatgaa tgaatacaaa gtgtgaatac    720
aacagtttgt aatgcgattc tgagcttgga cgtgtgcgcg cgagagggcg acttgcaagc    780
cagcgcccgc tcgctcttct tccttctgca cctcgcgtca accctcgcat ctcacaccta    840
cactcgcatt caaagtgcgt acactctccc acgacacacg gggacggcgc acaccaccgc    900
gcgtcgcttc aacggcgtcg ccacttcgag ccgtcactga cttcgtcctc gtcctccctc    960
ctctactctc ttgtactgta ctgtgtactg gggggatag atg                      1003
```

<210> SEQ ID NO 115
<211> LENGTH: 1134
<212> TYPE: DNA
<213> ORGANISM: Rhodosporidium toruloides

<400> SEQUENCE: 115

```
gcacgcgaag cggtagaagc aatgaagcga ggcgagagcg agagaggcag ggcttcagcc      60
atgtccagct gatcggctgt aacgtcgcgc cgggccagtc tgttgaattt gttgcgtcgc     120
ctgagcgtaa tagaagtgca gtagtctact ccgcatgccg agaacgtcga agagcgcgaa     180
gtagggagtc gagggaagcg agggtggcaa acacagcaac gacaagcggt tccgcttcgc     240
tcaaaagctc gttgacgttg ttttgacgtt ttgaagacag tacaacagca gcaagaggcg     300
tgcgaagcgt tggtggcgag agcagcgaca aggaggagg aatgagggag tggtggcgag      360
ggctcgcaaa cgggcgtacg cctcgaatgg agacgtgcga gtcgttcttc gacgtccgag     420
ggatgccgag cgccgagacg gagcacgcaa cgagcgagag gagagcagcc gcgcaaggtg     480
attcgagtgg cgcaagcgga ggacgacgag gagacggacg agggaggagg agggatggcg     540
agcgagcatc ggacggcggg gcgcgagaga cggcgtgagg agccgggtgt ggagagtttg     600
aggaggcgcg ggatgcgaag tggctgggtg tgcggagtga gcggtggcaa agagcgcact     660
tagagtctag agcgaggcag tagtagtaga gctgtatgaa tgaatacaaa gtgtgaatac     720
aacagtttgt aatgcgattc tgagcttgga cgtgtgcgcg cgagagggcg acttgcaagc     780
cagcgcccgc tcgctcttct tccttctgca cctcgcgtca accctcgcat ctcacaccta     840
cactcgcatt caaagtgcgt acactctccc acgacacacg gggacggcgc acaccaccgc     900
gcgtcgcttg aacggcgtcg ccacttcgag ccgtcactga cttcgtcctc gtcctccctc     960
ctctactctc ttgtactgta ctgtgtactg gggggggatag atgggcaagg aaaagggaca    1020
cgtcaacgtc gtcgttatcg gtacgttcag cgtcgtcgag gcgagtctgg cgaggaggag    1080
gacgtcgagc tgacctcgcc ccgtcctccc gcgcaggcca cgtcgactcc atgg          1134
```

<210> SEQ ID NO 116
<211> LENGTH: 1134
<212> TYPE: DNA
<213> ORGANISM: Rhodosporidium toruloides

<400> SEQUENCE: 116

```
gcacgcgaag cggtagaagc aatgaagcga ggcgagagcg agagaggcag ggcttcagcc      60
atgtccagct gatcggctgt aacgtcgcgc cgggccagtc tgttgaattt gttgcgtcgc     120
ctgagcgtaa tagaagtgca gtagtctact ccgcatgccg agaacgtcga agagcgcgaa     180
gtagggagtc gagggaagcg agggtggcaa acacagcaac gacaagcggt tccgcttcgc     240
tcaaaagctc gttgacgttg ttttgacgtt ttgaagacag tacaacagca gcaagaggcg     300
tgcgaagcgt tggtggcgag agcagcgaca aggaggagg aatgagggag tggtggcgag      360
ggctcgcaaa cgggcgtacg cctcgaatgg agacgtgcga gtcgttcttc gacgtccgag     420
ggatgccgag cgccgagacg gagcacgcaa cgagcgagag gagagcagcc gcgcaaggtg     480
attcgagtgg cgcaagcgga ggacgacgag gagacggacg agggaggagg agggatggcg     540
agcgagcatc ggacggcggg gcgcgagaga cggcgtgagg agccgggtgt ggagagtttg     600
aggaggcgcg ggatgcgaag tggctgggtg tgcggagtga gcggtggcaa agagcgcact     660
tagagtctag agcgaggcag tagtagtaga gctgtatgaa tgaatacaaa gtgtgaatac     720
```

```
aacagtttgt aatgcgattc tgagcttgga cgtgtgcgcg cgagagggcg acttgcaagc      780
cagcgcccgc tcgctcttct tccttctgca cctcgcgtca accctcgcat ctcacaccta      840
cactcgcatt caaagtgcgt acactctccc acgacacacg gggacggcgc acaccaccgc      900
gcgtcgcttg aacggcgtcg ccacttcgag ccgtcactga cttcgtcctc gtcctccctc      960
ctctactctc ttgtactgta ctgtgtactg gggggatag atcggcaagg aaaagggaca       1020
cgtcaacgtc gtcgttatcg gtacgttcag cgtcgtcgag gcgagtctgg cgaggaggag      1080
gacgtcgagc tgacctcgcc ccgtcctccc gcgcaggcca cgtcgactcc atgg            1134
```

<210> SEQ ID NO 117
<211> LENGTH: 1133
<212> TYPE: DNA
<213> ORGANISM: Rhodosporidium toruloides

<400> SEQUENCE: 117

```
gcacgcgaag cggtagaagc aatgaagcga ggcgagagcg agagaggcag ggcttcagcc      60
atgtccagct gatcggctgt aacgtcgcgc cgggccagtc tgttgaattt gttgcgtcgc      120
ctgagcgtaa tagaagtgca gtagtctact ccgcatgccg agaacgtcga agagcgcgaa      180
gtagggagtc gagggaagcg agggtggcaa acacagcaac gacaagcggt tccgcttcgc      240
tcaaaagctc gttgacgttg ttttgacgtt ttgaagacag tacaacagca gcaagaggcg      300
tgcgaagcgt tggtggcgag agcagcgaca aggaggagg aatgagggag tggtggcgag       360
ggctcgcaaa cgggcgtacg cctcgaatgg agacgtgcga gtcgttcttc gacgtccgag      420
ggatgccgag cgccgagacg gagcacgcaa cgagcgagag gagagcagcc gcgcaaggtg      480
attcgagtgg cgcaagcgga ggacgacgag gagacggacg agggaggagg agggatggcg      540
agcgagcatc ggacggcggg gcgcgagaga cggcgtgagg agccgggtgt ggagagtttg      600
aggaggcgcg ggatgcgaag tggctgggtg tgcggagtga gcggtggcaa agagcgcact      660
tagagtctag agcgaggcag tagtagtaga gctgtatgaa tgaatacaaa gtgtgaatac      720
aacagtttgt aatgcgattc tgagcttgga cgtgtgcgcg cgagagggcg acttgcaagc      780
cagcgcccgc tcgctcttct tccttctgca cctcgcgtca accctcgcat ctcacaccta      840
cactcgcatt caaagtgcgt acactctccc acgacacacg gggacggcgc acaccaccgc      900
gcgtcgcttg aacggcgtcg ccacttcgag ccgtcactga cttcgtcctc gtcctccctc      960
ctctactctc ttgtactgta ctgtgtactg gggggatag atgggcaagg aaaagggaca       1020
cgtcaacgtc gtcgttatcg gtacgttcag cgtcgtcgag gcgagtctgg cgaggaggag      1080
gacgtcgagc tgacctcgcc ccgtcctccc gcgcaggcca cgtcgactcc atg             1133
```

<210> SEQ ID NO 118
<211> LENGTH: 1133
<212> TYPE: DNA
<213> ORGANISM: Rhodosporidium toruloides

<400> SEQUENCE: 118

```
gcacgcgaag cggtagaagc aatgaagcga ggcgagagcg agagaggcag ggcttcagcc      60
atgtccagct gatcggctgt aacgtcgcgc cgggccagtc tgttgaattt gttgcgtcgc      120
ctgagcgtaa tagaagtgca gtagtctact ccgcatgccg agaacgtcga agagcgcgaa      180
gtagggagtc gagggaagcg agggtggcaa acacagcaac gacaagcggt tccgcttcgc      240
tcaaaagctc gttgacgttg ttttgacgtt ttgaagacag tacaacagca gcaagaggcg      300
tgcgaagcgt tggtggcgag agcagcgaca aggaggagg aatgagggag tggtggcgag       360
```

```
ggctcgcaaa cgggcgtacg cctcgaatgg agacgtgcga gtcgttcttc gacgtccgag      420
ggatgccgag cgccgagacg gagcacgcaa cgagcgagag gagagcagcc gcgcaaggtg      480
attcgagtgg cgcaagcgga ggacgacgag gagacggacg agggaggagg agggatggcg      540
agcgagcatc ggacgcggg gcgcgagaga cggcgtgagg agccgggtgt ggagagtttg      600
aggaggcgcg ggatgcgaag tggctggtg tgcggagtga gcggtggcaa agagcgcact      660
tagagtctag agcgaggcag tagtagtaga gctgtatgaa tgaatacaaa gtgtgaatac      720
aacagtttgt aatgcgattc tgagcttgga cgtgtgcgcg cgagagggcg acttgcaagc      780
cagcgcccgc tcgctcttct tccttctgca cctcgcgtca accctcgcat ctcacaccta      840
cactcgcatt caaagtgcgt acactctccc acgacacacg gggacggcgc acaccaccgc      900
gcgtcgcttg aacggcgtcg ccacttcgag ccgtcactga cttcgtcctc gtcctccctc      960
ctctactctc ttgtactgta ctgtgtactg ggggggatag atcggcaagg aaaagggaca     1020
cgtcaacgtc gtcgttatcg gtacgttcag cgtcgtcgag gcgagtctgg cgaggaggag     1080
gacgtcgagc tgacctcgcc ccgtcctccc gcgcaggcca cgtcgactcc atg           1133
```

<210> SEQ ID NO 119
<211> LENGTH: 931
<212> TYPE: DNA
<213> ORGANISM: Rhodosporidium toruloides

<400> SEQUENCE: 119

```
gtggcaaaca cagcaacgac aagcggttcc gcttcgctca aaagctcgtt gacgttgttt       60
tgacgttttg aagacagtac aacagcagca agaggcgtgc gaagcgttgg tggcgagagc      120
agcgacaagg agggaggaat gagggagtgg tggcgagggc tcgcaaacgg gcgtacgcct      180
cgaatggaga cgtgcgagtc gttcttcgac gtccgaggga tgccgagcgc cgagacggag      240
cacgcaacga gcgagaggag agcagccgcc caaggtgatt cgagtggcgc aagcggagga      300
cgacgaggag acggacgagg gaggaggagg gatggcgagc gagcatcgga cggcggggcg      360
cgagagacgg cgtgaggagc cgggtgtgga gagtttgagg aggcgcggga tgcgaagtgg      420
ctgggtgtgc ggagtgagcg gtggcaaaga gcgcacttag agtctagagc gaggcagtag      480
tagtagagct gtatgaatga atacaaagtg tgaatacaac agtttgtaat gcgattctga      540
gcttggacgt gtgcgcgcga gagggcgact tgcaagccag cgcccgctcg ctcttcttcc      600
ttctgcacct cgcgtcaacc ctcgcatctc acacctacac tcgcattcaa agtgcgtaca      660
ctctcccacg acacacgggg acggcgcaca ccaccgcgcg tcgcttgaac ggcgtcgcca      720
cttcgagccg tcactgactt cgtcctcgtc ctcctcctc tactctcttg tactgtactg      780
tgtactgggg gggatagatg ggcaaggaaa agggacacgt caacgtcgtc gttatcggta      840
cgttcagcgt cgtcgaggcg agtctggcga ggaggaggac gtcgagctga cctcgccccg      900
tcctcccgcg caggccacgt cgactccatg g                                    931
```

<210> SEQ ID NO 120
<211> LENGTH: 931
<212> TYPE: DNA
<213> ORGANISM: Rhodosporidium toruloides

<400> SEQUENCE: 120

```
gtggcaaaca cagcaacgac aagcggttcc gcttcgctca aaagctcgtt gacgttgttt       60
tgacgttttg aagacagtac aacagcagca agaggcgtgc gaagcgttgg tggcgagagc      120
```

| | |
|---|---:|
| agcgacaagg agggaggaat gagggagtgg tggcgagggc tcgcaaacgg gcgtacgcct | 180 |
| cgaatggaga cgtgcgagtc gttcttcgac gtccgaggga tgccgagcgc cgagacggag | 240 |
| cacgcaacga gcgagaggag agcagccgcg caaggtgatt cgagtggcgc aagcggagga | 300 |
| cgacgaggag acgacgagg gaggaggagg gatggcgagc gagcatcgga cggcggggcg | 360 |
| cgagagacgg cgtgaggagc cgggtgtgga gagtttgagg aggcgcggga tgcgaagtgg | 420 |
| ctgggtgtgc ggagtgagcg gtggcaaaga gcgcacttag agtctagagc gaggcagtag | 480 |
| tagtagagct gtatgaatga atacaaagtg tgaatacaac agtttgtaat gcgattctga | 540 |
| gcttggacgt gtgcgcgcga gagggcgact tgcaagccag cgcccgctcg ctcttcttcc | 600 |
| ttctgcacct cgcgtcaacc ctcgcatctc acacctacac tcgcattcaa agtgcgtaca | 660 |
| ctctcccacg acacacgggg acggcgcaca ccaccgcgcg tcgcttgaac ggcgtcgcca | 720 |
| cttcgagccg tcactgactt cgtcctcgtc ctccctcctc tactctcttg tactgtactg | 780 |
| tgtactgggg gggatagatc ggcaaggaaa agggacacgt caacgtcgtc gttatcggta | 840 |
| cgttcagcgt cgtcgaggcg agtctggcga ggaggaggac gtcgagctga cctcgccccg | 900 |
| tcctcccgcg caggccacgt cgactccatg g | 931 |

<210> SEQ ID NO 121
<211> LENGTH: 930
<212> TYPE: DNA
<213> ORGANISM: Rhodosporidium toruloides

<400> SEQUENCE: 121

| | |
|---|---:|
| gtggcaaaca cagcaacgac aagcggttcc gcttcgctca aaagctcgtt gacgttgttt | 60 |
| tgacgttttg aagacagtac aacagcagca agaggcgtgc gaagcgttgg tggcgagagc | 120 |
| agcgacaagg agggaggaat gagggagtgg tggcgagggc tcgcaaacgg gcgtacgcct | 180 |
| cgaatggaga cgtgcgagtc gttcttcgac gtccgaggga tgccgagcgc cgagacggag | 240 |
| cacgcaacga gcgagaggag agcagccgcg caaggtgatt cgagtggcgc aagcggagga | 300 |
| cgacgaggag acgacgagg gaggaggagg gatggcgagc gagcatcgga cggcggggcg | 360 |
| cgagagacgg cgtgaggagc cgggtgtgga gagtttgagg aggcgcggga tgcgaagtgg | 420 |
| ctgggtgtgc ggagtgagcg gtggcaaaga gcgcacttag agtctagagc gaggcagtag | 480 |
| tagtagagct gtatgaatga atacaaagtg tgaatacaac agtttgtaat gcgattctga | 540 |
| gcttggacgt gtgcgcgcga gagggcgact tgcaagccag cgcccgctcg ctcttcttcc | 600 |
| ttctgcacct cgcgtcaacc ctcgcatctc acacctacac tcgcattcaa agtgcgtaca | 660 |
| ctctcccacg acacacgggg acggcgcaca ccaccgcgcg tcgcttgaac ggcgtcgcca | 720 |
| cttcgagccg tcactgactt cgtcctcgtc ctccctcctc tactctcttg tactgtactg | 780 |
| tgtactgggg gggatagatg ggcaaggaaa agggacacgt caacgtcgtc gttatcggta | 840 |
| cgttcagcgt cgtcgaggcg agtctggcga ggaggaggac gtcgagctga cctcgccccg | 900 |
| tcctcccgcg caggccacgt cgactccatg | 930 |

<210> SEQ ID NO 122
<211> LENGTH: 930
<212> TYPE: DNA
<213> ORGANISM: Rhodosporidium toruloides

<400> SEQUENCE: 122

| | |
|---|---:|
| gtggcaaaca cagcaacgac aagcggttcc gcttcgctca aaagctcgtt gacgttgttt | 60 |
| tgacgttttg aagacagtac aacagcagca agaggcgtgc gaagcgttgg tggcgagagc | 120 |

-continued

```
agcgacaagg agggaggaat gagggagtgg tggcgagggc tcgcaaacgg gcgtacgcct      180
cgaatggaga cgtgcgagtc gttcttcgac gtccgaggga tgccgagcgc cgagacggag      240
cacgcaacga gcgagaggag agcagccgcg caaggtgatt cgagtggcgc aagcggagga      300
cgacgaggag acggacgagg gaggaggagg gatggcgagc gagcatcgga cggcggggcg      360
cgagagacgg cgtgaggagc cgggtgtgga gagtttgagg aggcgcggga tgcgaagtgg      420
ctgggtgtgc ggagtgagcg gtggcaaaga gcgcacttag agtctagagc gaggcagtag      480
tagtagagct gtatgaatga atacaaagtg tgaatacaac agtttgtaat gcgattctga      540
gcttggacgt gtgcgcgcga gagggcgact tgcaagccag cgcccgctcg ctcttcttcc      600
ttctgcacct cgcgtcaacc ctcgcatctc acacctacac tcgcattcaa agtgcgtaca      660
ctctcccacg acacacgggg acggcgcaca ccaccgcgcg tcgcttgaac ggcgtcgcca      720
cttcgagccg tcactgactt cgtcctcgtc ctccctcctc tactctcttg tactgtactg      780
tgtactgggg gggatagatc ggcaaggaaa agggacacgt caacgtcgtc gttatcggta      840
cgttcagcgt cgtcgaggcg agtctggcga ggaggaggac gtcgagctga cctcgccccg      900
tcctcccgcg caggccacgt cgactccatg                                        930
```